United States Patent
Koshti

(10) Patent No.: US 10,332,248 B1
(45) Date of Patent: Jun. 25, 2019

(54) CONTRAST BASED IMAGING AND ANALYSIS COMPUTER-IMPLEMENTED METHOD TO ANALYZE PULSE THERMOGRAPHY DATA FOR NONDESTRUCTIVE EVALUATION

(71) Applicant: The United States of America as represented by the Administrator of NASA, Washington, DC (US)

(72) Inventor: Ajay M. Koshti, League City, TX (US)

(73) Assignee: The United States of America as represented by the Administator of the National Aeronautics and Space Administration, Washington, DC (US)

( * ) Notice: Subject to any disclaimer, the term of this patent is extended or adjusted under 35 U.S.C. 154(b) by 121 days.

(21) Appl. No.: 15/678,933

(22) Filed: Aug. 16, 2017

Related U.S. Application Data

(60) Provisional application No. 62/376,276, filed on Aug. 17, 2016.

(51) Int. Cl.
*G06K 9/00* (2006.01)
*G06T 7/00* (2017.01)
(Continued)

(52) U.S. Cl.
CPC ........... *G06T 7/0006* (2013.01); *G01N 25/72* (2013.01); *G06T 5/002* (2013.01); *G06T 5/008* (2013.01); *G06T 7/001* (2013.01); *G06T 7/11* (2017.01); *G06T 7/13* (2017.01); *G06T 7/62* (2017.01); *G06T 5/20* (2013.01);
(Continued)

(58) Field of Classification Search
CPC ....... G06T 7/0006; G06T 5/007; G06T 5/002; G06T 7/13; G06T 7/001; G06T 7/62; G06T 7/50; G06T 2207/20076; G06T 2207/10048; G06T 2207/10016; G06T 2207/20212; G06T 5/20; G01N 25/72
See application file for complete search history.

(56) References Cited

U.S. PATENT DOCUMENTS 4,896,278 A  1/1990 Grove
5,619,326 A  4/1997 Takamatsu et al.
(Continued)

FOREIGN PATENT DOCUMENTS

GB  2471047 B  5/2012
WO  WO9940417 A1  8/1999
WO  WO9944366  9/1999

OTHER PUBLICATIONS

Larsen et al., Document Flash Thermography, pp. 1-9, 2011.

*Primary Examiner* — Phuoc Tran
(74) *Attorney, Agent, or Firm* — Kurt G. Hammerle; Edward K. Fein; Mark P. Dvorscak

(57) ABSTRACT

Methods and systems for analyzing and processing digital data comprising a plurality of infra-red (IR) video images acquired by a pulse thermography system are used to compute video data from the raw and smoothed video data acquired for the performance of non-destructive evaluation. New video data types computed may include but are not limited to contrast evolution data such as normalized contrast, converted contrast and normalized temperature contrast. Additionally, video data types computed comprise surface temperature, surface temperature rise and temperature simple contrast.

35 Claims, 37 Drawing Sheets

(51) Int. Cl.
  *G06T 5/00* (2006.01)
  *G06T 7/11* (2017.01)
  *G06T 7/13* (2017.01)
  *G06T 7/62* (2017.01)
  *G01N 25/72* (2006.01)
  *G06T 5/20* (2006.01)

(52) U.S. Cl.
  CPC ............... *G06T 2207/10016* (2013.01); *G06T 2207/10048* (2013.01); *G06T 2207/20076* (2013.01); *G06T 2207/20212* (2013.01)

(56) References Cited

U.S. PATENT DOCUMENTS

| | | |
|---|---|---|
| 5,711,603 A | 1/1998 | Ringermacher et al. |
| 6,122,060 A | 9/2000 | Drake, Jr. |
| 6,394,646 B1 | 5/2002 | Ringermacher et al. |
| 6,542,849 B2 | 4/2003 | Sun |
| 6,712,502 B2 | 3/2004 | Zalameda et al. |
| 6,751,342 B2 | 6/2004 | Shepard |
| 6,838,670 B2 | 1/2005 | Lewis et al. |
| 7,220,966 B2 | 5/2007 | Saito et al. |
| 7,457,455 B2 | 11/2008 | Matsui et al. |
| 7,591,583 B2 | 9/2009 | Foes et al. |
| 7,605,924 B2 | 10/2009 | Howard et al. |
| 8,055,054 B2 | 11/2011 | Ringermacher et al. |
| 8,126,267 B2 | 2/2012 | Talati et al. |
| 8,449,176 B2 | 5/2013 | Shepard |
| 8,577,120 B1 | 11/2013 | Koshti |
| 9,066,028 B1 | 6/2015 | Koshti |
| 2005/0008215 A1* | 1/2005 | Shepard .................. G01N 25/72 382/141 |
| 2009/0245321 A1* | 10/2009 | Ringermacher ........ G01N 25/72 374/5 |
| 2011/0189379 A1 | 8/2011 | Ortner et al. |
| 2012/0207379 A1 | 8/2012 | Shimodaira et al. |
| 2013/0061677 A1 | 3/2013 | Wang et al. |
| 2014/0085449 A1 | 3/2014 | Mandelis et al. |
| 2014/0236020 A1 | 8/2014 | Leschinsky et al. |
| 2015/0161778 A1 | 6/2015 | Henderkott et al. |

\* cited by examiner

Example Contrast Evolution Data file

Temperature - Time Data (16 - Bit Sums)
E:\Data\Text_files_new_format\Fixed 0001-.txt
Image size = 320 x 256
ROI Dimensions = 7 x 7
No. of Data Cube Images = 39
Real Frame Rate = 30.22
Effective Frame Rate = 30.22
Diameter(in.) = 0.0000, depth(in.) = 1.0000, Peak Time (s) = 0.0000, Scale factor ) = 1.0000, Offest =
0.0000, begin Time = 0.0000, Slope = 1.0000

| Number | 1 | 2 |
|---|---|---|
| X-Pos | 91 | 117 |
| Y-Pos | 29 | 34 |
| -0.298 | 7758 | 7760 |
| -0.265 | 7758 | 7760 |
| -0.232 | 7758 | 7760 |
| -0.199 | 7758 | 7760 |
| -0.165 | 7758 | 7760 |
| -0.132 | 7758 | 7760 |
| -0.099 | 7758 | 7760 |
| -0.066 | 7758 | 7760 |
| -0.033 | 7758 | 7760 |
| 0.000 | 15807 | 15625 |

Continues till end of file

FIG. 12

| Hole No. | Diameter (in) | Depth (in) | Peak Contrast | Peak Time (s) | Time Scale Factor | Offset (s) | Begin Time (s) | Slope (1/s) |
|---|---|---|---|---|---|---|---|---|
| 1 | 0.125 | 0.01 | 14.828 | 0.811 | 1.365 | 0.222 | 0.145 | 61.980 |
| 2 | 0.125 | 0.02 | 9.800 | 1.440 | 1.004 | 0.364 | 0.230 | 20.354 |
| 3 | 0.125 | 0.03 | 6.200 | 2.548 | 0.709 | 0.587 | 0.366 | 6.281 |
| 4 | 0.125 | 0.04 | 3.300 | 3.294 | 0.867 | 0.528 | 0.403 | 2.012 |
| 5 | 0.125 | 0.05 | 1.800 | 4.500 | 0.600 | 0.694 | 0.493 | 0.799 |
| 6 | 0.25 | 0.01 | 30.143 | 1.585 | 0.656 | 0.323 | 0.168 | 61.454 |
| 7 | 0.25 | 0.02 | 20.403 | 2.300 | 1.068 | 0.289 | 0.165 | 16.910 |
| 8 | 0.25 | 0.03 | 15.903 | 3.300 | 0.652 | 0.587 | 0.342 | 10.387 |
| 9 | 0.25 | 0.04 | 9.800 | 4.410 | 0.597 | 0.960 | 0.724 | 4.806 |
| 10 | 0.25 | 0.05 | 8.356 | 5.803 | 0.420 | 1.289 | 0.920 | 3.289 |
| 11 | 0.375 | 0.01 | 43.000 | 2.656 | 0.452 | 0.263 | -0.022 | 41.488 |
| 12 | 0.375 | 0.02 | 25.000 | 3.978 | 0.504 | 0.628 | 0.307 | 13.653 |
| 13 | 0.375 | 0.03 | 20.200 | 4.890 | 0.406 | 0.876 | 0.479 | 8.916 |
| 14 | 0.375 | 0.04 | 13.900 | 6.310 | 0.430 | 1.306 | 1.001 | 4.652 |
| 15 | 0.375 | 0.05 | 11.600 | 7.525 | 0.370 | 1.504 | 1.180 | 3.173 |
| 16 | 0.5 | 0.01 | 50.092 | 3.321 | 0.388 | 0.182 | -0.201 | 31.466 |
| 17 | 0.5 | 0.02 | 32.200 | 5.130 | 0.353 | 0.678 | 0.222 | 13.420 |
| 18 | 0.5 | 0.03 | 24.600 | 6.792 | 0.280 | 1.165 | 0.591 | 8.155 |
| 19 | 0.5 | 0.04 | 19.025 | 6.749 | 0.500 | 1.000 | 0.954 | 5.441 |
| 20 | 0.5 | 0.05 | 13.800 | 8.147 | 0.410 | 1.536 | 1.434 | 3.360 |
| 21 | 0.625 | 0.01 | 50.000 | 4.926 | 0.267 | 0.339 | -0.213 | 21.793 |
| 22 | 0.625 | 0.02 | 36.500 | 6.000 | 0.352 | 0.578 | 0.156 | 11.264 |
| 23 | 0.625 | 0.03 | 29.500 | 7.000 | 0.350 | 0.959 | 0.583 | 8.062 |
| 24 | 0.625 | 0.04 | 25.800 | 8.606 | 0.330 | 1.157 | 0.877 | 5.722 |
| 25 | 0.625 | 0.05 | 18.700 | 9.240 | 0.380 | 1.545 | 1.542 | 3.923 |
| 26 | 0.75 | 0.01 | 55.000 | 6.590 | 0.173 | 0.379 | -0.353 | 20.713 |
| 27 | 0.75 | 0.02 | 41.200 | 8.321 | 0.179 | 0.835 | -0.025 | 10.698 |
| 28 | 0.75 | 0.03 | 34.000 | 9.039 | 0.240 | 1.074 | 0.455 | 7.171 |
| 29 | 0.75 | 0.04 | 26.600 | 9.000 | 0.360 | 1.091 | 1.028 | 5.482 |
| 30 | 0.75 | 0.05 | 20.400 | 9.760 | 0.460 | 1.397 | 1.902 | 3.997 |
| 31 | 0.875 | 0.01 | 57.300 | 7.027 | 0.160 | 0.364 | -0.427 | 19.962 |
| 32 | 0.875 | 0.02 | 43.000 | 8.000 | 0.237 | 0.587 | -0.082 | 10.248 |
| 33 | 0.875 | 0.03 | 36.000 | 10.000 | 0.224 | 1.008 | 0.381 | 6.663 |
| 34 | 0.875 | 0.04 | 30.800 | 10.160 | 0.270 | 1.157 | 0.815 | 5.590 |
| 35 | 0.875 | 0.05 | 23.700 | 10.000 | 0.350 | 1.595 | 1.593 | 4.578 |
| 36 | 1 | 0.01 | 60.000 | 9.089 | 0.095 | 0.529 | -0.477 | 18.746 |
| 37 | 1 | 0.02 | 45.000 | 9.500 | 0.150 | 0.793 | -0.232 | 9.793 |
| 38 | 1 | 0.03 | 38.200 | 10.310 | 0.195 | 0.950 | 0.159 | 6.988 |
| 39 | 1 | 0.04 | 32.700 | 10.420 | 0.240 | 1.215 | 0.716 | 5.814 |
| 40 | 1 | 0.05 | 28.000 | 10.320 | 0.340 | 1.041 | 1.170 | 4.919 |
| 41 | 1.125 | 0.01 | 56.600 | 9.000 | 0.124 | 0.430 | -0.586 | 15.362 |
| 42 | 1.125 | 0.02 | 50.600 | 10.000 | 0.120 | 0.810 | -0.338 | 11.346 |
| 43 | 1.125 | 0.03 | 37.200 | 11.090 | 0.190 | 1.198 | 0.386 | 6.634 |
| 44 | 1.125 | 0.04 | 32.600 | 10.850 | 0.250 | 1.165 | 0.795 | 5.482 |
| 45 | 1.125 | 0.05 | 22.200 | 11.580 | 0.410 | 1.347 | 2.140 | 3.620 |

CONTRAST BASED IMAGING AND ANALYSIS COMPUTER-IMPLEMENTED METHOD TO ANALYZE PULSE THERMOGRAPHY DATA FOR NONDESTRUCTIVE EVALUATION

CROSS-REFERENCE TO RELATED PATENT APPLICATION(S)

This patent application claims the benefit of and priority to U.S. Provisional Patent Application Ser. No. 62/376,276, filed Aug. 17, 2016, the contents of which are hereby incorporated by reference in their entirety.

STATEMENT OF GOVERNMENT INTEREST

The invention described herein was made by employee(s) of the United States Government and may be manufactured and used by or for the Government of the United States of America for governmental purposes without the payment of any royalties thereon or therefor.

FIELD OF THE INVENTION

The invention is directed to the general fields of nondestructive evaluation (NDE) and of processing of data acquired from an infrared camera. Specifically, the systems and methods described herein concern the performance of a series of steps for analyzing and processing digital data comprising a plurality of infra-red (IR) video images acquired by a system used for non-destructive evaluation.

BRIEF OVERVIEW

Infrared (IR) flash (or pulsed) thermography is an example of a technique for non-destructive evaluation (NDE) used primarily in the inspection of thin nonmetallic materials such as laminated or bonded composites in the aerospace industry. It is primarily used to detect delamination-like anomalies, although surface cracks are also detected to some extent. In most circumstances, a single sided or reflection technique is used where the flash lamp (heat source) and the IR camera (detector) are on the same side of the test object inspected.

The hardware equipment for an IR flash thermography system comprises a flash lamp (source of light/heat), a flash hood, a flash power supply/trigger unit, a flash duration controller, an IR camera for capturing video images, data acquisition electronics, and a personal computer (PC). See FIG. 1 for a schematic of a typical flash-hood set up. The PC is used for controlling the flash trigger, for acquiring video data from the IR camera, for displaying data, and for post-processing of the acquired data.

As one example of an NDE technique using IR flash thermography, a plate is provided as a test object with a round delamination in the center. See FIG. 2 for schematic of cross section of test object. In one example, the test plates have flat bottom holes drilled in them to simulate controlled diameter and depth delaminations as shown in FIG. 3. The holes may or may not be drilled to the same depth. In FIG. 4, the holes are drilled to different depths. There are five sizes of the diameter and three holes for each size. Thus, there are five groups of three identical holes. Hole sizes and their depths are for specimen B of FIG. 3 that are given in FIG. 4. Holes in each row have constant depth and remaining wall thickness.

After applying heat to the top surface of the test object by triggering the flash lamp, the top surface area surrounding the anomaly cools faster than the top surface (footprint) area above the anomaly. The IR camera captures a sequence of images of the surface temperature in terms of pixel intensity and shows the anomaly as a hot spot (e.g., an area warmer than the surrounding area or the reference region of interest—ROI) that is about the size and shape of the anomaly footprint. Relative pixel intensity, i.e., the difference in pixel intensity at the hot spot (measurement ROI) and the surrounding area (reference ROI), varies with the post-flash time. Example locations for measurement and reference ROI are illustrated in an example IR image of a graphite phenolic calibration standard shown in FIG. 5.

Deeper anomalies appear at later times in the IR video data compared to the near surface anomalies. After the appearance of an anomaly in the IR video data, the relative pixel intensity continues to increase with time. The relative pixel intensity of the anomaly reaches a peak at a certain time and then the relative pixel intensity decays until the temperature of the indication area and the temperature of the surrounding area become equal.

As discussed hereinafter, the embodiments described herein (a) define the normalized image contrast and the normalized temperature contrast and use calibrated simulation to interpret the contrast evolutions, and (b) calculate and image contrast video sequence data and contrast features. The embodiments described herein develop relationships between the normalized image contrast and the normalized temperature contrast by using equations of heat transfer. The embodiments described herein also develop methods of contrast video sequence data processing and feature imaging for anomaly detection and characterization as an enhancement of the contrast method.

SUMMARY

The embodiments described herein are applicable to flash (or pulsed) infrared thermography nondestructive evaluation and is an advancement of the various methods and systems described in U.S. Pat. Nos. 9,066,028 and 8,577,120. Contrast methods that further embody these methods and systems include: three contrast video image processing methods for processing raw or smoothed video imagery data in terms of pixel intensity into corresponding video thermal response data forms and their derivative video image data forms; a calibration and depth evaluation method; use of threshold in data analysis and other analysis methods; and thermography response-based probability of detection analysis.

The embodiments described herein may be divided into three categories, e.g., normalized or calibrated contrast evolution analysis, contrast feature imaging analysis, and thermography response-based accept/reject and probability of detection (POD) analysis.

Under the contrast evolution analysis, there are described herein three Contrast Video Image Processing (CVIP) methods as given below.

One contrast video image processing method is described herein as the Normalized Contrast and Derivatives (NCD) method. See generally FIG. 6. A second CVIP method is described herein as the Converted Contrast and Derivatives (CCD) method. See generally FIG. 7. A third CVIP method is described herein as the Normalized Temperature Contrast and Derivatives (TCD) method. See generally FIG. 8. The three methods described herein may be mutually exclusive, meaning each may be processed independent of the others. In other words, FIG. 6, FIG. 7 and FIG. 8 show an independent processing path for each method. Depending upon the user requirements, each method provides specific benefits.

Normalized Contrast and Derivative (NCD) Method

As shown generally in FIG. 6, normalized contrast video processing uses a change in pixel intensity from a discrete set of data (frame) sequences for further video data computing. Two methods of determining derivatives with respect to frame number (or time) have been provided, with each of the two methods branching into two possibilities as discussed below.

Method 1A: Derivative of raw or smooth and filtered (processed) contrast evolution.

Method 1B: Derivative of raw or smooth and filtered contrast evolution with smoothing during derivative computation.

Method 2A: Derivative of the simulation fit to a raw or filtered contrast evolution. The simulation fit is also a curve fit (e.g. polynomial fit).

Method 2B: Derivative of curve fit (non-simulation) to the raw or smooth (or processed) contrast evolutions.

In each method, the contrast video sequence data is computed and then converted to first derivative video sequence data and second derivative video sequence data. Derivatives are computed from filtered and smoothed (or processed) data or fitted data only. Derivatives are not typically computed on raw (unfiltered) contrast evolutions and some level of smoothing is applied to both first and second derivative. These videos are examined by playing the video forward or backward and selecting appropriate video frames for further analysis. This method is known as Frame Image Analysis (FIA).

Video Frame Images (e.g., normalized contrast at frame number 10) can be displayed for contrast and its derivatives and analyzed. Extracted feature images are generated by extracting features from a selected block of processed videos and then having them analyzed. This method is known as Extracted Image Analysis (EIA). Several non-derivative (e.g. peak or peak contrast, frame number at peak contrast) and derivative (e.g. peak first and second derivatives) features are extracted to make the images. Depending upon the extracted feature images, the images may reveal anomaly information such as the anomaly depth (frame number and derivative related images), anomaly size (contrast and contrast derivatives), and anomaly gap thickness (peak product time) and provide suppression of temporal and spatial noise. The images are described as the contrast A-scan (i.e. normalized contrast evolution at a pixel), contrast B-scan (i.e. stack of contrast evolutions for pixels on a line), contrast value C-scan (i.e. peak normalized contrast image) and contrast time of flight (TOF) C-scan (e.g. frame number at peak contrast image) similar to traditional industrial ultrasonic testing (ASTM F 2375) pulse/echo scans.

Converted Contrast and Derivative Method (CCD)

As shown generally in FIG. 7, converted contrast video processing uses a change in pixel intensity after a flash of heat and a multiplier for a measurement and a reference region of interest (ROI). The method allows extraction of pixel intensity-based converted contrast evolutions that have similar shape characteristics to corresponding normalized contrast evolutions. Pixel intensity contrast evolution data is transformed in accordance with this method. The converted contrast evolutions could be analyzed with measurement of converted contrast peak amplitude and converted contrast peak time. In addition, the first and second derivatives can also be computed. A method is provided to compute normalized contrast from the converted contrast evolutions. The derivative computation, selected Frame Image Analysis (FIA) and Extracted Image Analysis (EIA) are also implemented under the Converted Contrast Method. Similar to the description related to the computing of normalized contrast video, A-scan, B-scan and C-scans are possible with the converted contrast and the imaging results being comparable or better than the normalized contrast A-scan, B-scan and C-scans due to lower noise in the data.

Normalized Temperature Contrast and Derivatives (TCD) Method

As shown generally in FIG. 8, Normalized Temperature Contrast video processing uses a sequence of frames of surface temperature in terms of pixel intensity and computes video data using a change in pixel temperature. Temperature rise and simple contrast video sequence data are computed in this method. First and second derivative video sequence data of smooth normalized temperature contrast data are computed. Selected Frame Image Analysis (FIA) and Extracted Image Analysis (EIA) are also applicable to Normalized Temperature Contrast method. Similar to that for the normalized contrast video, A-scan, B-scan and C-scans are possible with the temperature contrast and imaging results are comparable to the normalized contrast A-scan, B-scan and C-scans.

The temperature contrast method reduces influence of diffused reflection from the part surface, enhancing the contrast. Also, surface temperature measurements are more quantitative than the pixel intensity measurements which contain both the emissive and reflective components of irradiance forming the image.

Contrast Evolution Calibration and Analysis (CECA) Method

In another embodiment, an empirical method of calibrating the flash thermography response in nondestructive evaluation is described. The contrast evolution calibration and analysis method (CECA) as shown generally in FIG. 9 is applied to contrast evolution data for a pixel with peak of relative contrast for the indication.

First, a physical calibration standard with artificial flaws such as flat bottom holes with desired diameter and depth values in a desired material is fabricated. An example calibration standard is shown in FIG. 4. Long flat bottom slots can be used in the calibration standard. For tight delaminations, use a standard that simulates the desired condition. U.S. Pat. No. 8,577,120 provided comparisons of normalized contrast response from slots and holes. As described in the '120 patent, slot width is mapped to equivalent flat bottom hole width, which then can be used in evaluating depth of long indications.

In this embodiment, normalized contrast evolution data for each artificial flaw in the reference standard is extracted from the raw video sequence data to provide calibration files that are loaded as a batch of calibration files as shown in FIG. 9. Contrast evolution files are analyzed in the contrast evolution evaluation methods provided. Six contrast parameters are preferably extracted for each flaw in the calibration standard. A calibration data set is prepared from the contrast parameter data. The calibration data is plotted by using an evolution evaluation and calibration method described herein. In order to analyze a given contrast evolution for flaw depth, contrast evolution parameters are calculated, and diameter or widths are measured in 2D images of the anomaly. Depth is assessed in this method by using the anomaly diameter or width, the six contrast evolution parameters, and calibration data. A single depth estimate can be interpolated from the multiple depth estimates, preferably one each from the six evolution parameters.

Other Image and Data Analysis Methods

These methods include providing Frame Images, Extracted Images, and Analysis of saved images. Video frame images are called Frame Images here. A frame number is associated with the frame image. Images extracted by scanning for values from multiple frames are called Extracted Images. A single frame number is not associated with an extracted image.

Within the three data analysis methods under this category, there are other sub-methods, including flaw size measurement, edge detection, image gray value profiling along vertical or horizontal lines, and image gray value profiling using peak of values scanned in vertical and horizontal directions.

FIG. 10 shows process flow chart for Extracted Images. Various examples of Extracted Image choices are discussed herein that provide useful information depending upon user need.

A method of image comparison (registration, subtraction and superimposition) to assess changes in thermography response (i.e. raw or processed pixel intensity data) and image tiling or mosaic is also used. Saved images are further analyzed by creating a mosaic. The images can be compared to reference images by a process called image registration and then subtracted from the reference images. Thus, differences in the thermal response (e.g., normalized contrast) can be quantified.

Thermography Response, Accept/Reject Threshold and Pod Analysis

The methods described under this category include quantitative thermography response such as the peak normalized contrast, peak converted contrast and peak normalized temperature contrast, simple contrast and referenced simple contrast. These methods can be used for flaw detection based on establishing an accept/reject threshold level for a thermography-based response. These thermography-based responses can then be used in probability of detection (POD) analysis using a thermography-based response correlation to diameter/depth ratio or a correlation of thermography-based response to both diameter and depth given as fitted surfaces.

BRIEF DESCRIPTION OF DRAWINGS

A more complete understanding of the embodiments described herein and many of the attendant advantages thereto will be readily appreciated as the same becomes better understood by reference to the following detailed description when considered in conjunction with the accompanying drawings, wherein:

FIG. 12 provides an example of a contrast evolution data file updated with calibration parameters in accord with one embodiment described herein.

FIG. 32 shows an example of Calibration Data in accord with one embodiment.

The above general description and the following detailed description are merely illustrative of the exemplary embodiments, and additional modes, advantages, and particulars of the exemplary embodiments will be readily apparent to those skilled in the art, now having the benefit of this disclosure, without departing from its spirit and scope as set forth in the appended claims.

DETAILED DESCRIPTION OF EXEMPLARY EMBODIMENTS

Detailed descriptions of the exemplary embodiments are provided herein. It is to be understood, however, that these embodiments may be modified in various forms. Therefore, specific details disclosed herein are not to be interpreted as limiting, but rather as a basis for understanding the claims and as a representative basis for teaching one skilled in the art how to employ the exemplary embodiments described herein for virtually any appropriately detailed system, structure or manner. Exemplary embodiments will now be described with reference to the accompanying figures.

Flash Thermography Equipment

Figure 1:
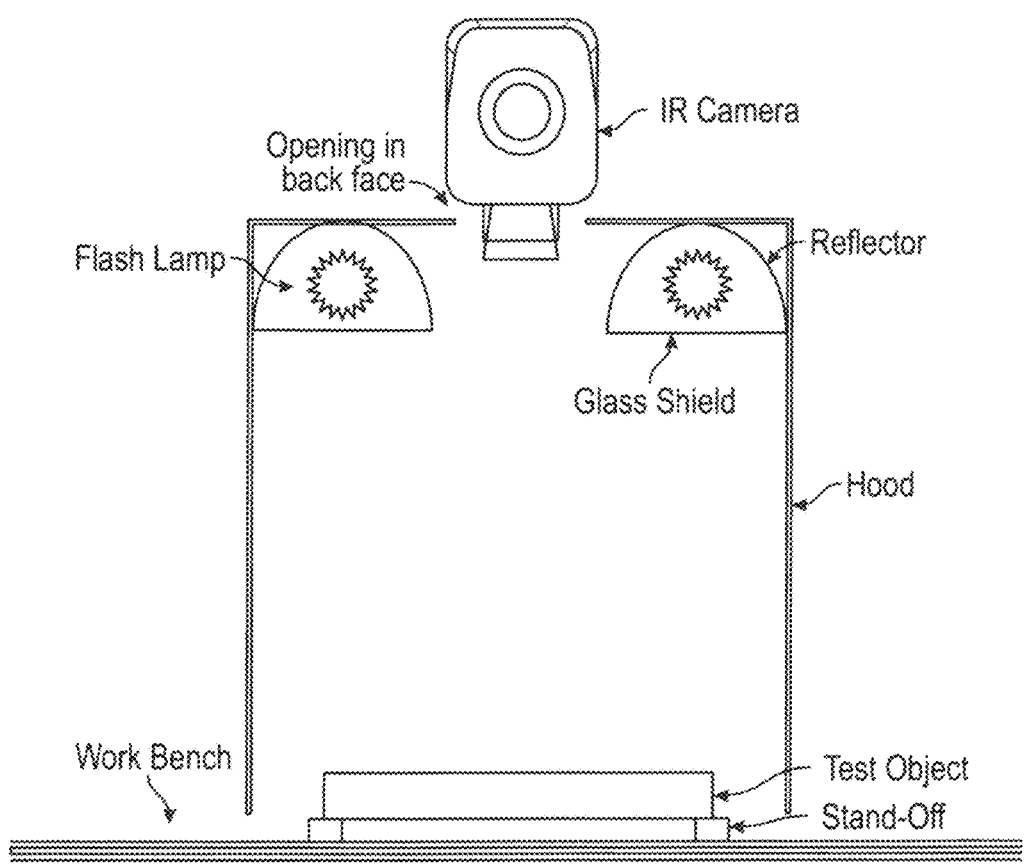
FIG. 1 provides a schematic of an exemplary single-sided flash thermography system.

As shown in FIG. 1, the equipment for an infrared flash thermography (IRFT) system in accordance with one of the exemplary embodiments described herein comprises a flash lamp (source of light/heat), a flash-hood, flash power supply/trigger unit, flash duration controller, an infrared (IR) camera for capturing video images, camera data acquisition electronics and a personal computer (PC). A PC is used for controlling the flash trigger for the flash lamp, data acquisition of the camera video data, data display, and post processing of the acquired data. The flash-hood may be made from a sheet metal. One of the six sides of the hood, which form a box, has a large opening so as to enable the hood to be positioned over a test object. The side opposite to the opening has a hole in the center to provide a window for lens of the IR camera that is mounted from outside of the hood. The IR camera is focused at the test object (part) surface located at the hood opening. At least one flash lamp (two are shown in FIG. 1) is located within the inner wall of the hood in proximity to the IR camera. The flash lamp(s) directs illumination towards the hood opening where the test object is located and, because the IR camera is positioned in such manner, without directly shining of light upon or into the camera lens. The hood acts as a housing that contains most of the intense flash.

One-Sided Flash Thermography Technique

If the test object can be accommodated inside the flash hood, then it is located at the hood opening or slightly inside the hood. Otherwise, the part is located slightly outside of the hood opening. A short duration (e.g. 3 msec), intense (12 kJ) flash is triggered using a computer keyboard. The data acquisition is triggered a few seconds before the flash and it continues until the prescribed time. The camera provides a sequence of IR images (or frames) called the data sequence (or digital video) of the part surface taken at the chosen frame rate (e.g. 60 Hz or 60 frames per sec). The intensity (numerical value) of each pixel in the image is function of the surface temperature of the corresponding area on the part at the time of image frame. The flash causes the surface to warm up slightly and the heat starts to dissipate rapidly. The surface cools through thermal radiation, convection and conduction. It is assumed that the heat conduction within the part is the dominant heat transfer mode until the temperature gradients within the part become small. At later times, the heat conduction is of the order of the combined effect of heat convection and radiation. The IR data acquisition and data analysis utilizes the thermal data in the short duration immediately after the flash where the thermal dissipation is dominated by the heat conduction within the part.

The heat exchange across the boundaries due to the convection can be assumed to be zero if the Biot number ($NBi=hL/k$)<0.1. Consider an example of ½ cm thick graphite/epoxy ($k=0.64$ W/mK) plate. Using $h=10$ W/m^2, the Biot number is 0.078. Therefore, the heat conduction is the dominant mode of heat transfer in this example. Thinner parts tend to equalize the temperature within the part very quickly and have relatively longer cooling time by heat loss to environment.

The IR Flash Thermography Anomaly Detection

Figure 2:
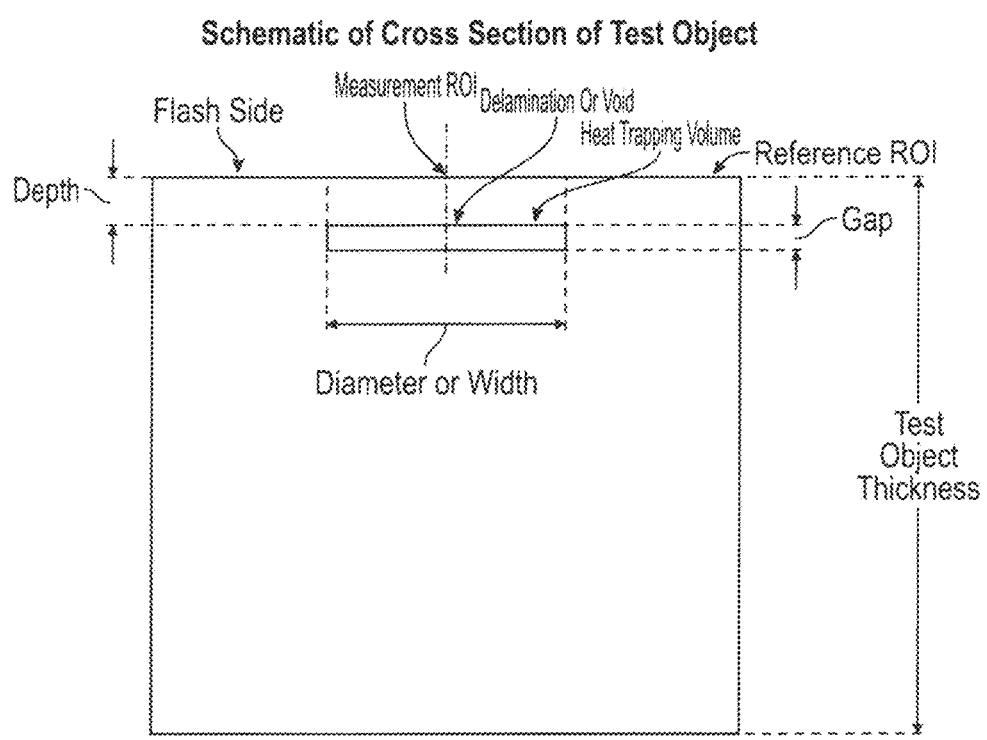
FIG. 2 provides a cross sectional view of a test object, a reference region of interest (ROI), and a measurement ROI.

Assume that the part is a plate made of a thermally isotropic material with constant thickness and it fits inside the hood. The plate is supported at the corners on insulating standoffs and the hood is oriented vertically. If it is assumed that the flash intensity is uniform over the plate top surface, then the heat conduction will be in a direction normal to the part surface in most of the acreage area (area away from edges of the part and flash boundary). The heat is conducted uniformly from the top surface to the bottom surface of the plate. The normal heat conduction will be obstructed by an anomaly such as a small round gapping delamination at the center of a plate, as depicted in FIG. 2. The volume bounded by the anomaly on one side and the part top surface on the other side is called the heat trapping volume.

The top surface area surrounding the anomaly cools faster than the top surface (footprint) area above the anomaly. The IR camera captures the surface temperature image in terms of the pixel intensity and shows the anomaly as a hot spot (e.g. an area warmer than the surrounding area) which is about the size and shape of the anomaly footprint. The relative pixel intensity of the hot spot changes with the time. Deeper anomalies appear at later times in the IR video compared to the near surface anomalies. After the appearance of an anomaly in the IR video, its relative pixel intensity continues to increase with time. The relative pixel intensity of the anomaly reaches a peak at a certain time and then the relative intensity decays until the indication area temperature and the surrounding area temperature become equal. The part continues to cool down to the ambient temperature through heat convection and radiation.

Normalized Contrast

Let us define the normalized image contrast based on the pixel intensity (video raw data gray value) as follows. The contrast is also called the normalized irradiance or the normalized pixel intensity contrast.

$$C^W = \frac{\Delta W - \Delta W_{ref}}{\Delta W + \Delta W_{ref}}, \tag{1}$$

$$\Delta W = W - W^0, \tag{2}$$

$$\Delta W_{ref} = W_{ref} - W_{ref}^0, \tag{3}$$

where,
$C^W$=normalized IR image contrast at time t,
$\Delta W$=change in pixel intensity of measurement ROI after flash,
W=pixel intensity at measurement ROI at post-flash time t,
$W^0$=pixel intensity at measurement ROI before flash,
$\Delta W_{ref}$=change in pixel intensity of reference ROI after flash,
$W_{ref}$=pixel intensity at reference ROI at post-flash time t, and
$W_{ref}^0$=pixel intensity at reference ROI before flash.

The embodiments described herein may include steps of computing video data consistent with equations such as equation 1 and other equations. By consistent it is meant that the computing includes the possibility of terms that are approximate to, proportional to, or that can be derived from the presented equations but do not need to be exactly the same or include the exact same letters, organization, and so forth. This is especially true because it is well known that laws regarding handling of equations allow for well known permutations and so forth. The general method steps of normalized contrast video processing in accord with embodiments described herein are shown in FIG. 6.

Figure 6:
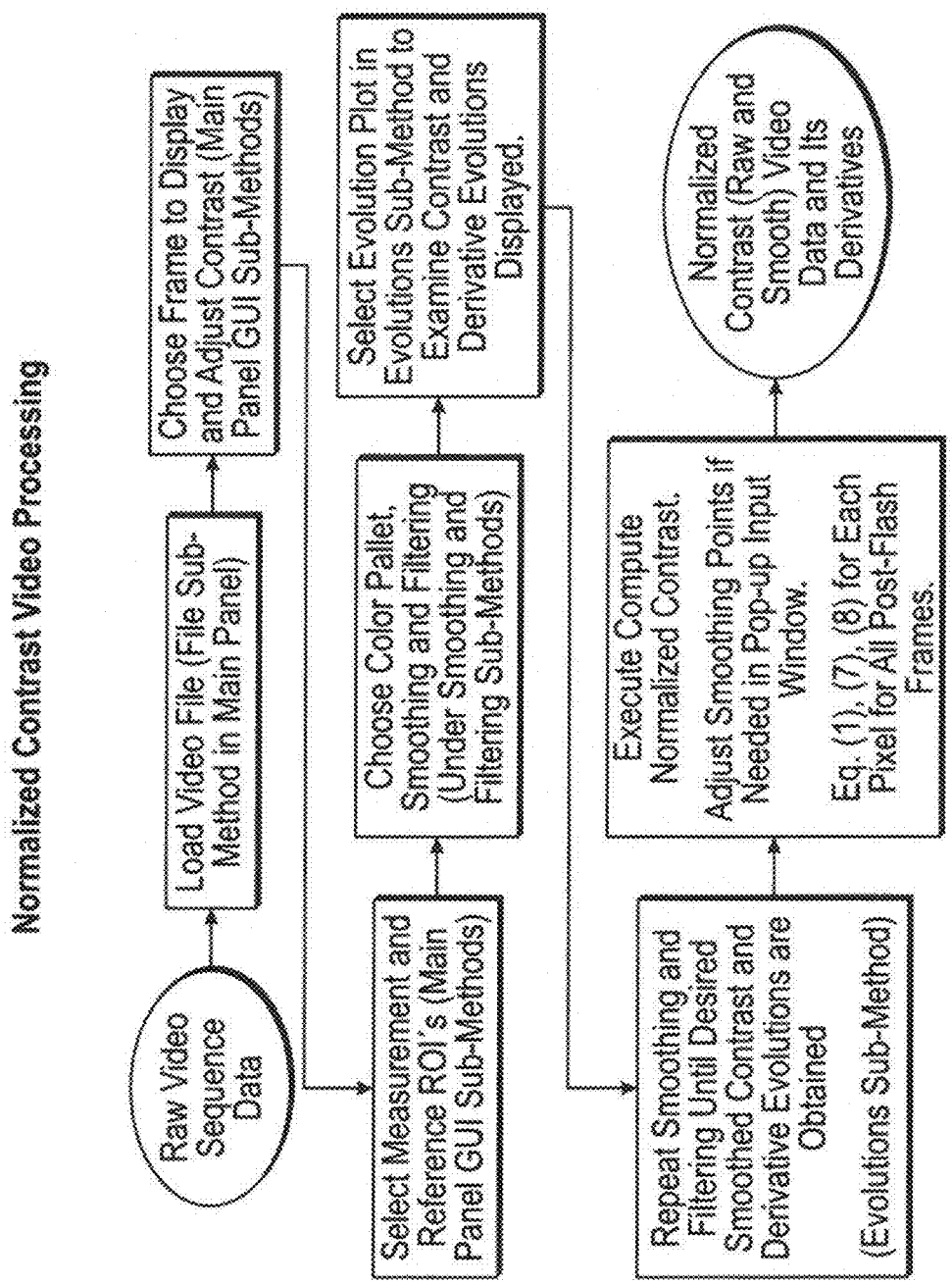
FIG. 6 shows a flowchart of Normalized Contrast Video Processing in accord with one embodiment described herein.
Figure 7:
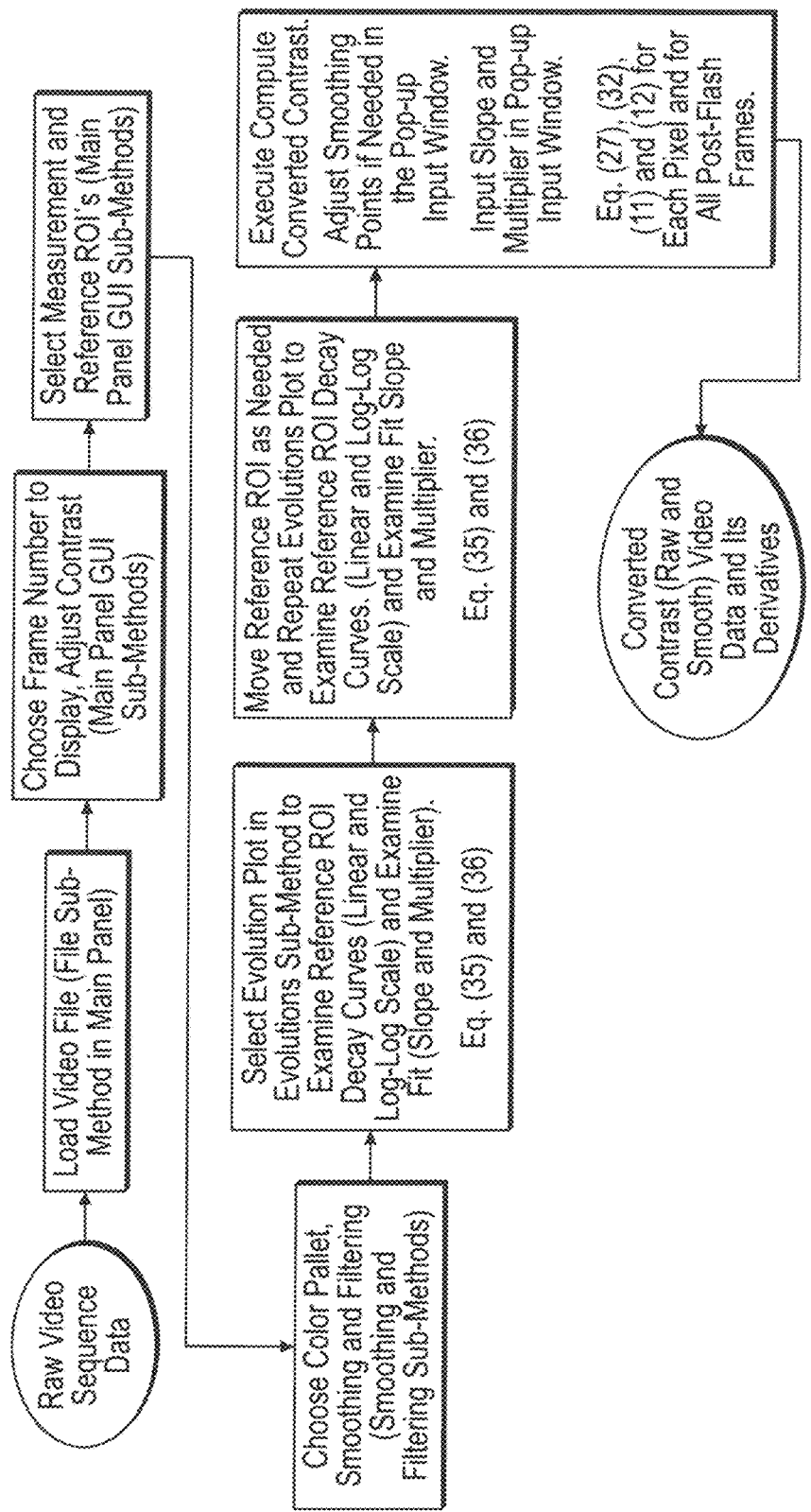
FIG. 7 shows a flowchart of Converted Contrast Video Processing in accord with one embodiment described herein.

FIG. 12 shows an example of contrast evolution video data extracted at a selected measurant ROI and reference ROI produced in accord with the method shown in FIG. 6. The pixel intensity (raw gray value) starts below line "Y-Pos 29 34." The first column of the column is frame time t in seconds, the second column is the pixel intensity of measurement ROI and the third column is pixel intensity of the reference ROI. Normalized contrast is computed for every pixel in the normalized contrast and derivatives (NCD) method and typically for all frames subsequent to the flash of heat using above equations.

Figure 9:
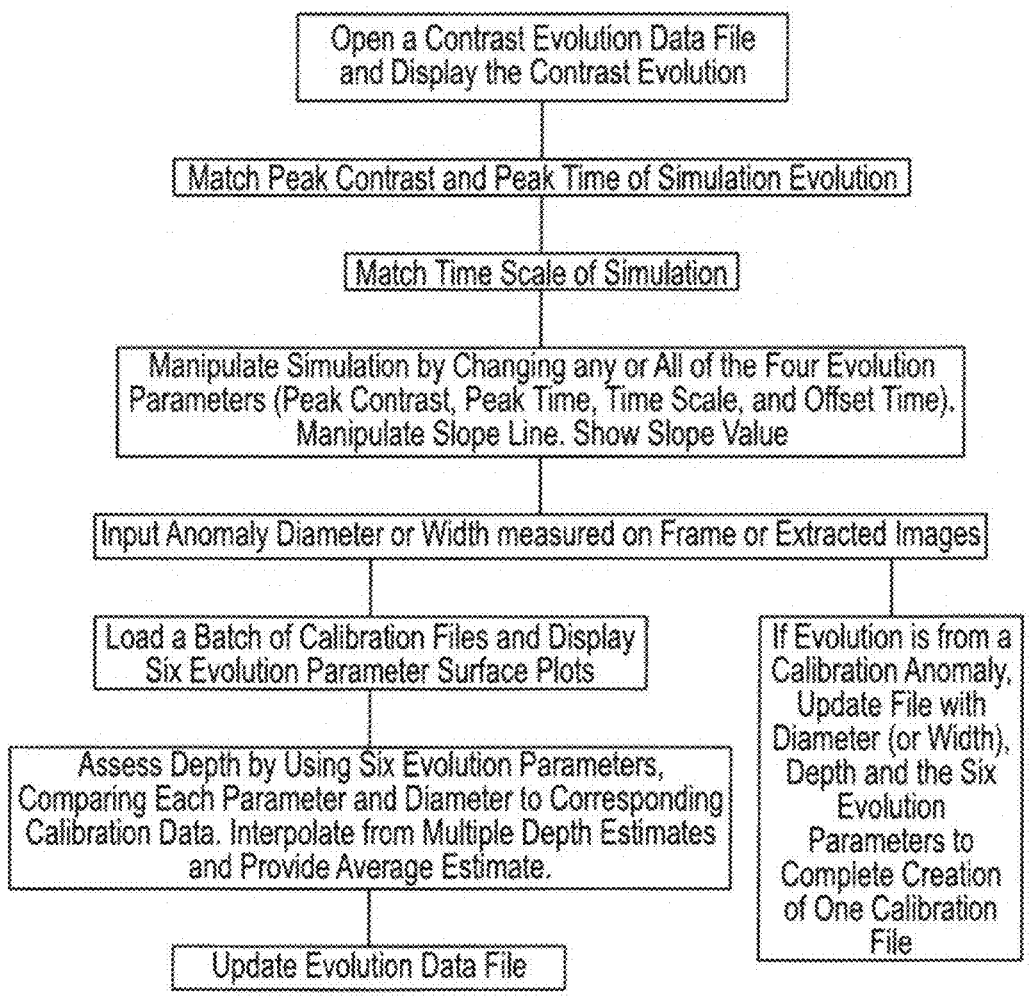
FIG. 9 provides various sub-methods in Anomaly Depth Analysis method in accord with one embodiment described herein.
Figure 10:
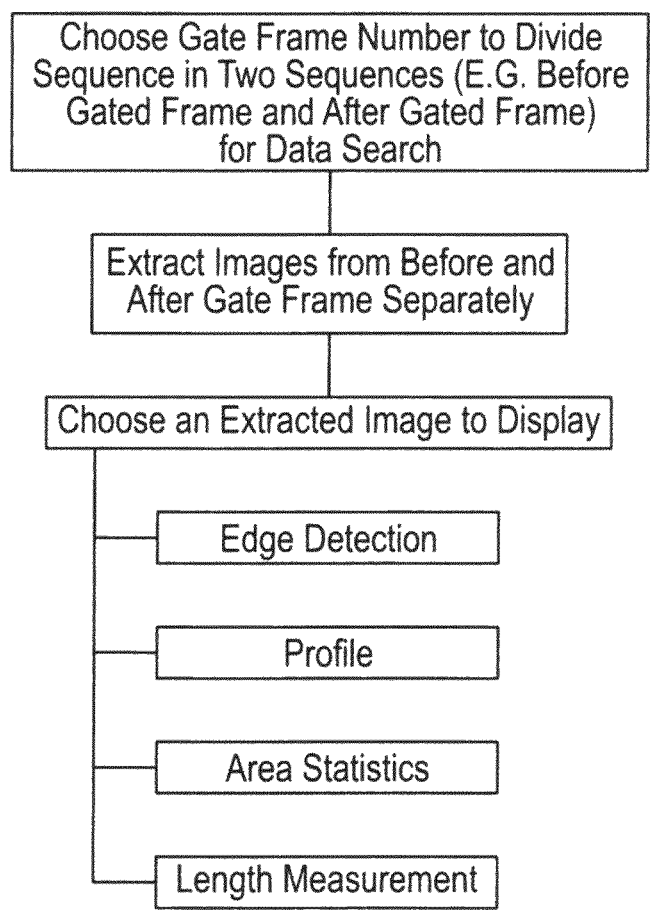
FIG. 10 shows Extracted Images Processing Steps after computing any of the three forms of Processed Data from FIG. 6-9 in accord with one embodiment described herein.
Figure 11:
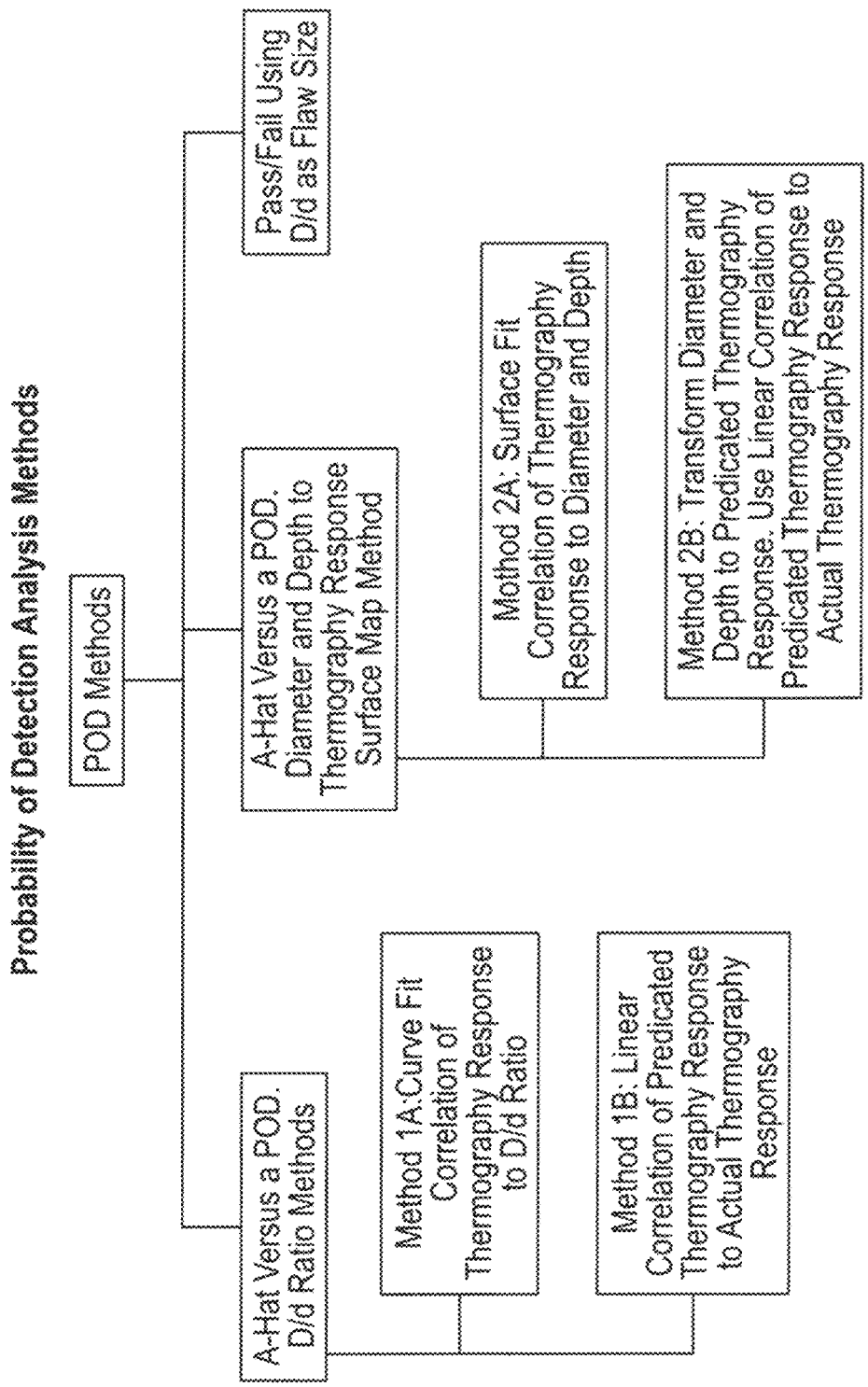
FIG. 11 shows a flowchart of various Probability of Detection Analysis methods in accord with one embodiment described herein.

Values in line "Diameter (in.)=0.0000, Depth (in.)=1.0000, Peak=0.0000, Peak Time (s)=0.0000, Scale Factor=1.0000, Offset=0.0000, Begin Time=0.0000, Slope=1.0000" are updated after analyzing the contrast evolution in CECA method, which is generally shown in FIG. 9.

Let us also define normalized temperature contrast based on converting the pixel intensity (raw data gray value) to temperature as follows.

$$C^T = \frac{\Delta T - \Delta T_{ref}}{\Delta T + \Delta T_{ref}}, \tag{4}$$

$$\Delta T = T - T^0, \tag{5}$$

$$\Delta T_{ref} = T_{ref} - T_{ref}^0, \tag{6}$$

where,
$C^T$=normalized IR image temperature contrast at time t,
$\Delta T$=change in pixel temperature of measurement ROI after the flash,
T=pixel temperature at measurement ROI at post-flash time t,
$T^0$=pixel temperature at measurement ROI before the flash,
$\Delta T_{ref}$=change in the pixel temperature of reference ROI after flash,
$T_{ref}$=pixel temperature at reference ROI a post-flash time t, and
$T_{ref}^0$=pixel temperature at reference ROI before flash.

Figure 8:
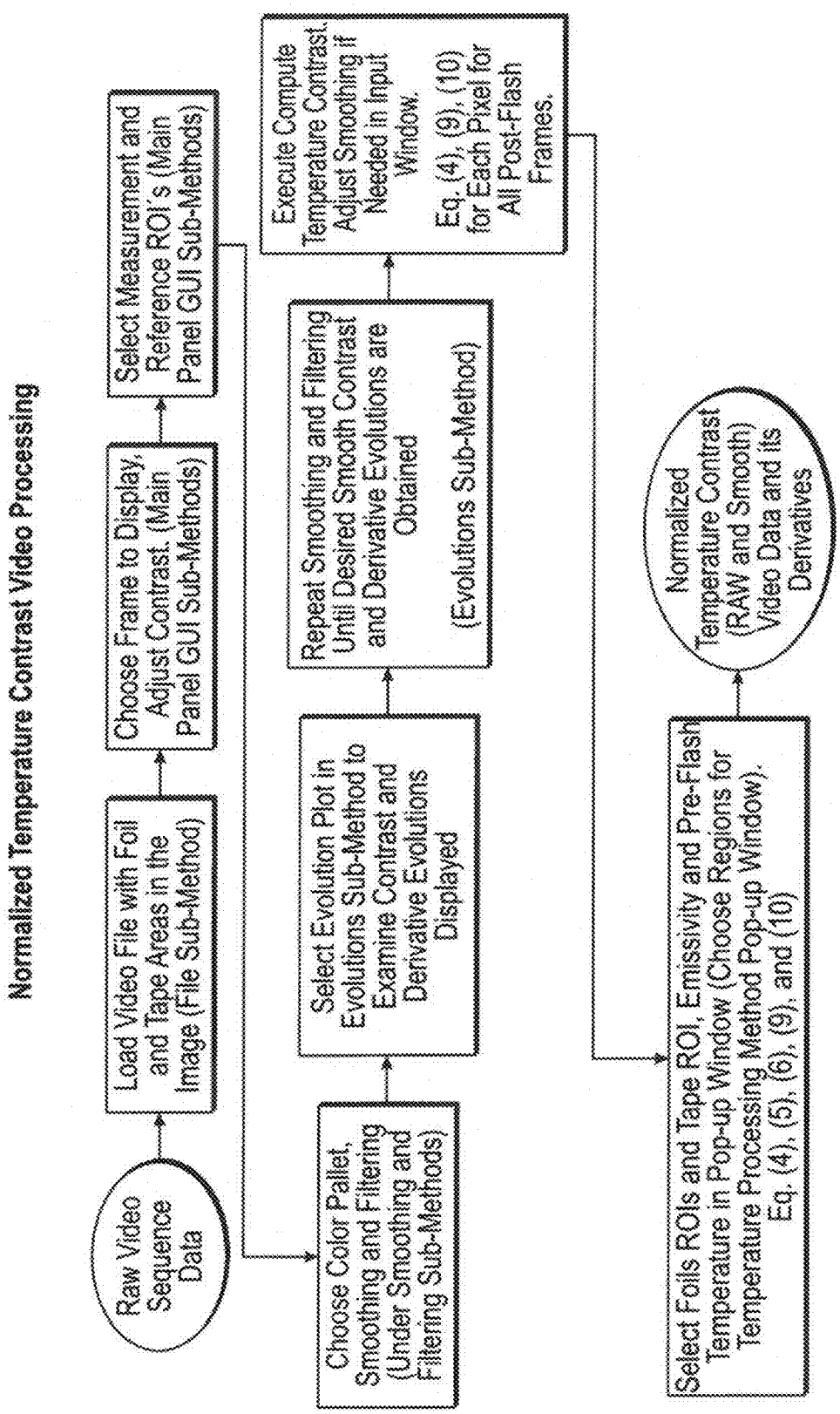
FIG. 8 provides various sub-methods in Anomaly Depth Analysis method in accord with one embodiment described herein.

The normalized temperature contrast is computed for every pixel in normalized temperature contrast and derivatives (TCD) method using above equations as indicated in FIG. 8.

The definition of Converted Contrast $C^C$ is covered separately.

Use of a reference test piece alongside the test object, both appearing in the field of view of camera, helps in the three contrast video image processing (CVIP) methods where monitoring of thermography response is desired. Here, the reference ROI can be chosen on the anomaly-free area of the reference test piece. Also, if a programmed flaw exists in the reference test piece, the thermography response from the reference flaw can be used in monitoring thermography response.

Derivative Based Imaging Approaches

The embodiments described herein utilize first and second time derivatives of the Normalized Image Contrast (sometimes referred to herein as Normalized Contrast, Normalized IR image contrast, and the like herein). As well, first and second time derivatives of the normalized temperature contrast and converted contrast are disclosed.

Normalized Image Contrast 1st (order) time derivative is given by, $$C^{W\prime}=dC^W/dt \tag{7}$$

Normalized Image Contrast 2nd (order) time derivative is given by, $$C^{W\prime\prime}=dC^{W\prime}/dt \tag{8}$$

Normalized Temperature Contrast 1st derivative is given by, $$C^{T\prime}=dC^T/dt \tag{9}$$

Normalized Temperature Contrast 2nd derivative is given by, $$C^{T\prime\prime}=dC^{T\prime}/dt \quad (10)$$

Converted Contrast 1st derivative is given by, $$C^{C\prime}=dC^{C}/dt \quad (11)$$

Converted Contrast 2nd derivative is given by, $$C^{C\prime\prime}=dC^{C\prime}/dt \quad (12)$$

Any of the three Contrast formats 1st derivative is given by, $$C\prime=dC/dt \quad (13)$$

Any of the three Contrast formats 2nd derivative is given by, $$C\prime\prime=dC\prime/dt \quad (14)$$

Where,
t=time corresponding the video frames.

These derivatives are computed for a plurality of frames and preferably computed for each relevant pixel in each frame of the contrast video generating derivative videos or at least for a plurality of frames.

Here, we define two different methods of computing the 1st derivatives.

Method 1A: The first method involves derivative of the raw contrast evolution data with smoothing during the calculation of derivatives.

Method 1B: Alternatively, the first method involves derivative of the smoothed contrast evolution data using the smoothing during the calculation of derivatives.

Method 2A: The variation of second method involves derivative of the curve fit (non-simulation or empirical) to contrast evolution which may be fitted to either raw or smooth data. The first derivative $C^{f\prime}=dC^{f}/dt$ and second derivative $C^{f\prime\prime}=dC^{f\prime}/dt$ are computed from the empirical curve fit equations $C^{f}=f(t)$. Example of empirical fit equation is given in eq. (41). Another example is given in FIG. 16.

Method 2B: Another variation of the second method involves derivative of the simulation fit to contrast evolution which may be fitted to either raw or smooth data. The simulation fit is also a curve fit (e.g. polynomial fit) in the contrast simulation (US Koshti, U.S. Pat. No. 8,577,120 B1). The derivatives are computed from the simulation curve fit equations. The first derivative $C^{f\prime}=dC^{f}/dt$ and second derivative $C^{f\prime\prime}=dC^{f\prime}/dt$ are computed from the simulation curve fit equations $C^{f}=f(t)$.

There are advantages as well as disadvantages for each method. The simulation fit and the non-simulation curve fit methods require that the curve fit is established. If the fits cannot be established accurately due to non-ideal test conditions, low contrast value, choice of fit model etc., then the results would be in error. However, the derivatives are calculated from the fit function equations and therefore the resolution is excellent compared to the routines that use smoothed contrast data and/or excessive smoothing to calculate derivatives. The smooth derivatives depend upon the length of the smoothing span (points or number of frames). Longer smoothing span provides better suppression of the pixel temporal noise but it also flattens the contrast evolution and reduces the time resolution. Depending upon the algorithm used, beginning portion of the evolution shows more effect of the smoothing span, which may be used to your advantage in some situations.

Raw Contrast and Smooth Contrast Derivatives
Method 1A

Figure 3:
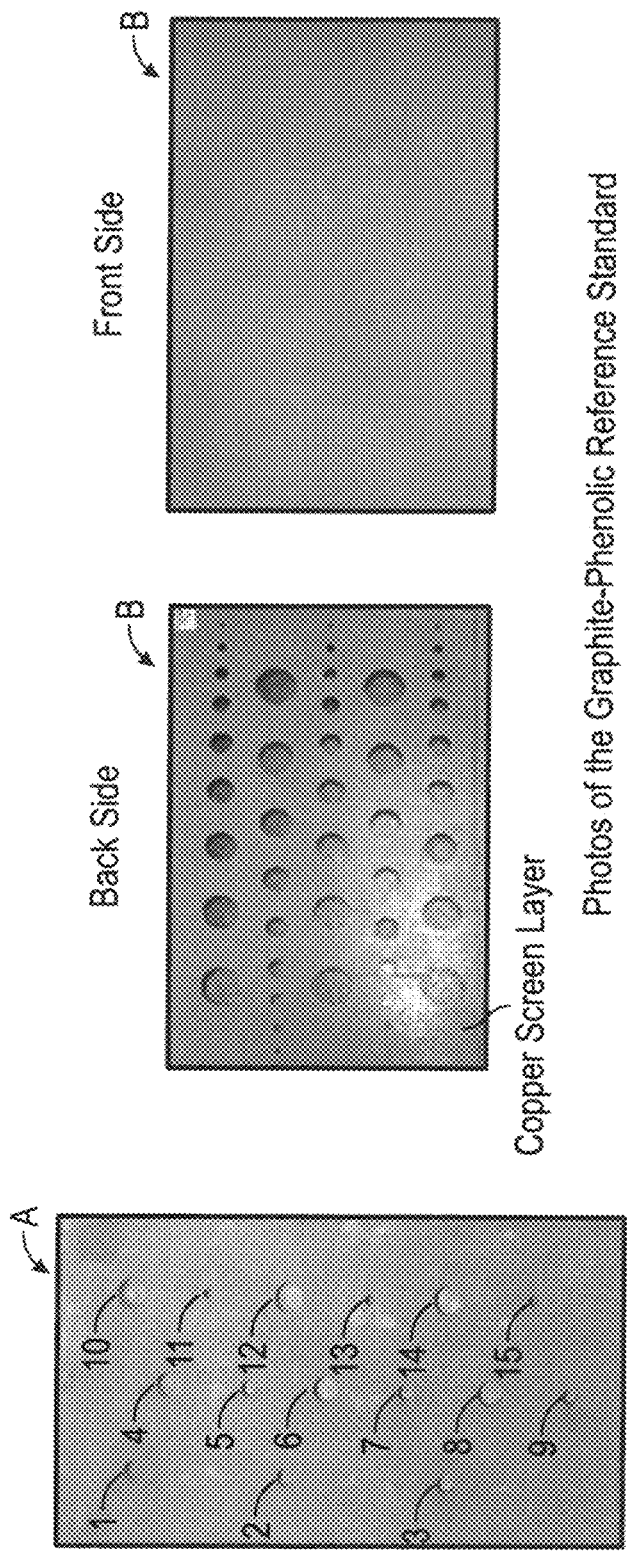
FIG. 3 provides pictures of reinforced carbon-carbon specimen A and graphite-phenolic calibration standard B.

In order to illustrate this method, a test plate with back drilled flat bottom holes is used in the IR flash thermography data acquisition. FIG. 3 shows of a photo of one possible non-limiting embodiment for test plate specimens A and B. In the non-limiting specimen A, all holes are drilled to the same depth. There are five sizes of the diameter and three holes for each size. Thus, there are five groups of three identical holes. Group 1: hole # 11, 13 and 15. Group 2: hole # 5, 7 and 9. Group 3: Hole # 4, 6, and 8. Group 5: Hole # 10, 12 and 14. The hole diameter increases from group 1 to group 5. Plate specimen B has five depths and 9 diameters. Holes in each row have same depth. See FIG. 4 for depths and diameters of specimen B from FIG. 3.

IR flash thermography is performed on the front side of the plate. The reference region of interest (ROI) is chosen near hole number 4 for specimen A. The ROI size is 5×5 pixels. The reference ROI can be chosen on a separate plate of the same material that is kept next to the part and imaged concurrently with the part. The reference plate can be thicker or of the same thickness and no flaws should be present in the reference plate. Ideally, the reference ROI is never warmer than acreage area of the part.

Figure 13:
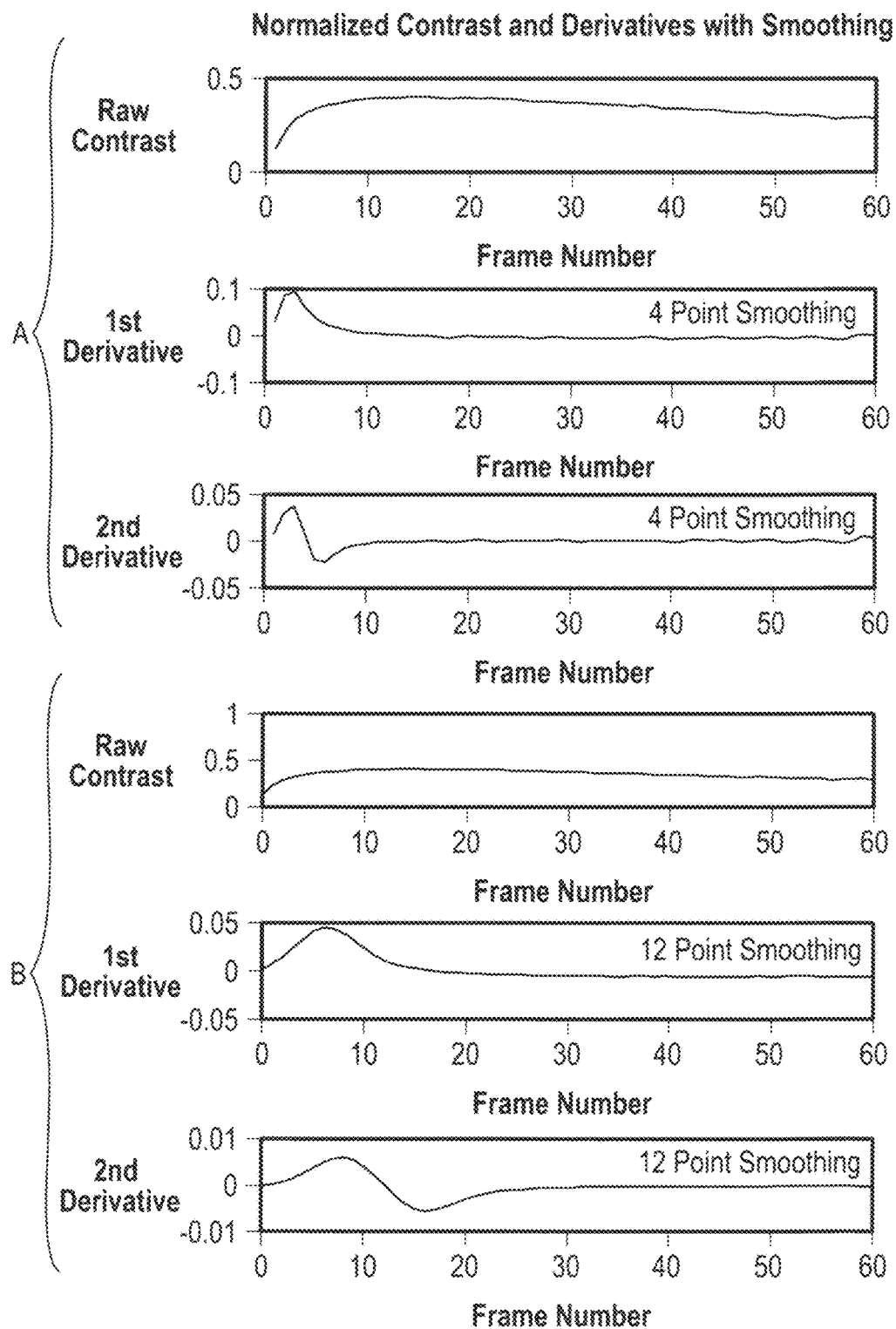
FIG. 13 shows examples of raw Normalized Contrast and smooth (or processed) derivative evolutions for hole number 4 of Specimen A with two values of smoothing points for comparison in accord with one embodiment described herein.

FIG. 13 shows the raw normalized contrast and the smooth derivative evolutions for hole number 4 as an example. Two smoothing levels, i.e., four point smoothing and the twelve point smoothing were used in the derivative images to illustrate the differences in the results. Longer smoothing span moves the location of the peak in the first derivative to the right. The peaks in the contrast derivatives are with twelve point smoothing are shifted further to the right compared to those with four point smoothing. The twelve point smoothing derivative evolutions are smoother (less high frequency components) but flatter (less amplitude) than the four point smoothing derivative evolutions.

A number of derivative based images can be obtained. First, we create the Normalized contrast video sequence data (C), the contrast first derivative data sequence (C') and the contrast second derivative data sequence (C"). We count the first postflash frame as frame 1. We can play video of the three data sequences and select any frame that provides the desired image of the feature being detected. These contrast evolutions (C) are considered to be equivalent to the A-scan of pulse/echo technique of ultrasonic testing and are called the contrast A-scans here. See FIG. 13.

In addition, several Extracted Images are possible as follows. The contrast evolution has a peak that can be reliably located by choosing a correct time gate (window). This provides two possibilities for the contrast feature images i.e. peak contrast and frame number at peak contrast. The first derivative has a forward shifted peak due to smoothing. This provides two possibilities for the contrast feature images i.e. peak first derivative of contrast and the frame number of peak first derivative of contrast. The second derivative has a peak and a dip associated with the peak of first derivative. This provides many possibilities for the contrast feature images i.e. peak of contrast second derivative, frame number of peak of second derivative of contrast, minimum of second derivative of contrast and frame number of minimum of second derivative of contrast. In addition, we can combine (e.g. add, subtract, multiply and divide) these images to create new images. These images are designed so that the anomaly data comes from raw data frames close to the peak time. Earlier time images with time close to t50L (time at which contrast value is 50% of the peak value) and time that is less than the peak time ($t_{peak}$) provide better sizing. Images beyond $t^{peak}$ provide footprints that are larger than the size of the actual anomaly. Moreover, a desirable combination of images may suppress both spatial and temporal noise. Let us look at some derivative based images. Various images are shown below to illustrate the method of contrast based feature scans. Unless, mentioned, the time gate of frame 1 through frame 60 was used in the following images. The time gate can be used to choose section of the image frame for analysis, e.g., images preceding time gate, images after time gate or images between two time gates.

Various uses could include, for example only, a normalized contrast (C8), corresponding first derivative (C'8), and corresponding second derivative (C"8) at frame 8 or an average normalized contrast ($C_{av}$), average of first derivative of normalized contrast ($C'_{av}$), and average of second derivative of normalized contrast ($C''_{av}$) from frame numbers 8, 9 and 10. The time or frame gate can be established from frame 8 through 10. In this example, all such images would show anomalies i.e. anomalies, but visible contrast decreases with the derivatives due to reduction in amplitude of the corresponding evolutions. The values may be amplified appropriately by choosing different set of frame images.

Figure 14:
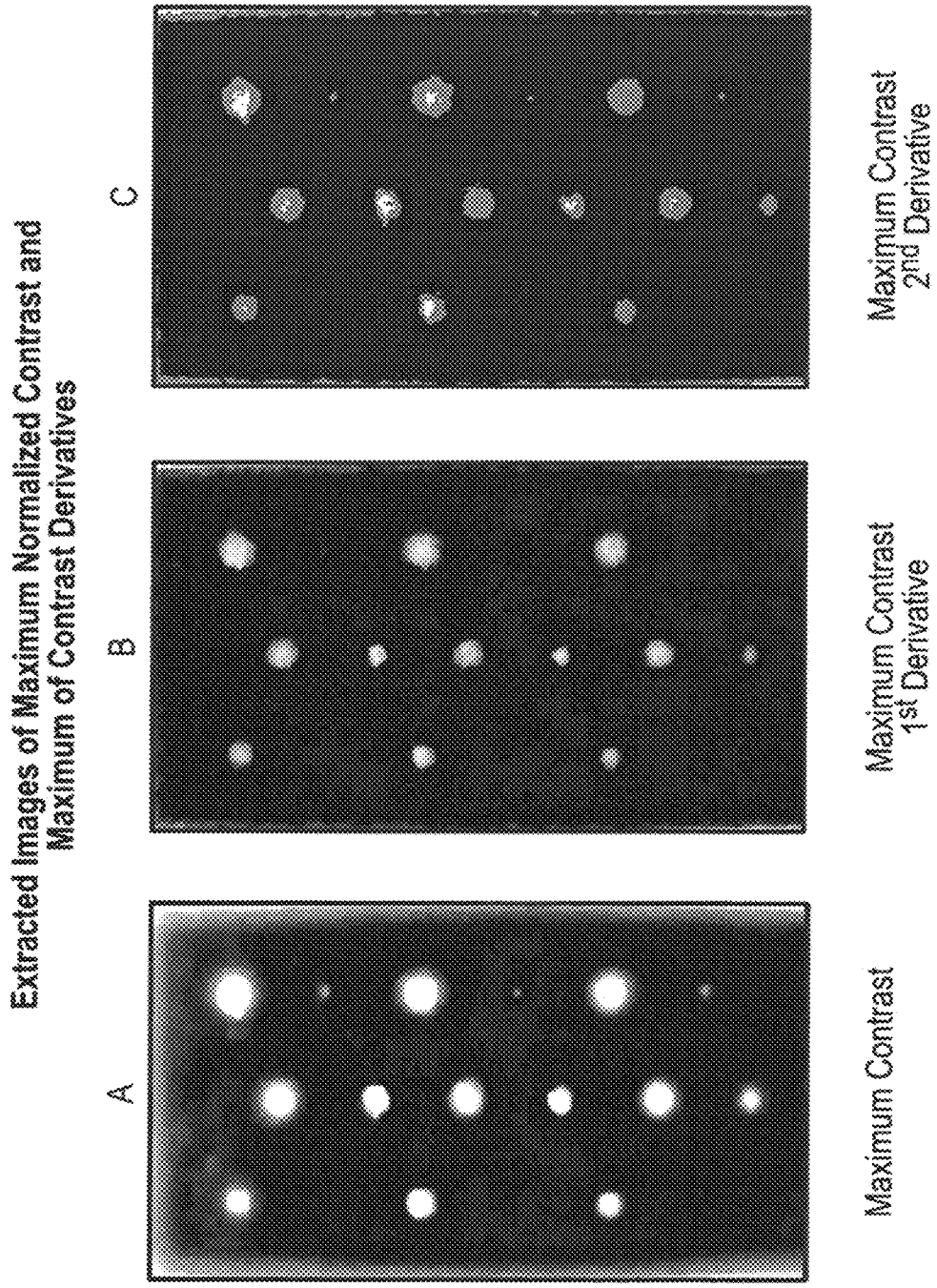
FIG. 14 shows Extracted Images of peak Normalized Contrast (Cmax), peak first derivative of the Normalized Contrast (C'max), peak and second derivative of Normalized Contrast (C"max) in accord with one embodiment.

As another example, FIG. 14 shows peak normalized contrast ($C_{max}$), peak of the first derivative of the contrast ($C'_{max}$), and peak of the second derivative of the contrast ($C''_{max}$). All images show the anomalies. These images are considered to be similar to the ultrasonic C-scan amplitude images and are called the contrast value C-scans.

Another possibility is to show the frame number of the peak contrast ($nC_{max}$). This image is useful in assessing relative depth of the anomaly. This image is considered to be similar to the time-of-flight ultrasonic C-scan and is called the contrast time of flight C-scan.

Another possibility is to show a comparison of peak the first derivative (C-scan) with different smoothing points. Twelve point smoothing provides a less grainy image.

Another possibility is to show comparison of peak the second derivative (C-scan) with different smoothing points. Twelve point smoothing provides a less grainy image. This would show clear detection of holes with numbers 11, 13 and 15.

Another possibility is to show an image of the peak product time (C-scan).

Another possibility is to show images of the product of the peak contrast with peak first derivative of the contrast (C-scan). Higher point smoothing provides a smoother and sharper image.

Another possibility is to show a (C-scan) image created by subtracting the minimum of contrast from the peak contrast.

Another possibility is to show (C-scan) images created by subtracting the minimum of first derivative of contrast from the peak of first derivative of contrast. Higher point smoothing provides a smoother and sharper image.

Yet another possibility is to show (C-scan) images created by subtracting the minimum of second derivative of contrast from the peak of second derivative of contrast. Higher point smoothing provides better visible contrast.

Yet another possibility shows (C-scan) images of a product of three quantities, i.e., the peak contrast, the peak of first derivative of contrast and the peak of second derivative of contrast. Higher point smoothing provides a smoother and sharper image although holes 11, 13 and 15 would not be detected in this example.

Yet another possibility is to show (C-Scan) images of a product of three quantities i.e. the peak of second derivative of contrast, the peak of first derivative of contrast and the negative of the minimum of second derivative of contrast. Higher point smoothing provides a smoother and sharper image although holes 11, 13 and 15 are not detected.

Smooth Contrast and Smooth Contrast Derivatives Method 1B

The contrast evolutions can be smoothed using low-pass filtering to convert the contrast video sequence data to the smoothed (filtered) contrast video sequence data.

One example of this is to show a smooth contrast and the smooth derivative (A-scan) evolutions for the region of interest at hole number 4. Images can be created that are derived from the smoothed contrast video sequence data.

Another possibility is to show the peak contrast (Csmooth,max), the peak of first derivative of contrast (C'smooth,max), the peak of second derivative of contrast (C"smooth,max) images. Normalized contrast and the first derivative images in this example would show all anomalies. These images are considered to be similar to the ultrasonic C-scan amplitude images and called the contrast (value) C-scan images.

Another possibility is to show an image the frame number of the peak contrast (nCsmooth,max). This image is useful in assessing relative depth of the anomaly. Another possibility is to show an image from the frame number with the peak contrast. The peak contrast frame number in areas where no anomalies exist may not be desirable as peak contrast value is low. Therefore, peak contrast threshold of 0.1 could be chosen. One image could show a binary (value 1 or 0) image of peak contrast above 0.1. The binary peak contrast image is multiplied with peak contrast frame number image to provide a threshold modified image that shows the peak contrast frame number above a peak contrast threshold of 0.1. These images are considered to be similar to the ultrasonic C-scans.

Another possibility is to show a frame number of peak contrast of first derivative (nC'smooth,max) image. This image is useful in assessing relative depth of the anomaly. This image is considered to be similar to time-of-flight ultrasonic C-scan and is called contrast time C-scan here. Determining frame numbers with the peak contrast for areas where no anomaly exists is not of much value as the amplitude of the contrast evolution is low and derivatives can be dominated by the temporal noise which is higher for later frames due to decay of pixel intensity.

Yet another possibility is to show the image in the frame number of the minimum of contrast first derivative (nC'smooth,min) image. This image is useful in assessing relative depth of the anomaly. This image is considered to be similar to time-of-flight ultrasonic C-scan and is called contrast time C-scan here.

Another possibility is to show a minimum contrast of the second derivative (C"smooth,min) image. This image is useful in assessing relative depth of the anomaly. This image is considered to be similar to the ultrasonic amplitude C-scan.

Yet another possibility is to show a peak product time (C-scan) which is useful in assessing the anomaly gap thickness.

Yet another possibility is to show an image of a combined (C-scan) image calculated by multiplying peak contrast by peak of first derivative of contrast. The image shows that all holes and background noise is reduced.

Another possibility is to show an image with a combined (C-scan) image calculated by subtracting minimum of contrast from peak contrast. The image shows all holes but has speckled background noise.

Yet another possibility is to show a combined (C-scan) image calculated by subtracting minimum of first derivative of contrast from peak first derivative of contrast. The image shows all holes but has speckled background noise that makes detection of the smallest hole difficult.

Yet another possibility is to show a combined (C-scan) image calculated by subtracting the minimum of second derivative of contrast from the peak of second derivative of contrast. The image would show all holes but has speckled background noise that makes detection of the smallest hole difficult.

Another image that could be generated would show a combined (C-scan) image calculated by multiplying the peak contrast, the peak of first derivative of contrast and the peak of second derivative of contrast. In this example for the above described calibration standard would show all but the smallest three holes but has very little background noise.

As another example, an image may be produced that shows a combined (C-scan) image calculated by multiplying the peak of second derivative of contrast, negative of the minimum of second derivative of contrast and the peak of first derivative of contrast. The image would again show all but the smallest three holes but has very little background noise.

As another possibility, images could be generated that show normalized contrast images of peak contrast, standard deviation of peak of normalized contrast, peak of normalized contrast first derivative, and peak of normalized contrast first derivative frame number (Time of Flight C-Scan). Standard deviation is measure of noise in the data and is used to compute signal-to-noise ratio.

Figure 15:
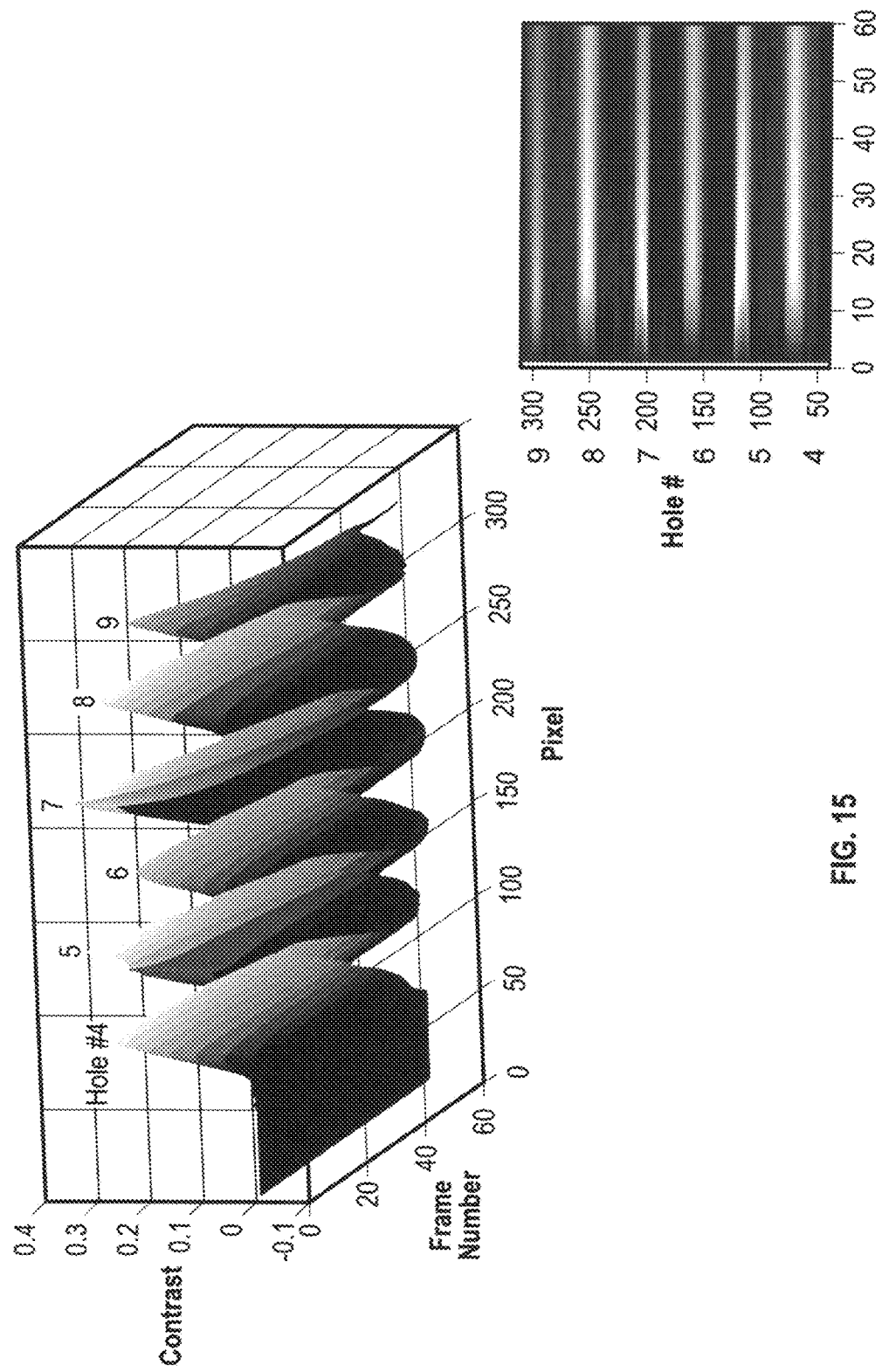
FIG. 15 shows Normalized Contrast evolutions as B-scan along a vertical line through holes with numbers 4 to 9 of specimen A in accord with one embodiment.

FIG. 15 shows the normalized contrast evolutions along a vertical line through holes 4 through 9 for the calibration standard discussed above. (See also B-scan with vertical line in FIG. 20.) The left image is in perspective view and the right image is a planer image. The contrast evolutions along a pixel line have been stacked or graphically presented on a sequential manner. The staked contrast (or derivative) evolution display is considered to be equivalent to the B-scan image of the ultrasonic pulse echo scanning technique and is called the contrast B-scan here. The images can be constructed from the derivative contrast sequences also.

Fitted Contrast and Fitted Contrast Derivatives
Method 2

Figure 16:
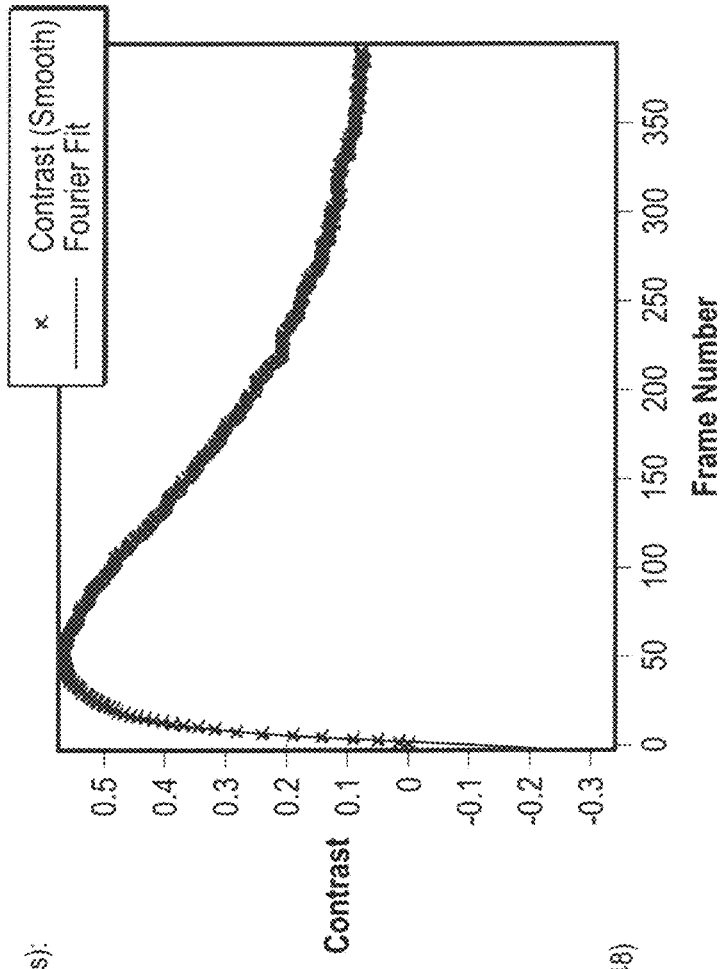
FIG. 16 shows an example of curve fit to Normalized Contrast evolution, including curve fit equation, fit data and a plot of curve fit equation for each frame number in accord with one embodiment.

In the second method, we choose either a raw or smooth contrast evolution for the curve fit. For example, one possible image would show a raw contrast evolution and a five point (span) smoothing of the evolution. Next a suitable curve fit model is chosen (e.g. exponential, Fourier, polynomial etc.) and the curve fit is established. FIG. 16 shows the curve fit equation, the fit data and the plot of the curve fit equation for each frame number obtained by the curve fit to the smooth contrast data. Note that the curve fit extended into the negative values for early frames. The raw data does not have negative values. The contrast evolution data is replaced by the curve fit coefficients (18 in this case) in this method. Next the derivatives equations are written by taking derivatives of the curve-fit equations. Using the derivative equations, the derivatives are preferably computed for all frame numbers of interest using an appropriate computer application (e.g. MatLab).

Figure 17:
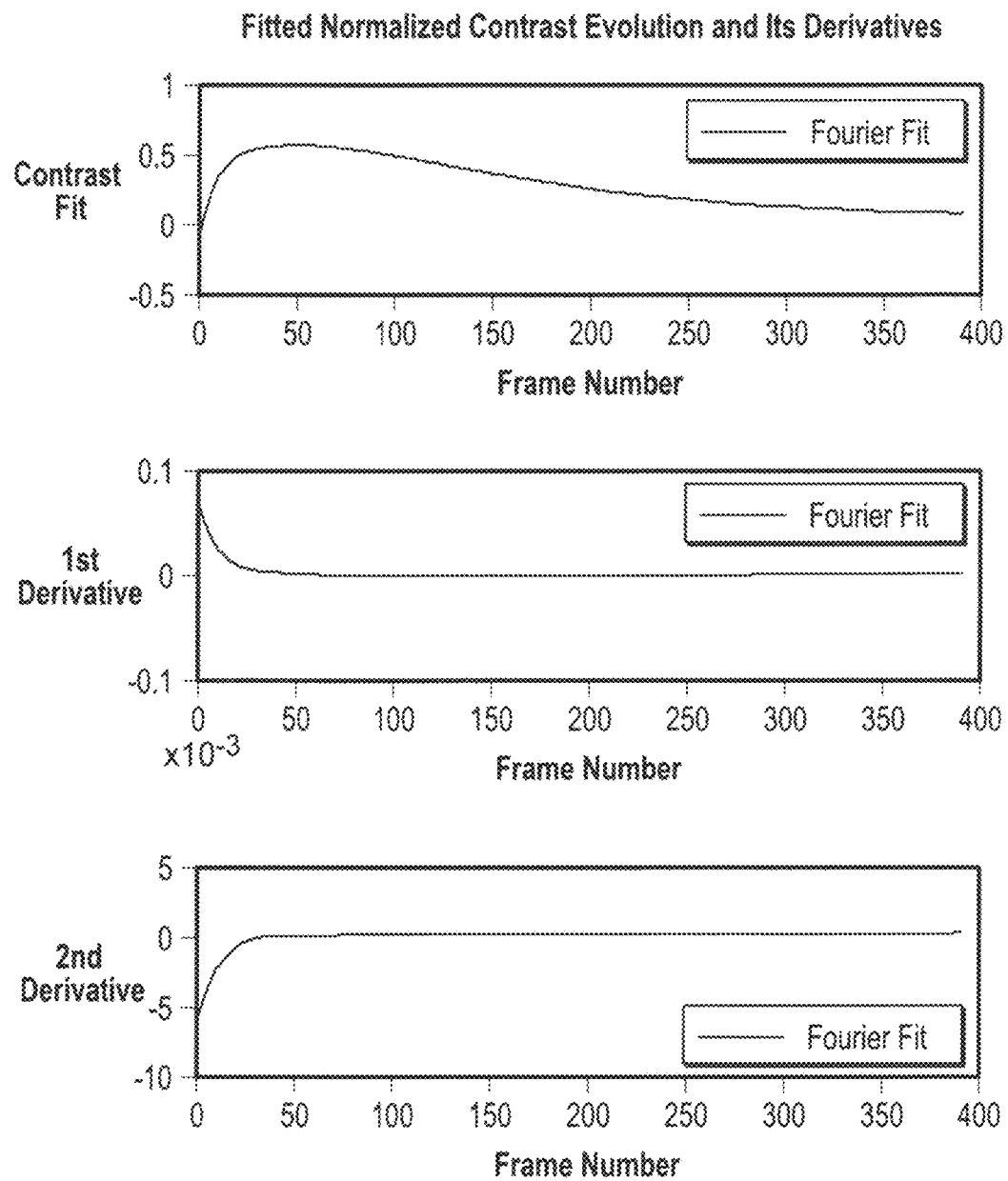
FIG. 17 shows an example of fitted Normalized Contrast evolution and its derivatives in accord with one embodiment.

FIG. 17 shows the derivative evolutions of the fitted normalized contrast evolution. The process is preferably repeated for each pixel of the normalized contrast evolution, e.g., for a plurality of frames, preferably all frames. The first derivative shows the peak of in the first frame and the second derivative shows a minimum in the first frame which is different than would be the derivatives of method 1. The peaking in the first frame is due to the smooth extension of the curve fit (without inflection) to the first frame. However, depending upon the curve fit, the frame rate and depth of the flaw, the curse fit may have an inflection point before the peak time. In such situations, a dip or low in the first derivative could be observed. As another example, a fitted normalized contrast evolution with peaks in the derivatives can be produced which may show the contrast fit, the $1^{st}$ derivative and the second derivative.

The image of the peak of second derivative of contrast, negative of the minimum of second derivative of contrast and the peak of first derivative of contrast, discussed above, would show a contrast fit with the early inflection and its derivatives which indicate early dip in derivatives and similarity in shape characteristics to the method 1 derivatives. In this situation, all images defined for method 1 are applicable. In case the derivatives do not show the initial dip, then the derivative images can be established at peaks of and minimums of contrast and its derivatives. In addition, frame number images at selected times (e.g. t50L, tpeak, t50R) can be plotted. All method 2 images are also classified as the contrast A, B and C-scan images.

Converted Contrast Computation

A basis is for converted contrast. Consider a very thick plate of a thermally isotropic material. The material has uniform, density, specific heat and thermal conductivity. It has a smooth surface (better than 63 rms) and uniform and high emissivity (>0.8). Before exposure to light flash, the plate is also at equilibrium temperature with the surroundings which is at constant temperature. When this plate is exposed to an intense light flash (i.e. a short duration heat pulse), the resulting temperature rise is given by, $$\Delta T(t) = \frac{\varepsilon Q}{\beta \sqrt{\pi t}}, t > 0 \quad (15)$$

where, $$\beta = \sqrt{k\rho c}, \quad (16)$$

$$H = \frac{Q}{\Delta t}, \quad (17)$$

where,
ΔT=temperature change from pre-flash temperature on front surface (° C., K or ° F.),
t=time (sec) measured after flash, flash time is zero and is not part of the equation.
β=thermal effusivity of layer above the anomaly, (cai-cm$^2$-° C.1-sec$^{-1/2}$, kcal-m$^{-2}$-K$^{-1}$-sec$^{-1/2}$ or BTU-ft$^{-2}$-° F.$^{-1}$-hr$^{1/2}$),
c=specific heat (cal-gm$^{-1}$-° C.$^{-1}$, kcal-kg$^{-1}$-K$^{-1}$ or BTU-lbm$^{-1}$-° F.$^{-1}$),
ε=emissivity of the flashed surface,
Δt=flash time (sec),
H=average heat flux incident on the surface (cal-cm$^{-2}$ sec$^{-1}$, kcal-m$^{-2}$sec$^{-1}$ or BTU-ft$^{-2}$hr$^{-1}$), Q=total heat incident on the test object per unit surface area (cal-cm$^{-2}$, kcal-m$^{-2}$ or BTU-ft$^{-2}$), k=thermal conductivity, (cal-cm$^{-1}$-° C.$^{-1}$sec$^{-1}$, kcal-m$^{-1}$-K$^{-1}$ sec$^{-1}$ or BTU-ft$^{-1}$-° F.$^{-1}$hr$^{-1}$), ρ=material density (g-cm$^{-3}$, kg-m$^{-3}$ or lbm-ft$^{-3}$).

The above equation assumes that the surface temperature is affected solely by diffusion of heat within the test object by conduction. Heat conduction at the center point is assumed to be in a direction normal to the top surface. Flash from the photographic flash lamps is assumed to be an approximation of an instantaneous heat pulse.

The above equation is not valid during the flash duration. Although most of flash energy of is expended within the selected flash duration setting (e.g. 3 msec), some afterglow decay may linger in first couple of frames (~15-30 msec). Thus, after decay of the afterglow, the above equation may provide a better match with measured surface temperature.

IR camera, used in flash thermography, typically measures test surface irradiance in terms of the pixel intensity and not surface temperature. The related art of U.S. Pat. Nos. 9,066,028 and 8,577,120 describes how pixel intensity could be converted to surface temperature in flash thermography.

Here, we make an assumption that the part has high emissivity and that pixel intensity is proportional to a fixed power (e.g. a positive integer n=4) of the absolute temperature based on the Stefan Boltzman law.

$$W = \lambda^N \quad (18)$$

$$W^0 = \lambda (T^0)^n \quad (19)$$

Here, λ is the Stefan Boltzman constant. Based on the above assumption, we can derive that change in pixel intensity is proportional to a fixed power of change in surface temperature or vice versa. Let us take derivative of Eq. (18).

$$dW = \lambda n T^{n-1} dT \quad (20)$$

Combining Eq. (18) and Eq. (20) we get, $$\frac{\Delta W}{W} \cong n \frac{\Delta T}{T}, \quad (21)$$

$$\Delta T \cong \frac{T}{nW} \Delta W \quad (22)$$

Combining Eq. (15) with Eq. (22) we get, $$\Delta W \sqrt{t} \cong \frac{\varepsilon Q n}{\beta \sqrt{\pi}} \frac{W}{T}, \quad (23)$$

$$\Delta W \sqrt{t} \cong \frac{\varepsilon Q n}{\beta \sqrt{\pi}} \frac{W^0}{T^0}, \quad (24)$$

On right hand side of Eq. (23), we have quantities that are constant except term W/T. Ratio W/T is not constant during flash and earlier portion of the flash afterglow. Once afterglow has subsided, the ratio W/T is becomes approximately constant with time if it is assumed that very small changes in the temperature occur after the afterglow. Therefore, from Eq. (23), we conclude that in isotropic materials in reference area, $$\Delta W_{ref} \propto \frac{1}{\sqrt{t}}. \quad (25)$$

Therefore, we can rewrite Eq. (25) genetically as, $$\Delta W_{ref} \cong M t^s. \quad (26)$$

where,

M=a multiplier that depends on the highest pixel intensity value which occurs right after flash. It is dependent on incident flash energy Q, emissivity ε and effusivity β according to Eq. (23). If material properties are assumed to be constant from shot to shot on the same part, only incident flash energy Q is likely to vary due to variation in geometric part/flash-hood set-up and variation in the flash energy produced; and s=slope or time exponent. It is property of the material. Based on Eq. (23), for isotropic materials it is close to −0.5.

Based on above observation, the converted contrast method involves an empirically derived transformation or multiplier function f(t), when multiplied to relative pixel intensity of the reference region of interest yields a constant baseline value B.

Definition of the converted contrast is given as, $$C^C = \Delta W f \quad (27)$$

such that the converted contrast at reference region has a constant value B.

$$C_{ref}^C = \Delta W_{ref} f \cong B \quad (28)$$

Therefore, the multiplier functions are chosen so that, $$f \cong \frac{B}{\Delta W_{ref}} \quad (29)$$

Another way to determine the multiplier function is to fit a curve to reference relative pixel intensity, $$f = \frac{B}{F_{\Delta W_{ref}}} \quad (30)$$

where, $F_{\Delta W_{ref}}$=curve fit function to relative intensity of reference pixel. Therefore, Eq. (26) can be written as, $$\Delta W_{ref} \cong F_{W_{ref}} = M t^s \quad (31)$$

Multiplier function in this case is, $$f(t) = \frac{B}{\Delta W_{ref}} = \frac{B t^{-s}}{M} \quad (32)$$

The baseline value, B can be set to approximately 1 or 100. Converted contrast is not considered to be normalized. In computing the converted contrast, relative pixel intensity is multiplied by a function. There is no subtraction or division by a small number. Normalized contrast has subtraction of reference relative pixel intensity and division by small numbers which amplify noise for small contrast values, therefore needing smoothing. Converted contrast computation does not have above factors that add noise during computation.

Using definition of the converted contrast given in Eq. (27), and normalized contrast Eq. (1), a relationship between the two can be rewritten as, $$C^W = \frac{C^c - C^c_{ref}}{C^c + C^c_{ref}} \cong \frac{C^c - B}{C^c + B} \quad (33)$$

$$C^c \cong B \frac{1 + C^W}{1 - C^W} \quad (34)$$

Thus, we can compute normalized contrast from converted contrast and vice versa. Note that the converted contrast computation is much simpler than the normalized contrast and depending upon the multiplier function, the converted contrast can have high values. Higher values are advantageous in manipulating plots. Because computation of the converted contrast introduces some measurement errors (e.g. varying W/T during afterglow), we may have certain advantages and disadvantages.

As evident from the Eq. (33) and (34), shapes of the normalized contrast and the converted contrast are very similar except for short duration immediately after flash. Thus, characteristics of derivatives of normalized contrast and converted contrast are very similar and all normalized contrast imaging and contrast derivative imaging are also applicable to the converted contrast video sequence data and converted contrast derivative imaging.

The reference pixel relative intensity function modeled in Eq. (31) can be determined using the IR raw data video sequence of the part. Choose anomaly-free area of part as reference ROI. Choose a window of frames beyond tail end of the afterglow, beyond texture effects but before early detection time7 corresponding to the bottom surface detection. Plot the reference relative pixel intensity with time in linear and log-log scales. Compute the exponent s as slope of the selected portion of the log-log reference relative pixel intensity plot using following equation preferably from log-log plot.

$$s = \frac{d\ln(\Delta W_{ref})}{d\ln(t)} = \frac{d(\Delta W_{ref})}{dt} \frac{t}{\Delta W_{ref}} \quad (35)$$

The chosen linear portion of the log-log plot for calculating slope s beyond decay of afterglow as visually observed in the plot. Compute the multiplier M using following equation.

$$M = e^{(\ln(\Delta W_{ref}) - s\ln(t))} = \frac{\Delta W_{ref}}{t^s}. \quad (36)$$

Compute many estimates of multiplier M over the selected range of reference relative pixel intensity. Use average of these estimates as the value for multiplier M. Multiplier M is primarily affected by flash intensity. A higher flash energy result in higher M. Higher flash energy reduces noise in the data. Finally, choose value of B. If we choose B=100, then $$C^c = \frac{100(\Delta W)t^{-s}}{M} \quad (37)$$

General equation for converted contrast is, $$C^C = f(\Delta W) = Gt^n(\Delta W) \quad (38)$$

Where,
G=a constant, G may be assumed to be 1.
n=positive fractional number.

EXAMPLE 1

Converted Contrast Method Using f(t)=t0.25

In this example, IR flash thermography is performed on front side of plate specimen 1. Reference region of interest (ROI) is chosen near hole number 4. The ROI size is 5×5 pixels. The function f(t)=t0.25 was chosen in this example. Units of the converted contrast in this situation would be pixel intensity gray value multiplied by sec0.25.

Figure 18:
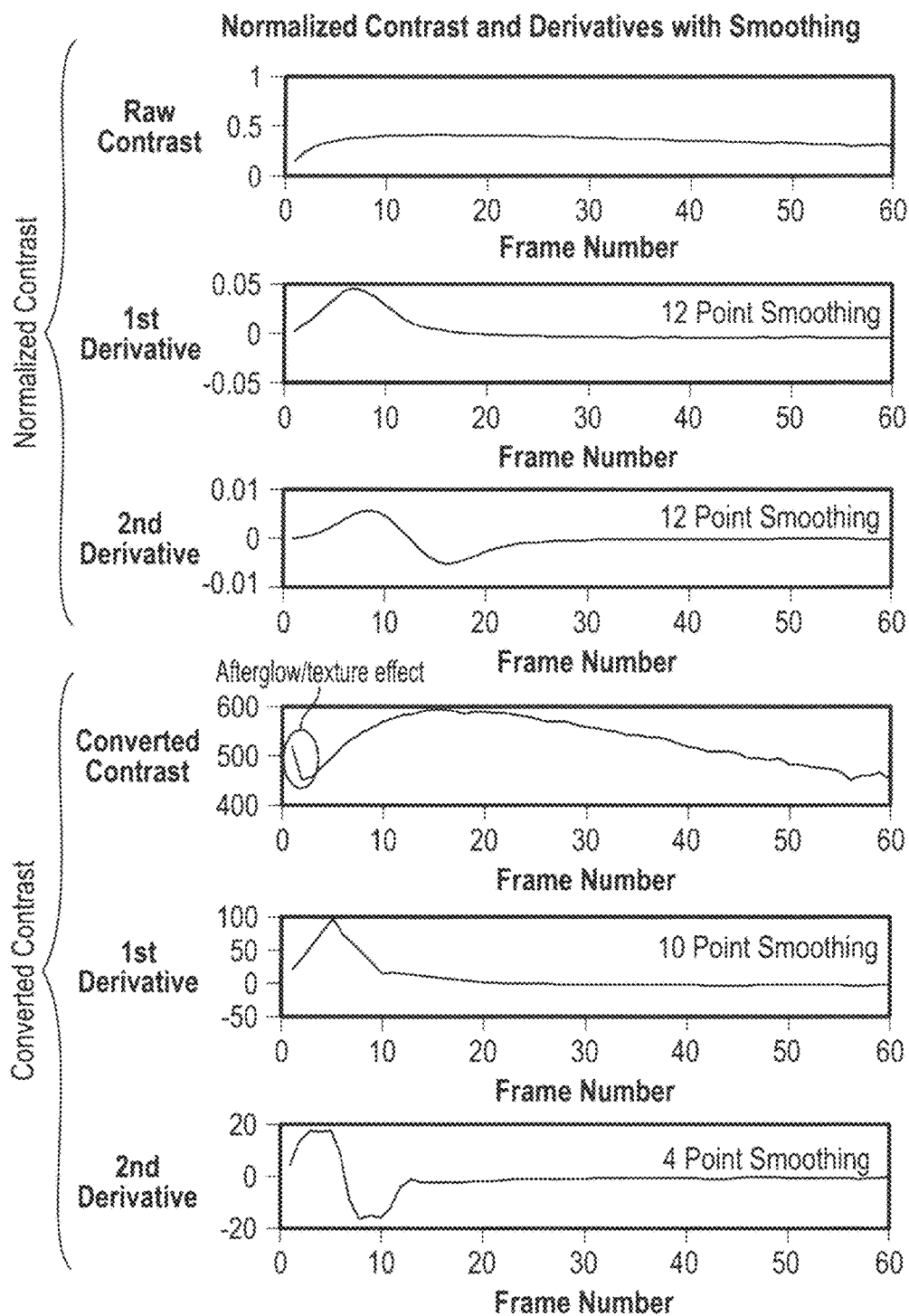
FIG. 18 shows an example of Normalized Contrast and Converted Contrast evolutions and their derivatives in accord with one embodiment.

FIG. 18 shows raw contrast and smooth derivative evolutions for hole number 4 as an example. Top three plots are for direct computation of normalized contrast and its derivatives. The bottom three plots are for the converted contrast and its derivatives. The raw normalized contrast and the raw converted contrast differ for the first three frames. Normalized contrast computation reduces the effect of the afterglow. The material emissivity is about 0.8 and 20% of the afterglow is reflected by the part giving higher than expected pixel intensity until the afterglow decays sufficiently. In normalized contrast computation, relative pixel intensity evolution of the reference ROI is subtracted from the same for the measurement pixel. This subtraction reduces the effect of higher relative pixel intensity in the contrast due to the afterglow. The reference ROI contained 25 pixels, thereby reducing the effect of the texture noise in the reference ROI. The surface texture also affects effect of the afterglow providing relative increase or decrease in pixel intensity values. There is no compensation for the higher or lower relative pixel intensity due to afterglow/texture effect in computation of converted contrast and a peak is observed in the first post flash frame. The converted contrast decays with decay of the afterglow and the diffusion of texture indications. It may reach a value equal to the baseline converted contrast value provided the subsurface anomaly is relatively deep. At the early detection time, the converted contrast starts increasing. Thus, in order for the converted contrast to reach its constant baseline value before the peak time, there should be some time interval between end of the effect of the afterglow/texture and the early detection time. Note that the shapes of the corresponding first and second derivatives of normalized contrast and converted contrast are similar.

Figure 19:
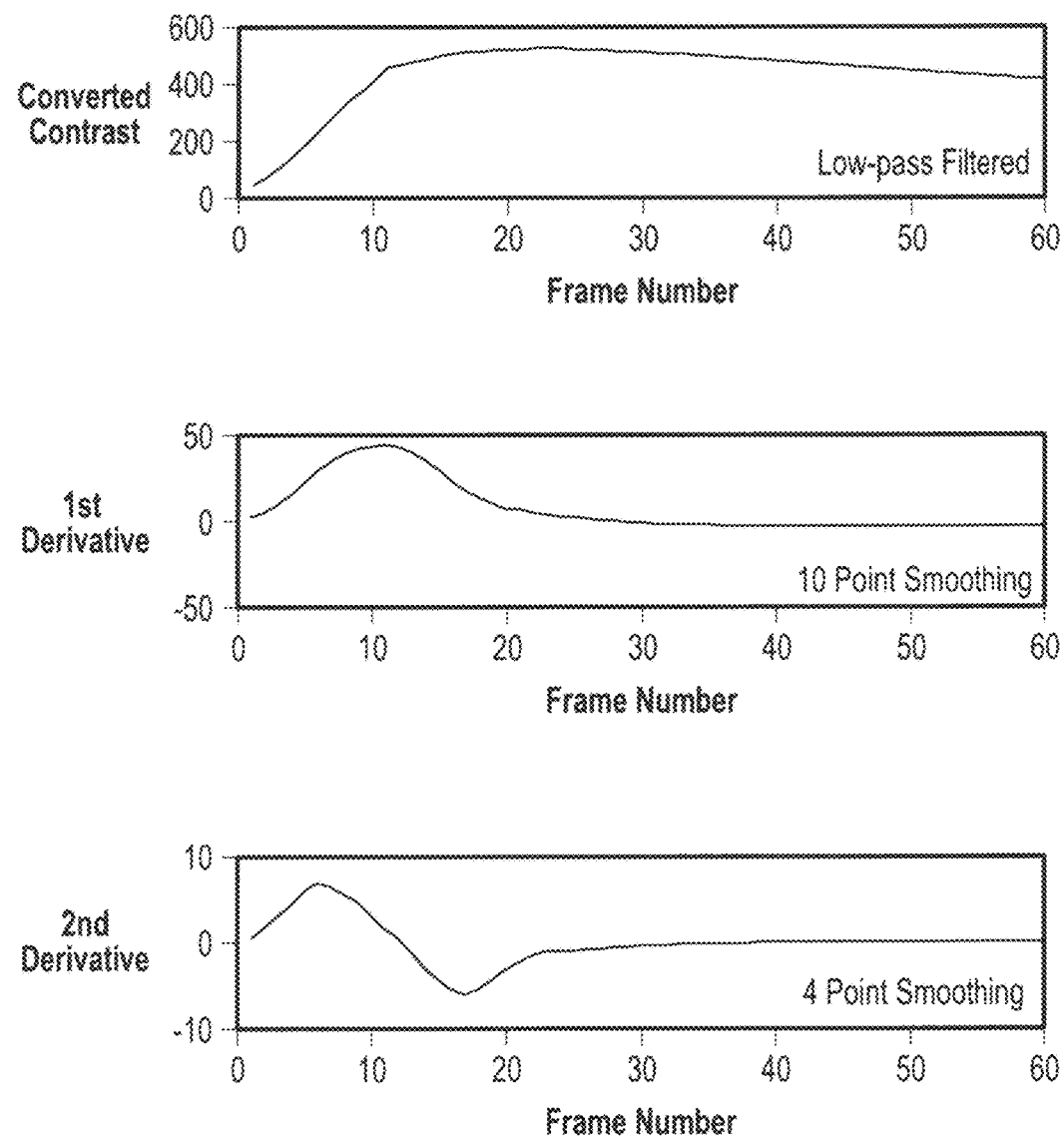
FIG. 19 shows an example of low-pass filtering of Converted Contrast evolution and its derivatives in accord with one embodiment.

FIG. 19 shows an example of low-pass filtering of converted contrast evolution from FIG. 18. Filtering can remove the afterglow/texture effect. If there is no need to evaluate any texture anomalies, then such filtering is useful as it reduces the pixel noise.

Figure 20:
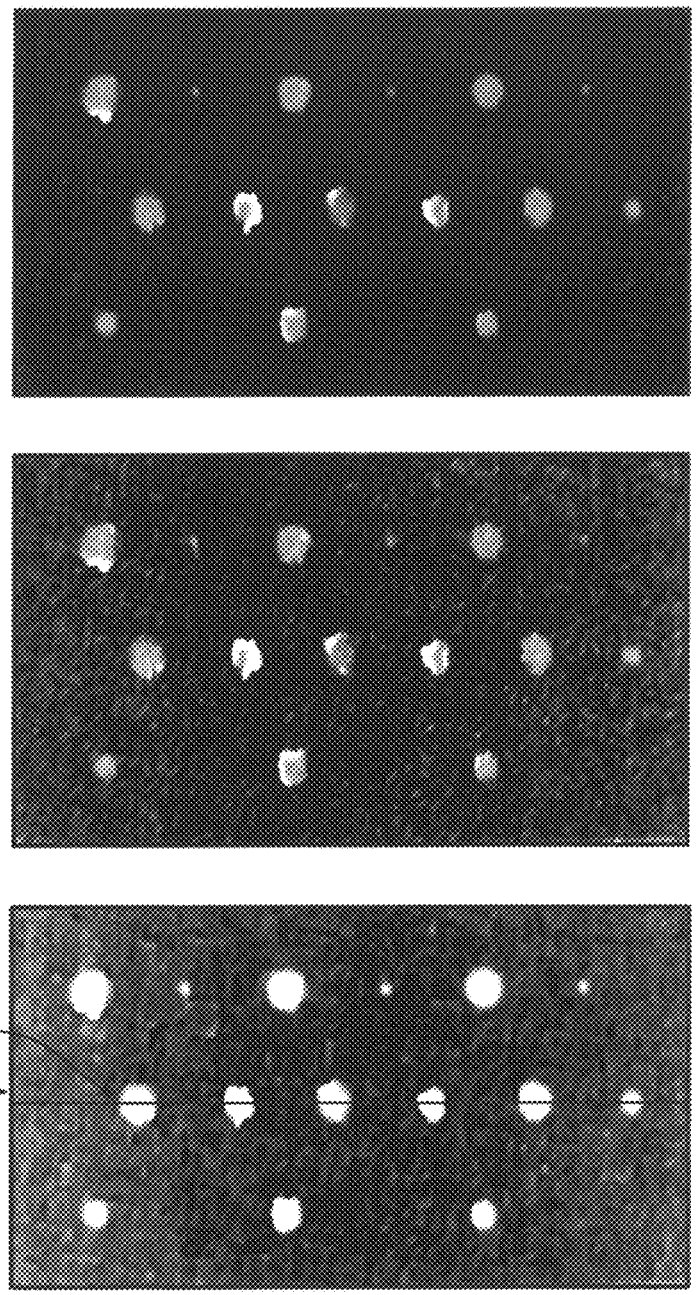
FIG. 20 shows Frame Images for Converted Contrast and Converted Contrast derivatives in accord with one embodiment.

FIG. 20 shows frame 4 images from converted contrast, converted contrast first derivative and converted contrast second derivative data sequences. In this example, all holes are detected. Converted contrast image shows a lot of surface texture. The derivative images also show some texture. These images are considered to be similar to the gated amplitude ultrasonic C-scans and are called the contrast value C-scans.

Another possibility is to show the images from the frame number of the peak contrast from normalized contrast video sequence data and from the converted contrast video sequence data. In other words the image of the maximum contrast frame number from the normalized contrast can be compared with the image of the maximum contrast frame number from the converted contrast. These images look similar and are useful in assessing relative depth of the anomaly. In this case, these images are considered to be similar to the time-of-flight ultrasonic C-scan and are called the contrast time (of flight) C-scans.

Another possibility is to show images of peak product time for normalized contrast and for the converted contrast. The Peak product time is equal to the maximum contrast×the maximum contrast frame number to produce an image from the normalized contrast and from the converted contrast. In some cases, the images may look very similar. The same smoothing or no smoothing may be utilized.

Figure 21:
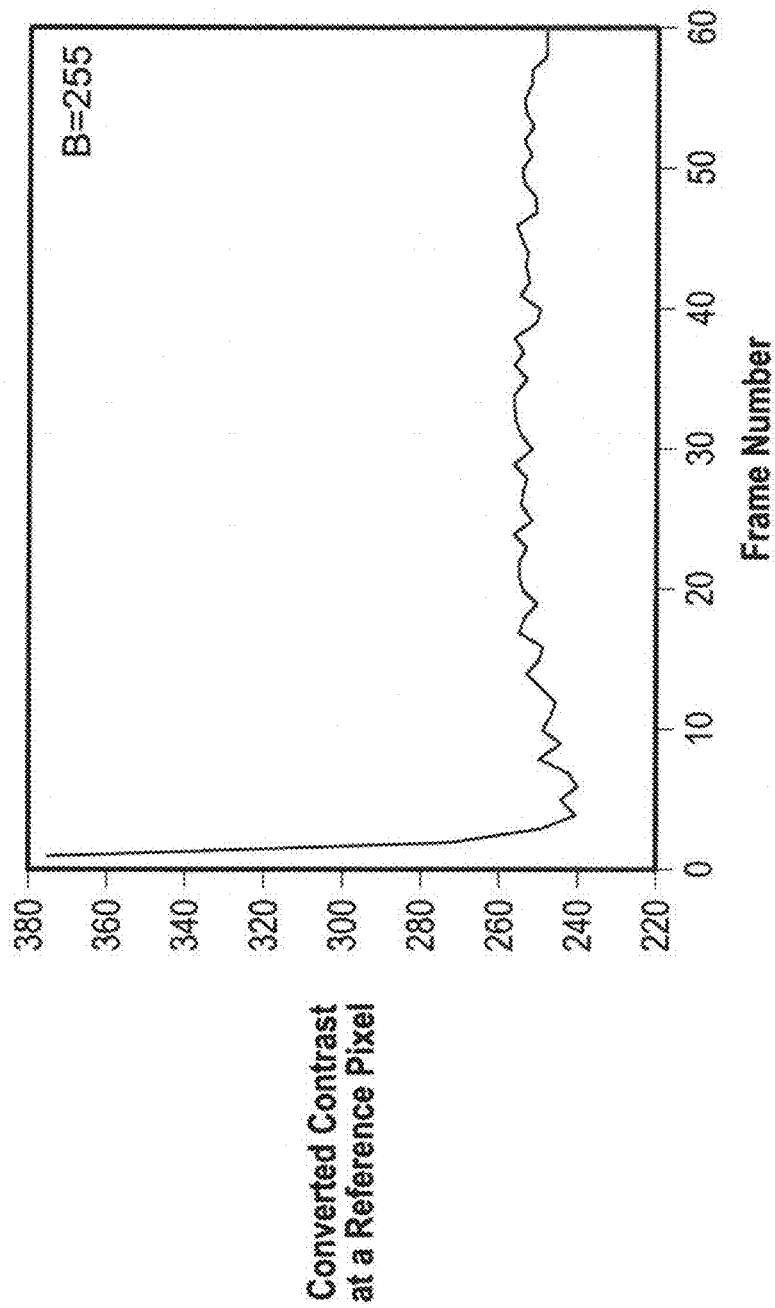
FIG. 21 shows an example of Converted Contrast Evolution at Reference Region of Interest (ROI) in accord with one embodiment.

FIG. 21 shows the converted contrast at a single pixel at the center of reference ROI near hole # 4. The initial high contrast is due to the afterglow/texture effect. After first three frames the contrast levels out more or less. The baseline level (e.g. B) of this portion of the contrast is approximately equal to 255 (pixel intensity×sec0.25).

Another possibility is to show a B-scan representation of the converted contrast for a vertical line passing through holes 4 and 9. In this case, the B-scan shows a lot of afterglow/texture peaks. The largest of these are seen on hole number 5 and number 7. The image is similar to the B-scan representation of the normalized contrast of FIG. 15. The converted contrast can be used to bring out the near surface anomalies.

Figure 22:
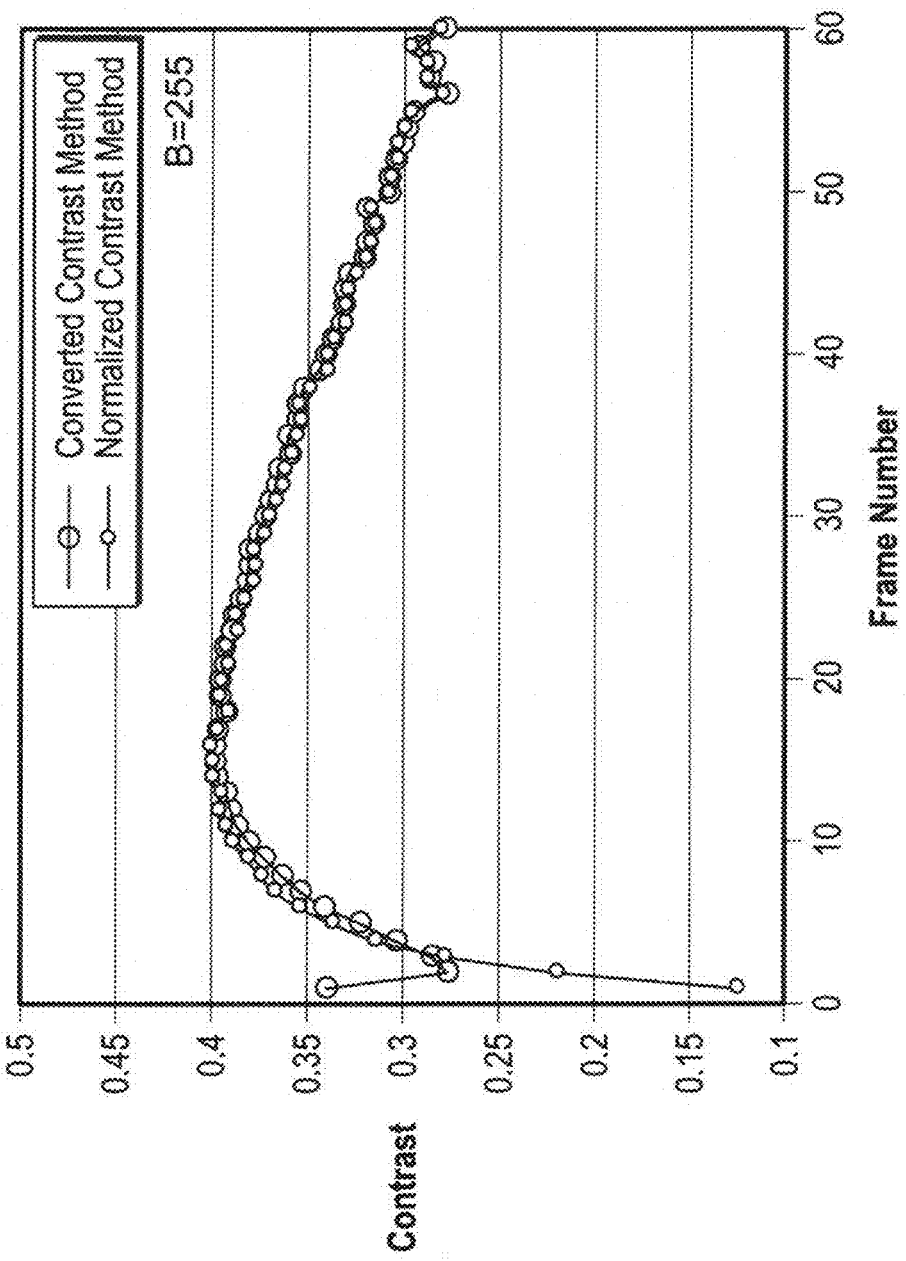
FIG. 22 shows an example of comparison of Normalized Contrast evolution with Converted Contrast evolution at same pixel location in accord with one embodiment.

FIG. 22 shows an example of computation of normalized contrast from the converted contrast for the same contrast evolution used in FIG. 18 and FIG. 19 using a value of B equal to 255. The agreement between direct computation of normalized contrast using Eq. (1) and computation of normalized contrast from converted contrast is good except for the first two frames where the afterglow/texture effect is evident. The normalized contrast provided a smooth variation of slope in beginning frames implying that the afterglow/texture effect is mainly dominated by the afterglow and not by the texture in this example.

EXAMPLE 2

Converted Contrast Method Using Curve Fitted Multiplier Function

Another possibility is to show a plot of relative pixel intensity at a reference ROI with respect to time and its curve fitted function. A ratio of polynomials is chosen for the fit function, however Gaussian and power series equations also showed good fits. In this case, $F(t)=(p1*t+p2/(t^2+q1*t+q2)$, which gives the equation for the coefficients p1, p2, q1 and q2. In one example, the cofficents are determine with 95% confidence bounds. Although, use of a statistically fitted multiplier function yields better results, it requires additional step of fitting curve to the relative intensity of the reference ROI and results in many coefficients. Using simply the fractional power of time for the multiplier function is very attractive as only one coefficient (e.g. n) is used, which could be easily determined for a given material test set-up and could be used on the same material. This, provides use of the implied reference rather than a chosen ROI for the reference. The fitted multiplier functions also may be used in similar manner upon verifying their applicability.

Another possibility is to show a plot of converted contrast at the same selected reference pixel as discussed above for the example of the fitted normalized contrast evolution with peaks in the derivatives. The plot is a line about horizontal with mean close to 1.0 as expected. Here, B=1 in Eq. (31).

Another possibility is to show a comparison of converted contrast and normalized contrast evolution plots, for example, at hole number 4 pixel. In one case, the plot is very close to the normalized contrast using the direct method using Eq. (1). FIG. 22 graphically shows a comparison on the same graph.

Figure 23:
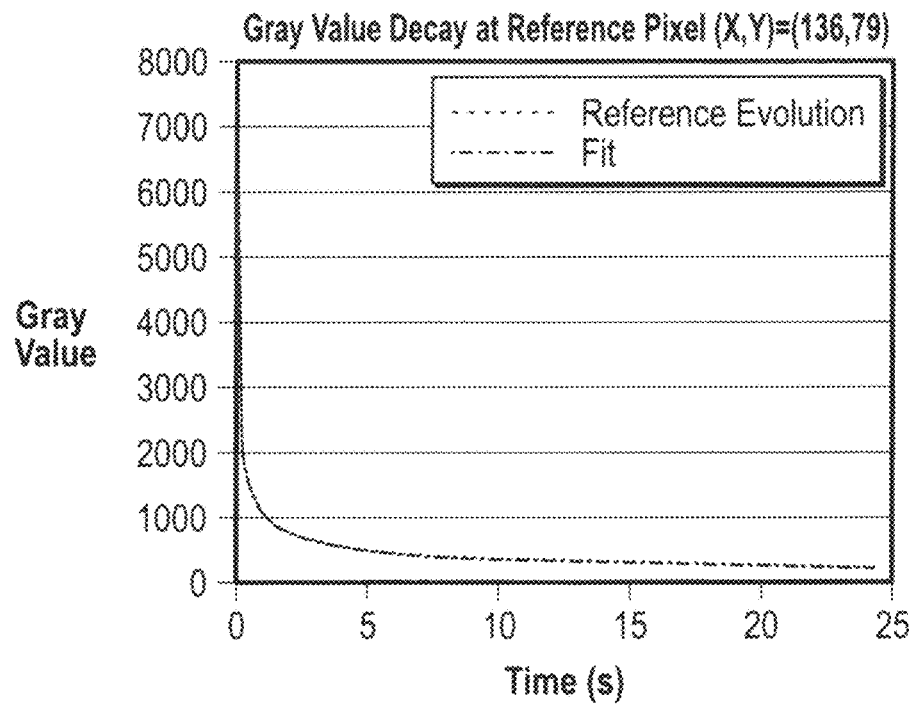
FIG. 23 shows an example of reference region of interest (ROI) evolution, line fit, slope and multiplier in accord with one embodiment.
Figure 23:
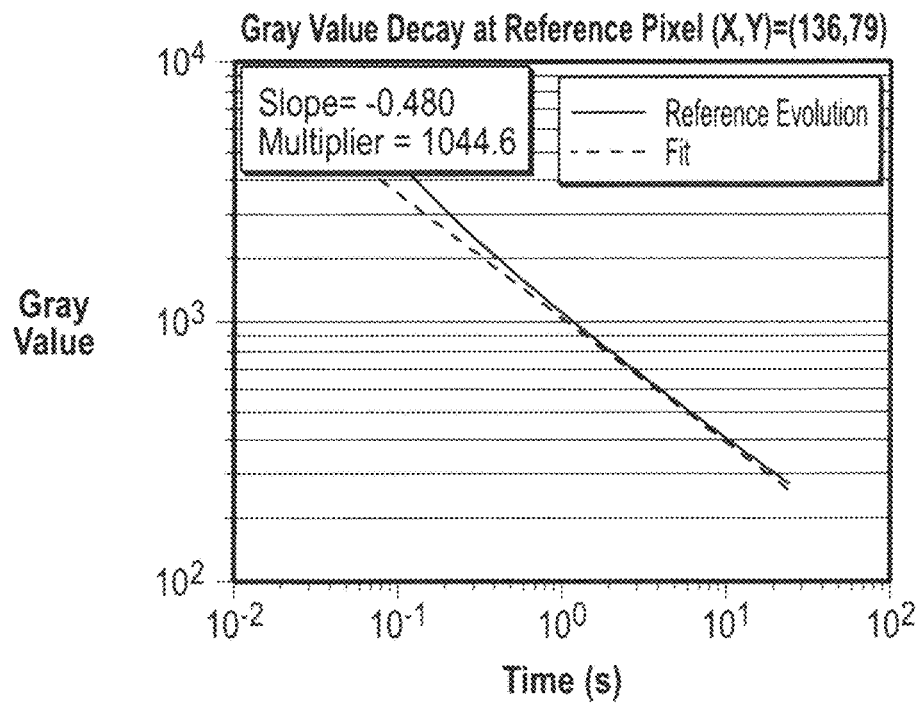

FIG. 23 shows example of reference region of interest (ROI) evolution, line fit, slope and multiplier for specimen 2.

Figure 24:
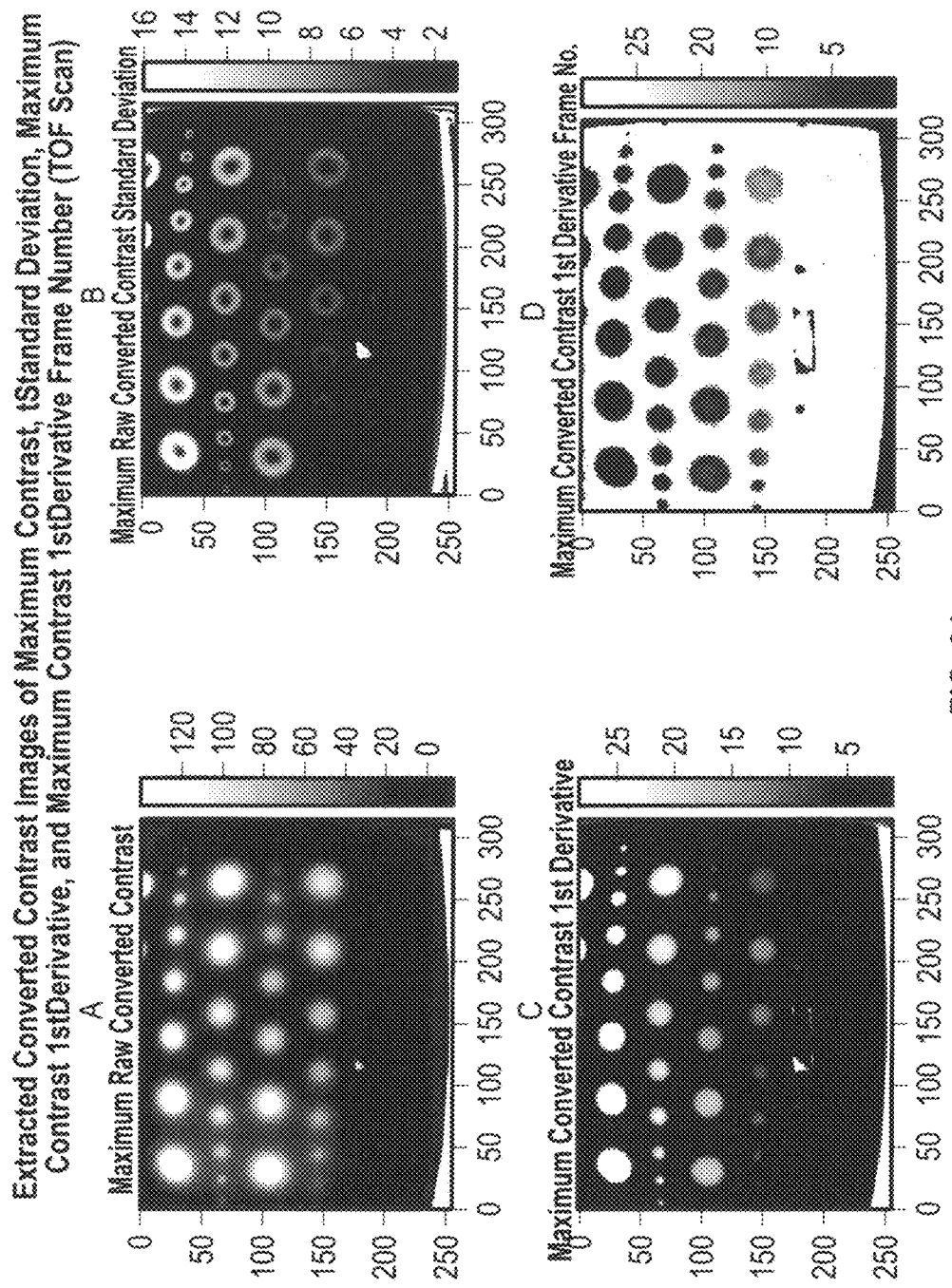
FIG. 24 shows Extracted Converted Contrast images of peak contrast, standard deviation of peak contrast, peak of contrast first derivative, and frame number at peak of contrast second derivative (time of flight scan) in accord with one embodiment.

FIG. 24 shows extracted converted contrast images of peak contrast, standard deviation of peak contrast, peak of first derivative of contrast, and frame number of peak of first derivative (time of flight scan) for specimen 2 using slope s and multiplier M given in FIG. 23.

Temperature Contrast Computation

Figure 25:
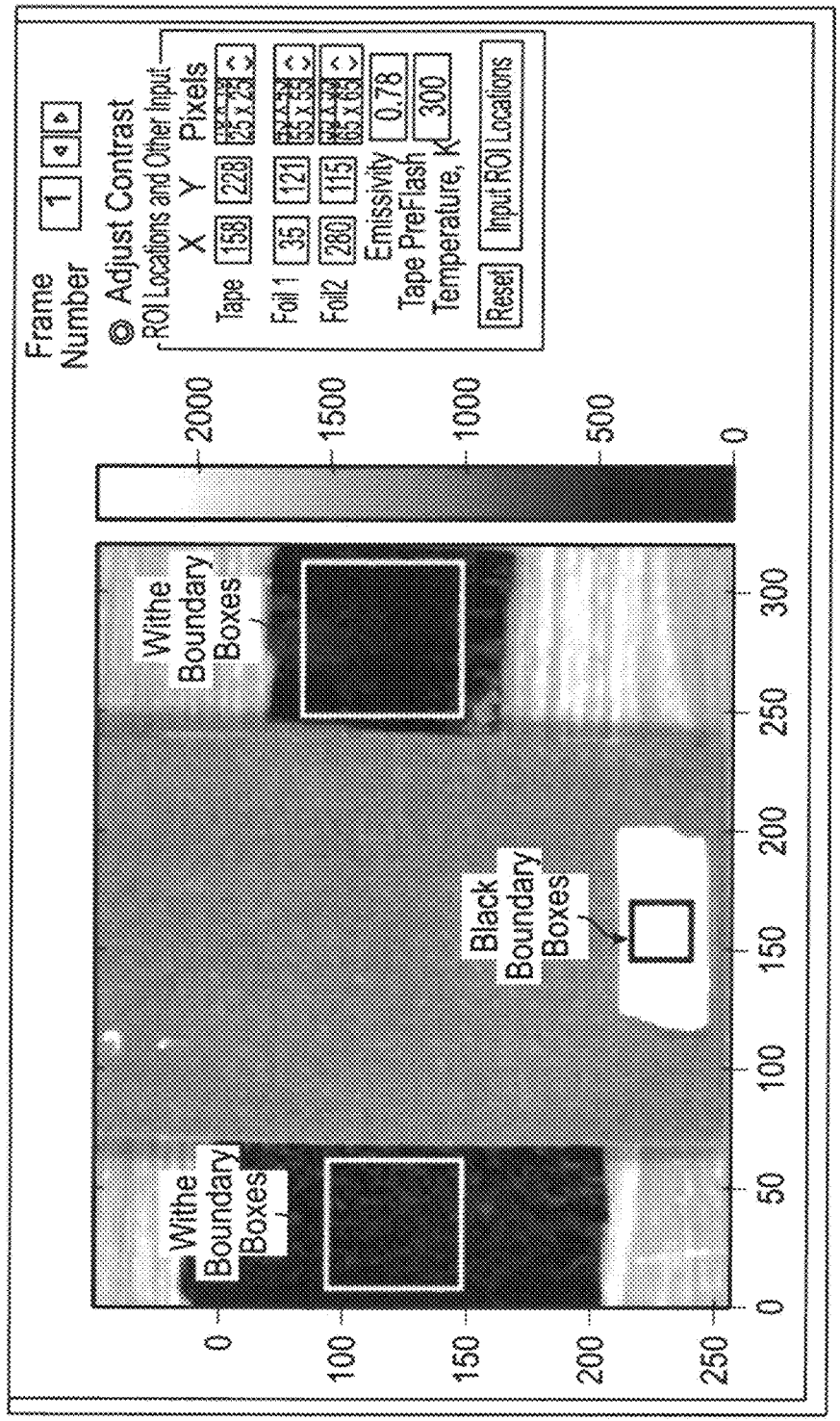
FIG. 25 shows an input display of a computer-implemented Temperature Measurement method set-up for a reinforced carbon-carbon test part labelled as Specimen C in accord with one embodiment.

Computation of surface temperature and normalized temperature contrast during flash thermography utilizes a foil and tape set-up as described in U.S. Pat. Nos. 8,577,120 and 9,066,028 and shown generally in the representation of FIG. 25. Here, metallic foils are used to monitor camera side diffused reflection. A black color tape, affixed to the part, is used get emissive irradiance primarily before flash. The part surface temperature at the tape before flash is independently measured and input in this method. An input panel display for temperature measurement is shown in FIG. 25. Emissivity of part surface is also provided as input. ROI's for tape and foil are established. There are two ROI's for foil and one for tape. Average pixel intensity evolution from the two foil ROI's is used. Average pixel intensity evolution from within the tape ROI is used. These input quantities are used to compute temperature evolutions preferably at each pixel as given herein.

From surface temperature, temperature rise is computed as, $$T_{rise}=T-T^0. \tag{39}$$

Also simple contrast is computed as, $$C_{simple}{}^T=T-T_{ref}. \tag{40}$$

Figure 26:
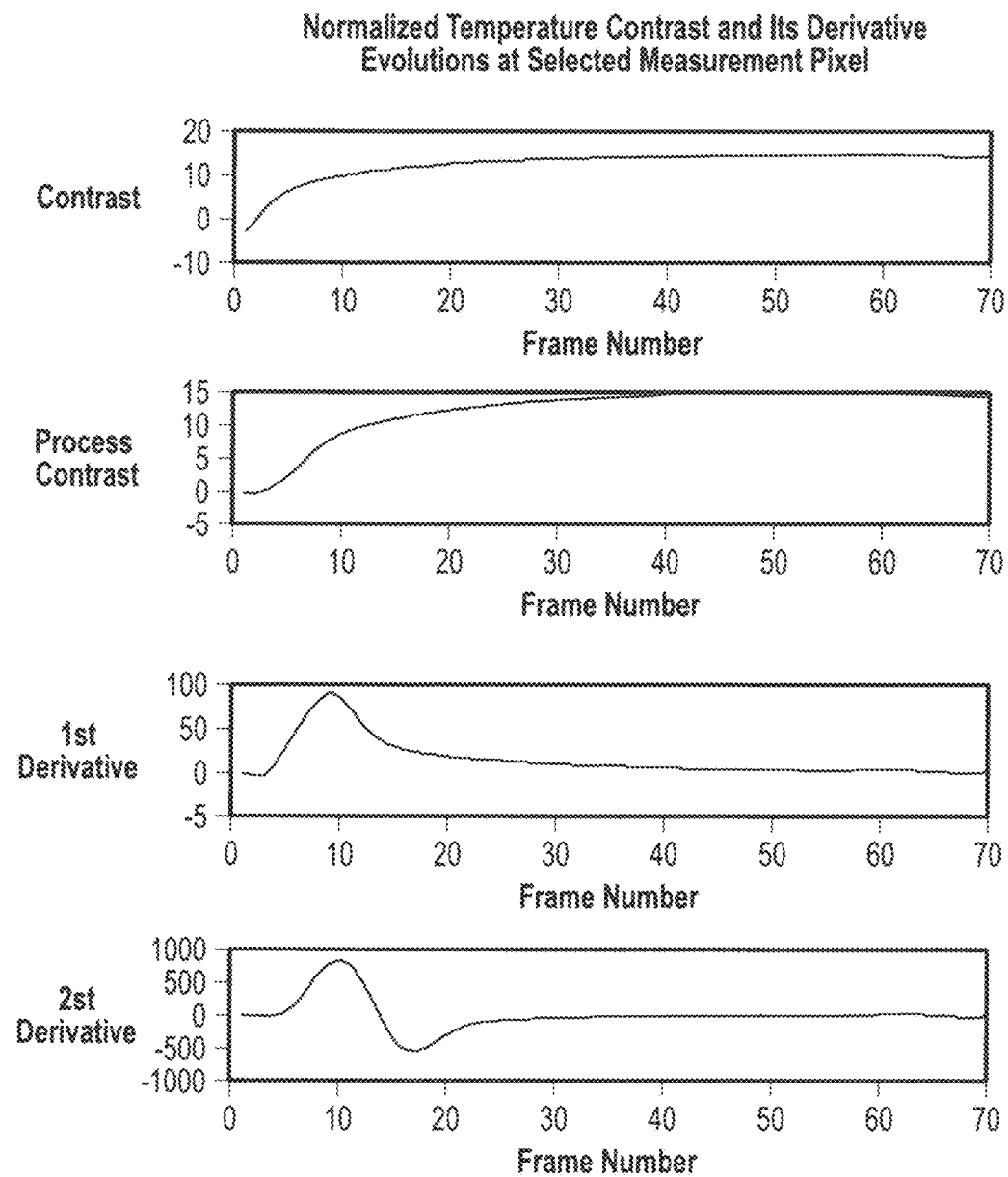
FIG. 26 shows an example of Normalized Temperature Contrast evolution and its derivative evolutions at a selected measurement pixel in accord with one embodiment.

FIG. 26 shows an example of normalized temperature contrast evolution, smoothed or processed normalized temperature contrast evolution and its derivative evolutions at a selected measurement pixel.

Another possibility is to show temperature contrast extracted images. In other words, Normalized Temperature Contrast Frame Images can be shown for surface temperature, standard deviation of surface temperature, temperature rise, and temperature difference. In one example, this may include an image for each of the maximum raw temperature contrast, the maximum raw temperature contrast standard deviation, the maximum temperature contrast $1^{st}$ derivative, and the maximum temperature contrast $2^{nd}$ derivative.

Figure 27:
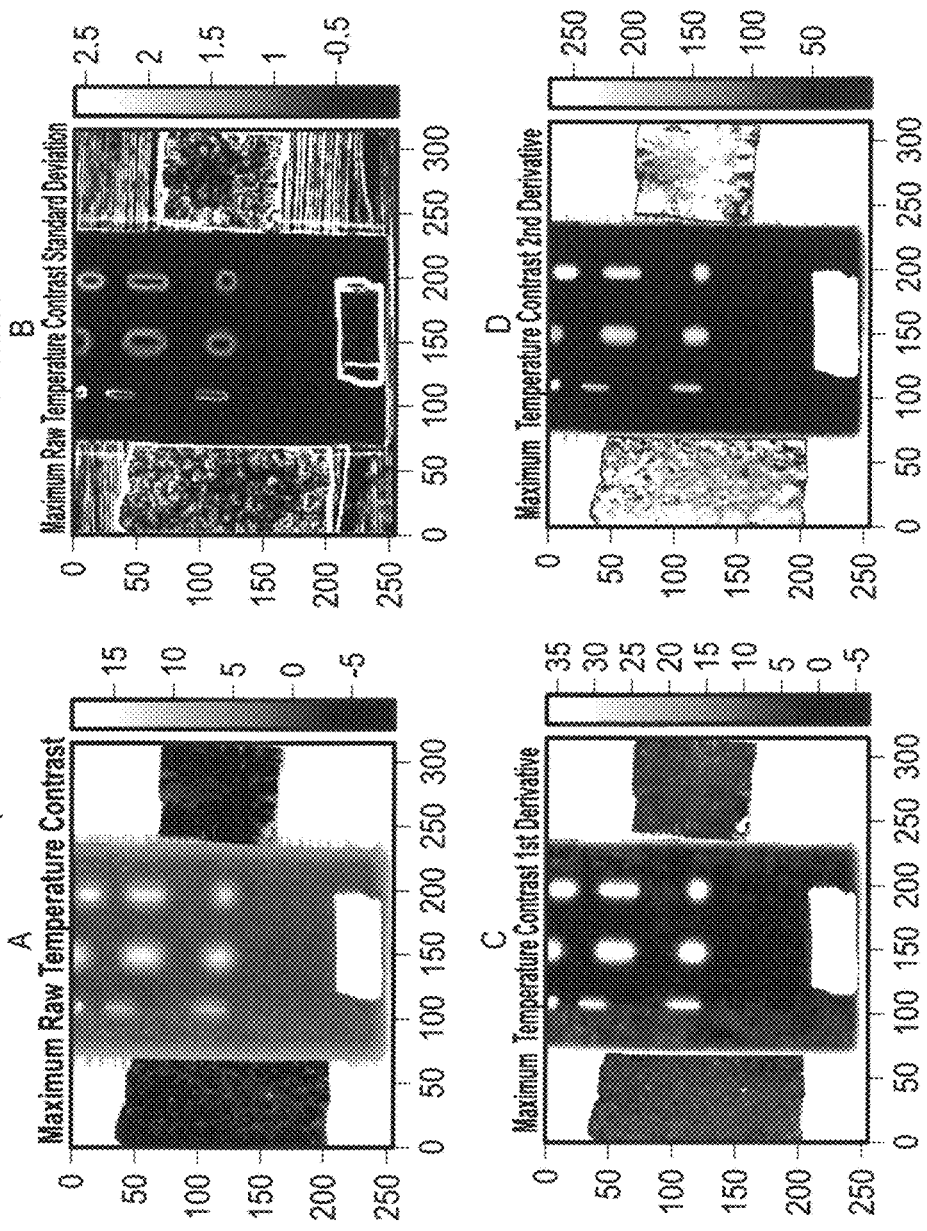
FIG. 27 shows Normalized Temperature Contrast Extracted Images of peak contrast, standard deviation of peak contrast, and peak of contrast first derivative, and peak of contrast second derivative in accord with one embodiment.

FIG. 27 shows Normalized Temperature Contrast Extracted Images of peak contrast, standard deviation of peak contrast, and peak of first derivative of contrast, and peak of second derivative of contrast.

Normalized Contrast Calibration Method

As discussed herein, the embodiments described herein show that point measurement of normalized contrast on a round anomaly can be used in data analysis. Further it was shown that the entire flash thermography data sequence can be converted to contrast video sequence data and used for data analysis. Here, an empirical method is provided to calibrate normalized contrast response as a function of size of artificial anomalies in the shape of round flat bottom holes or embedded gaps. Once calibrated, the calibration data can be used to assess depth of anomalies during flash thermography inspection. The calibration data provides six properties of contrast evolution namely the peak time and peak contrast (amplitude), time scale factor, offset time, begin time, and slope (different from slope factor) as a function of depth and diameter of the anomalies in a calibration reference standard.

Figure 4:
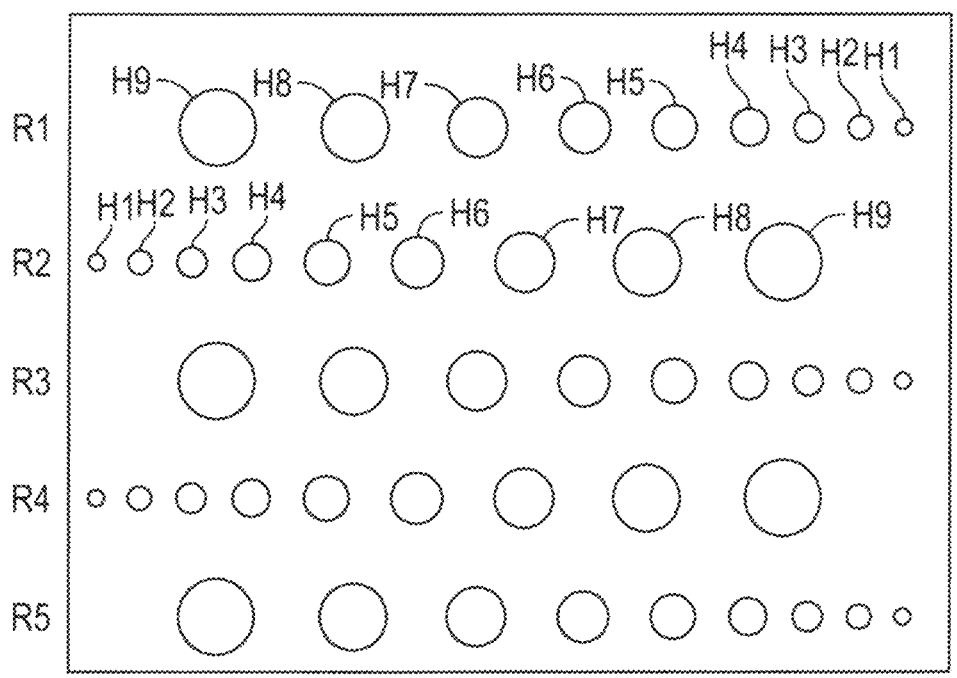
FIG. 4 provides a schematic of a back side of the graphite-phenolic calibration standard B from FIG. 3.
Figure 5:
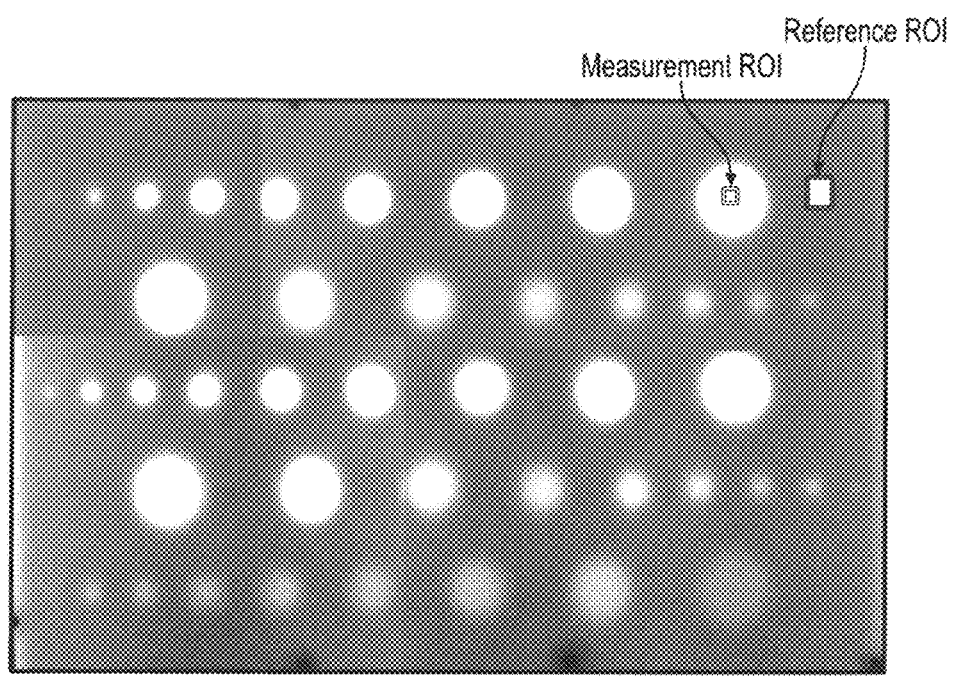
FIG. 5 provides an IR image of the graphite-phenolic calibration standard B of FIG. 4 from raw data.

A calibration standard with flat bottom holes (or embedded gaps) with desired diameter (D) and depth (d) values is prepared. FIG. 3 shows a schematic of such a standard with flat bottom holes. FIG. 4 shows a schematic of the standard. FIG. 5 shows a flash thermography raw data image for a selected frame or time within the data sequence. The image is created by overlapping 6 shots. The holes are arranged in five rows. There are 9 holes in each row with 9 different diameters. These diameters are same in each row. Depth of flat bottom holes in a given row is same. The depths and diameters create a 9 by 5 grid of 45 diameter-depth pairs. Measurement ROI for each hole is chosen in the center of image of each hole. The reference ROI is chosen in the vicinity of image of the hole at a location that provides an optimal contrast evolution profile. See FIG. 5. A text file with measurement and reference pixel data is extracted from the data sequence for each hole indication. See FIG. 12 for a sample contrast data text file. The text files and their associated flat bottom hole diameter and depth values are used to generate data for the calibration.

Figure 28:
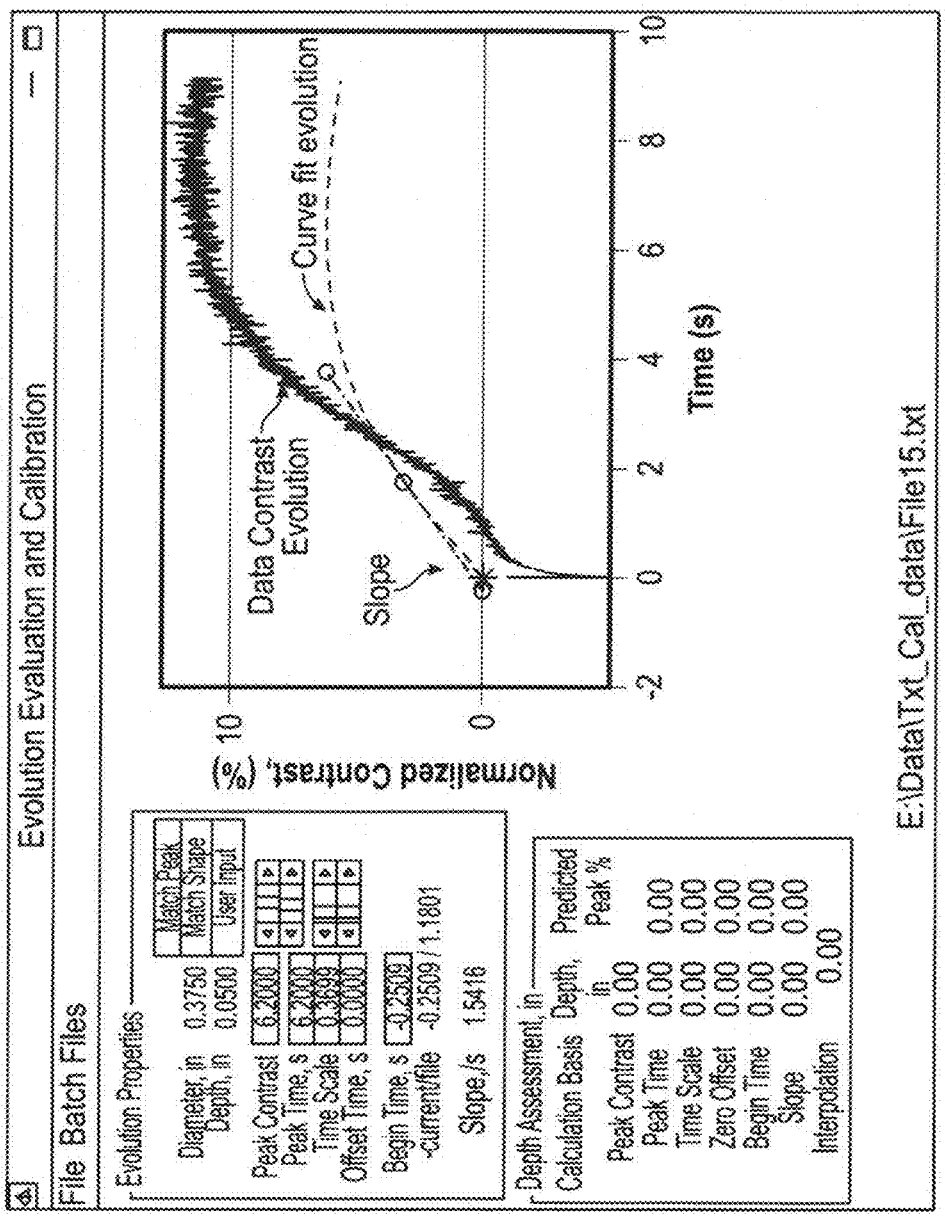
FIG. 28 shows a method of matching Fit (Simulation) Curve to Normalized Contrast Evolution in accord with one embodiment. As shown, the Curve Fit is not yet matched.
Figure 29:
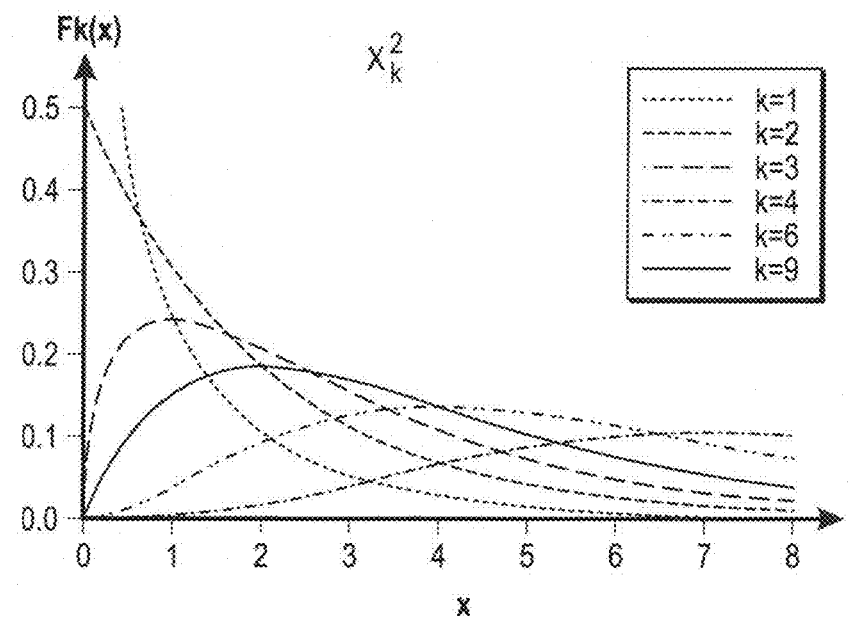
FIG. 29 shows a Chi-Square Probability Density Function for various values of k in accord with one embodiment.

First each extracted contrast data file is displayed as a normalized contrast evolution. Next the six contrast evolution parameters are calculated by analyzing the contrast evolution. FIG. 28 shows a computer method panel for assessment of the contrast parameters and the assessment of the depth. The contrast evolution file is opened using a method from the computer screen shown in FIG. 28. The method also provides a curve fit where a χ2 Chi-square probability density distribution is fitted to the contrast evolution. See FIG. 29 for Chi-Square probability density function for various values of k. Here, it is assumed that there is a single peak to the distribution. The distribution starts with zero value for zero time and reaches zero value at a long time or infinity.

A χ2 (or Chi-square) probability density function (PDF) distribution chosen for the fit is given by.

$$f(x; k) = \frac{x^{(k/2)-1} e^{-x/2}}{2^{k/2} \Gamma\left(\frac{k}{2}\right)} \quad (41)$$

for $x \geq 0$ and $f(x; k) = 0$ otherwise.

Here, $\Gamma(k/2)$ denotes Gamma function. The Gamma function is given by, $$\Gamma(z) = \int_0^\infty e^{-t} t^{z-1} dt \quad (42)$$

Although, the PDF distribution for various values of k provides sufficient variability in shapes that look very similar to real normalized contrast evolutions, the PDF distribution cannot fit the entire length of the contrast evolution for many cases of contrast evolutions. Distribution fits can be improved by increasing the number of coefficients used in a chosen fit equation. However, for one embodiment the number of distribution coefficients is kept to four to create a simpler approach. The four contrast parameters are peak time, peak contrast, time scale factor, and offset times which completely define the Chi-square PDF distribution. Normally, amplitude and peak time are not used as the input parameters to the Chi-square distribution. Therefore, an algorithm is used to determine the Chi-square coefficients including k that provide the desired parameter values. The fit is allowed to be shifted, therefore zero offset time is used to achieve the shift.

Contrast evolution slope of the fit is calculated at the 50% peak point in rising side of the contrast and is indicated by a 'o'. A slope line is drawn at the 50% of peak of fitted contrast. Begin time is used indicate the early detection time of fitted contrast evolution. It is given by starting point of the slope line at zero value of normalized contrast and is indicated by '*'. Slope line upper end has value of peak contrast and it is indicated by a 'o' as well. Slope value is not used as an input. Begin time input of slope line is visually observed in the plot and adjusted accordingly. Slope value is calculated automatically.

A Match Peak sub-method (FIG. 30, button 3002) allows matching of peak point of fit with that of the contrast evolution for a given scale factor, offset time and begin time.

Alternatively, a Match Shape sub-method (FIG. 30, button 3006) allows matching of shape of fit with that of the contrast evolution for given peak contrast, peak contrast time, offset and begin time. FIG. 31 shows an example of computation of difference between simulation fit and normalized contrast evolution as a function of time scale factor. This plot is provided by Match Shape sub-method. A V shaped curve indicates that a minimum in the difference has been reached and the corresponding time scale factor is close to the optimal value and this value is automatically updated.

A User Input method (FIG. 30, button 3008) allows updating of the fit using all five displayed values of the parameter.

Each of peak contrast, Peak Time, Time Scale, Offset Time and Begin Time slider control methods (FIG. 30, slider controls 3010) allow adjustment of the corresponding parameter and instant update of the fit.

Figure 30:
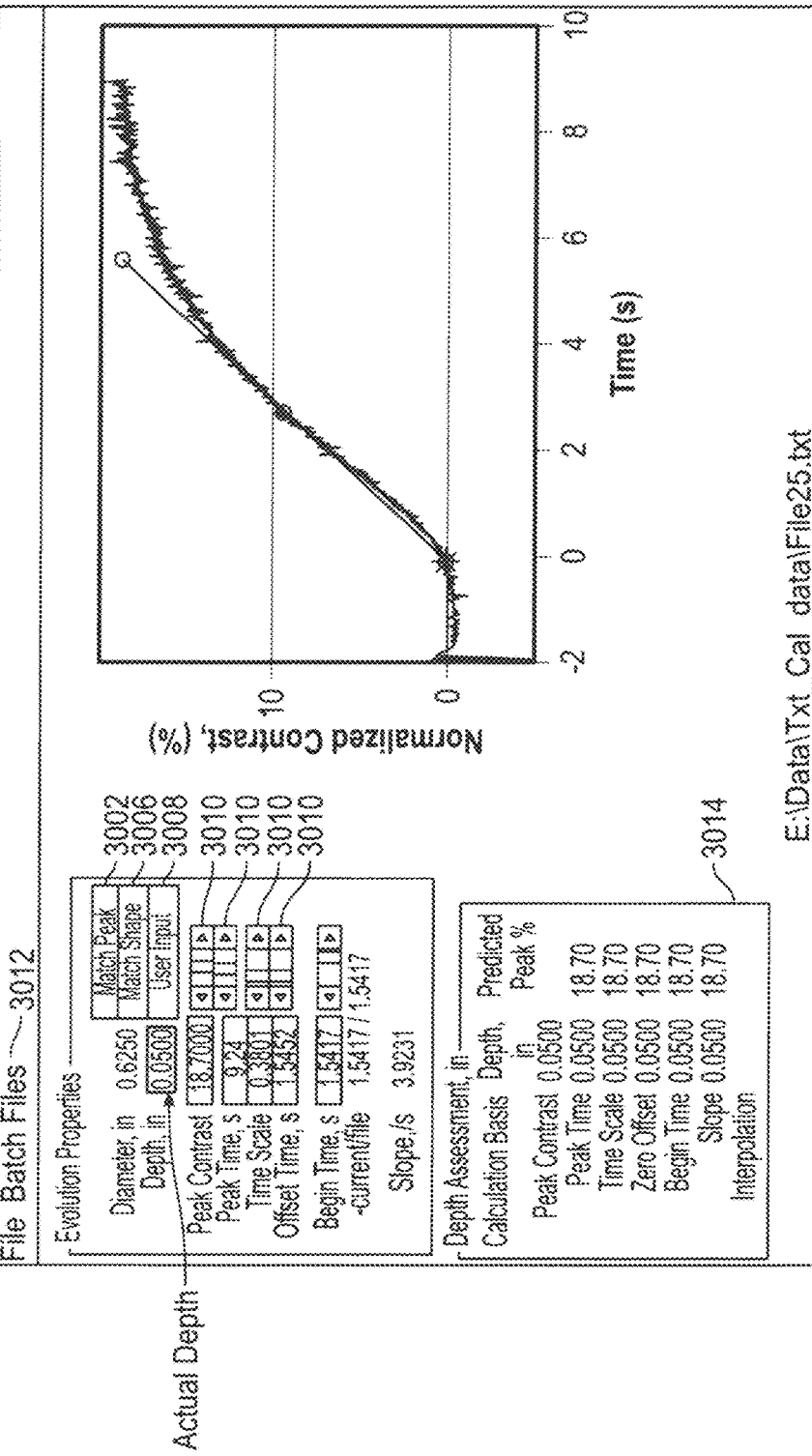
FIG. 30 shows a method of matching Fit Curve to Normalized Contrast Evolution in accord with one embodiment. As shown, the Fit Curve is matched.
Figure 31:
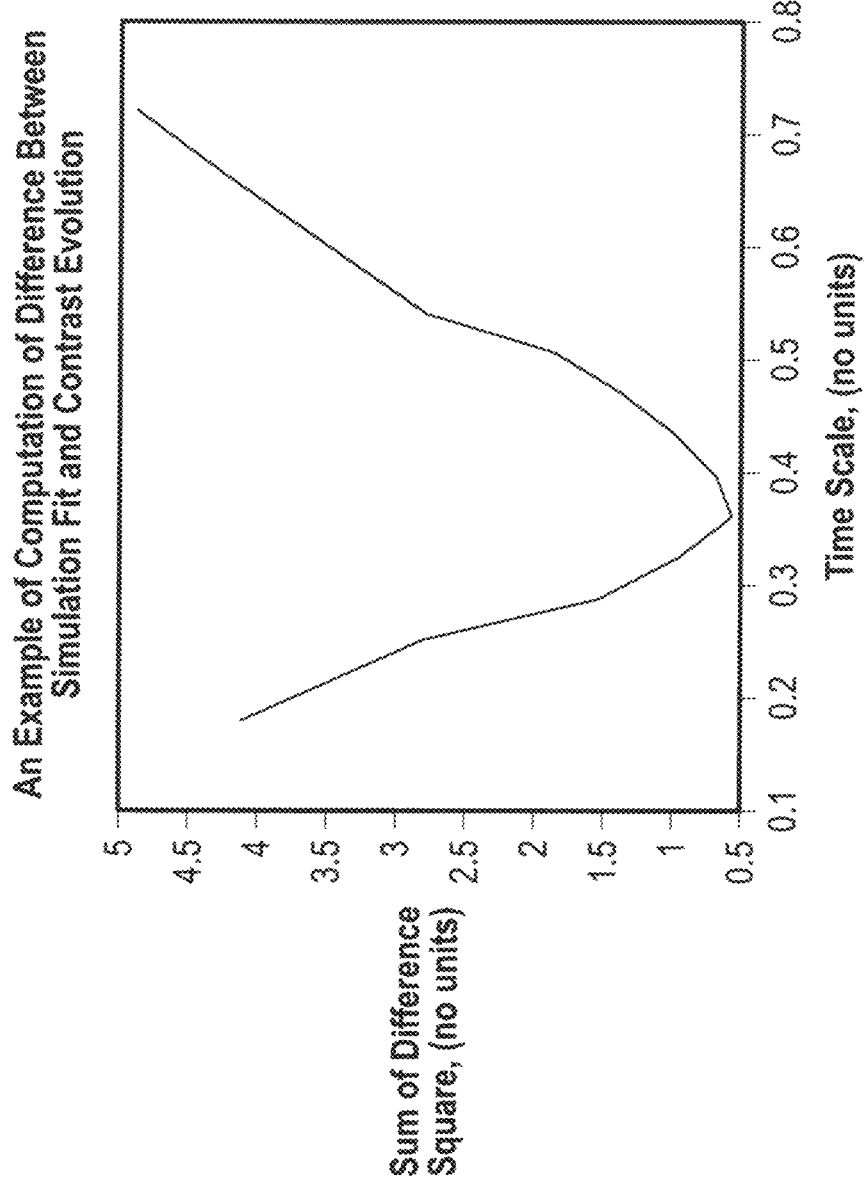
FIG. 31 shows an example of computation of difference between Curve Fit and Normalized Contrast evolution in accord with one embodiment.

FIG. 30 shows method of matching a fit curve to a normalized contrast evolution. Here simulation is matched.

The contrast evaluation method shown in FIG. 28 is used to update the evolution data file with diameter depth and the six contrast parameters. See FIG. 12. To complete calibration, each of the 45 contrast evolution files are evaluated and their files are updated.

The contrast evaluation method reads the calibration contrast evolution data files as a batch and creates a database internally. See Batch Files sub-method in FIG. 30, item 3012.

Figure 33:
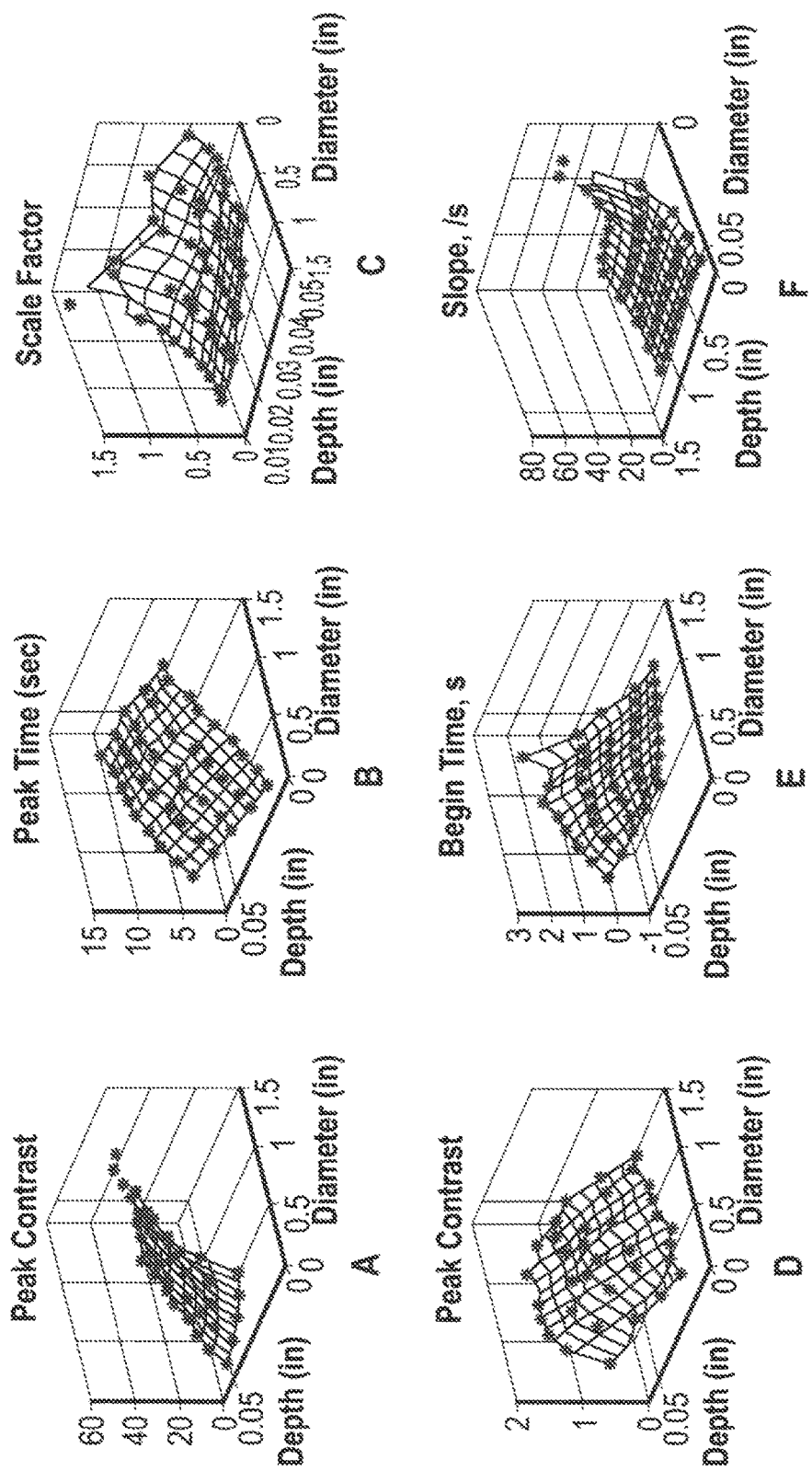
FIG. 33 shows Calibration Data surfaces for the six Normalized Contrast Evolution Parameters in accord with one embodiment.

The data values of calibration database are given in FIG. 32. The calibration database has 8 columns of data and 45 rows. There is one row for each contrast evolution corresponding to each calibration hole. First two columns are for diameter and depth. The last six columns are for the six contrast parameters. The contrast evaluation method displays the calibration data in six 3D plots with fitted surfaces. These are used to detect any unexpected trends and make corrections. Smoother surface fits are expected. FIG. 33 shows Calibration Data and fitted surfaces for six normalized contrast evolution parameters.

In order to evaluate a contrast evolution from an anomaly indication, first the data file is loaded using File sub-method and all calibration files are preferably read using the Batch Files sub-method. See FIG. 30. The contrast evolution is evaluated by fitting a curve and slope line through the curve. Diameter or width of the indication should be measured in Frame images or Extracted images. The six contrast evolution parameters and the diameter are updated in the contrast evolution file and using sub-method of Evaluate Depth, depths are assessed and displayed in bottom left. Up to six estimates, one from each parameter, are obtained by interpolating calibration data. See FIG. 32 and FIG. 33 for calibration data. See FIG. 30, box 3014 bottom left for the depth estimates. A seventh estimate is called Interpolation estimate and is based on interpolation of the previous, up to six, estimates using predicated peak contrast from these estimates to give a depth that gives the observed peak contrast. If the six estimates are identical then there is no interpolation. The final interpolation increases confidence in depth estimation. See FIG. 30, box 3014 bottom left.

Note the reference standard may have other types of flaws created by pre-curing known size areas at selected plies within composites and then curing the entire part. These create delamination like anomalies of known size and depth.

Here, round flat bottom holes are used in a calibration standard. The standard can be generated from embedded gaps or delaminations with rectangular or other shapes with fixed length to width aspect ratio. In this situation, the width of the flaw would be used in place of the diameter. It is recommended to maintain the same gap value in a given calibration file. The calibration flaws should replicate the flaws to be evaluated, especially in shape and gap thickness, to provide better assessment of depth of the anomalies and POD analysis.

Other Image and Data Analysis Methods

Figure 34:
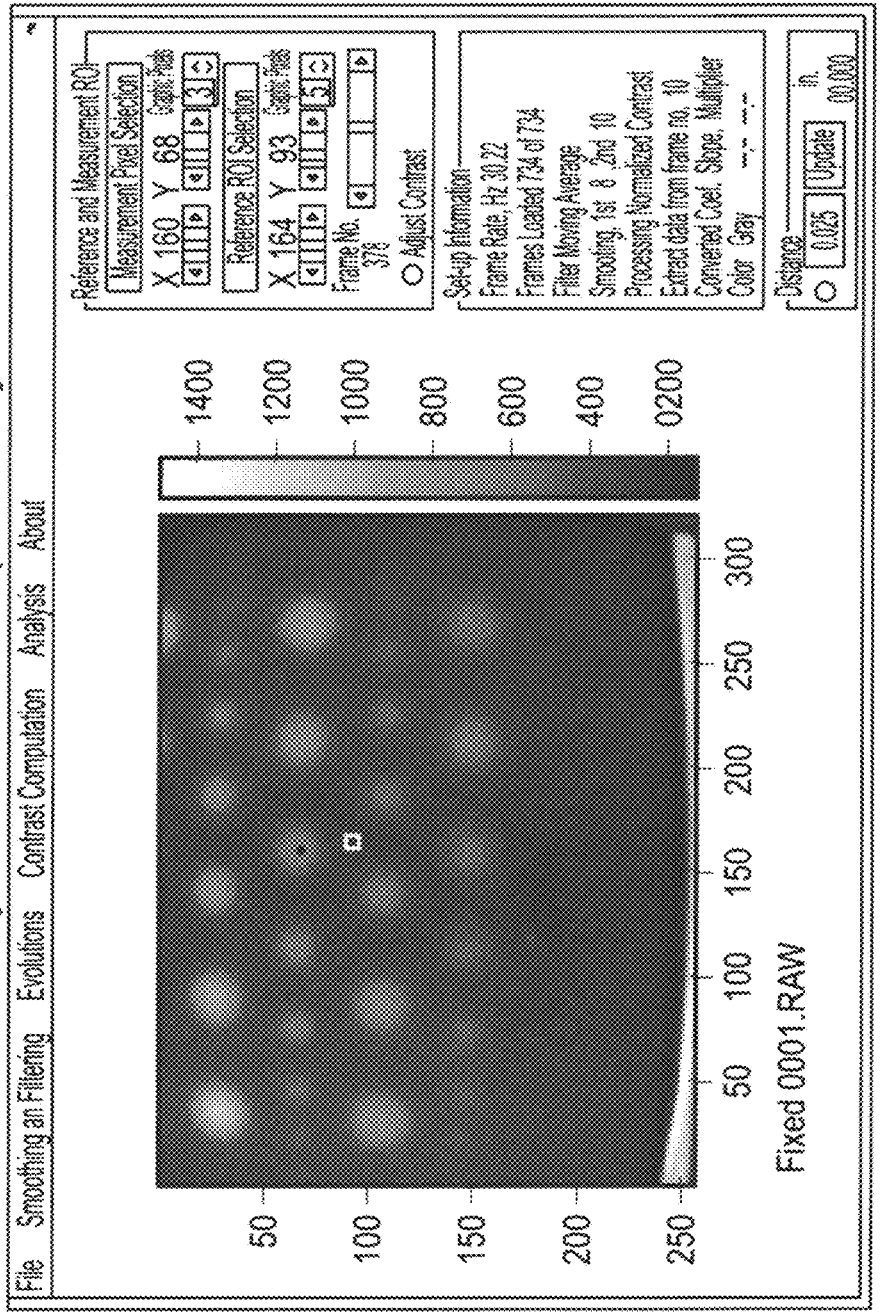
FIG. 34 shows a main panel for the Contrast method and shows organization of sub-methods of Smoothing and Filtering, Evolutions, Contrast Computation and Analysis in accord with one embodiment.

Because of many options of image data analysis, it is desirable to organize and integrate methods for computation. Many contrast methods given here, except POD analysis, can be integrated in a Contrast method main panel shown in FIG. 34. Numerous options for different types of contrast methods have been provided in this application and previous patents that can be implemented by a computer program that can pull up these procedures. In one application, the methods below are implemented from a computer screen. Accordingly, the embodiments described herein provide for processing steps for the Contrast methods that include those and other image and data analysis methods some of which are listed below.

1. Method of Smoothing and Filtering provides choice of Smoothing points, and Filters (e.g. moving average).

2. Method of Evolutions provides extraction of contrast evolution for selected pixel as a data file. See FIG. 12. Normalized contrast evolutions and its derivatives at a selected pixel as shown in FIG. 26. Evolution Evaluation and Calibration method. See FIG. 28.

3. Method of Contrast Computation provides three options, i.e., Normalized contrast, Converted contrast and Normalized temperature contrast.

4. Analysis method in main panel provides three options, i.e., Frame images, Extracted images and Analyze saves images.

Video frame images are called Frame Images herein. A frame number is associated with each frame image. The Frame images method is integrated in a Frame Images panel for a computer software program implementing the methods described herein.

5. Frame Images panel or screen in the computer program has Frame Images, Analysis sub-methods, and Options for Frame Images. For example a video sequence may be chosen for a frame image. From this a frame number may be chosen to display and/or adjust contrast or to play the video and adjust the contrast. Additional steps may involve evolutions and profile, edge detection, area statistics, length measurement, and standard deviation. A choice of video sequences for frame images may include:
  1. Raw Data (Gray Scale)
  2. Normalized Contrast
  3. Processed or Smoothed Contrast
  4. Contrast $1^{st}$ Derivative
  5. Contrast $2^{nd}$ Derivative
  6. Temperature, K—applicable for Normalized Temperature processed data only
  7. Temperature rise, K—applicable for Normalized Temperature processed data only
  8. Simple contrast, K—applicable for Normalized Temperature processed data only 6. Analysis method provides Contrast (normalized, converted contrast and temperature) evolutions and its derivatives at a selected pixel as shown in FIG. 26 for temperature contrast example.

7. Analysis methods under Frame Images, Extracted Images or Analyzed saved have three options i.e., Edge Detection, Profile and Area Statistics.

Images extracted by scanning or searching for values from multiple frames are called Extracted Images. Images derived from Extracted Images are also called Extracted Images. A single frame number is not associated with extracted image. Extracted image method is integrated in an Extracted Images Panel. Extracted Images options are discussed herein.

Possible non-limiting examples of extracted image choices include:
  1. Maximum raw contrast
  2. Maximum raw contrast frame number
  3. Maximum smoothed contrast
  4. Maximum smoothed contrast frame number
  5. Maximum first derivative
  6. Maximum first derivative frame number
  7. Maximum second derivative
  8. Maximum second derivative frame number
  9. Peak contrast×peak time
  10. (Maximum of $1^{st}$ derivative contrast)×maximum contrast
  11. Maximum contrast−minimum contrast
  12. Maximum of $1^{st}$ derivative contrast−minimum of $1^{st}$ derivative contrast
  13. Maximum of $2^{nd}$ derivative contrast−minimum of $2^{nd}$ derivative contrast
  14. Maximum contrast×maximum of $2^{nd}$ derivative×maximum of $1^{st}$ derivative
  15. Maximum of $2^{nd}$ derivative×minimum of $2^{nd}$ derivative×maximum of $1^{st}$ derivative
  16. Masked images
  17. Standard deviation of any image
  18. Selected groups of frames of $C^W$, $C^{W'}$ or $C^{W''}$
  19. Selected frame numbers for $C^W$, $C^{W'}$ or $C^{W''}$
  20. Selected frame numbers associated with a peak of $C^W$, $C^{W'}$ or $C^{W''}$
  21. Selected frame numbers associated with values above a threshold value for $C^W$ or $C^{W'}$ or $C^{W''}$ 22. selected frame numbers of $C^W$ or $C^{W'}$ or $C^{W''}$ that are associated with values from a vertical or horizontal pixel line
23. Selected frame numbers of $C^W$, $C^{W'}$ or $C^{W''}$ that are associated with values from a selected pixel.
24. Selected groups of frames $C^C$, $C^{C'}$ or $C^{C''}$
25. Selected frame number of frames for $C^C$, $C^{C'}$ or $C^{C''}$
26. Selected frame number associated with a peak of $C^C$, $C^{C'}$ or $C^{C''}$
24. Selected frame number associated with a peak of at least one of $C^C$, $C^{C'}$ or $C^{C''}$
25. Selected frame numbers associated with values above a threshold value for $C^C$, $C^{C'}$ or $C^{C''}$
26. One or more selected frame numbers of $C^C$, $C^{C'}$ or $C^{C''}$ that are associated with values from a selected vertical or horizontal pixel line
27. Selected frame numbers of $C^C$, $C^{C'}$, $C^{C''}$ that are associated with values from a selected pixel
28. Selected groups of frames of $C^T$, $C^{T'}$ or $C^{T''}$
29. Selected frame number of frames for $C^T$, $C^{T'}$ or $C^{T''}$
30. Selected frame number associated with a peak of $C^T$, $C^{T'}$ or $C^{T''}$
31. Selected frame numbers associated with values above a threshold value of $C^T$, $C^{T'}$ or $C^{T''}$
32. Selected frame numbers of $C^T$, $C^{T'}$ or $C^{T''}$ that are associated with values from a vertical or horizontal pixel line
33. Selected frame numbers of $C^T$, $C^{T'}$ or $C^{T''}$ that are associated with values from a selected pixel
34. Normalized contrast frame number and contrast derivatives including for example maximum contrast frame number (no smoothing), maximum of $1^{st}$ derivative (4 point smoothing) and maximum of $1^{st}$ derivative (12 point smoothing) or other smoothing settings.
35. Maximum normalized contrast $2^{nd}$ derivative and peak product times including non-limiting examples of maximum of contrast $2^{nd}$ derivative (4 point smoothing), maximum of contrast $2^{nd}$ derivative (12 point smoothing) and peak product time=maximum contrast×maximum contrast frame number.
36. Normalized contrast images derived from other images such as but not limited to Maximum of contrast×maximum of $1^{st}$ derivative (taken with different smoothing) and maximum contrast−minimum contrast.
37. Normalized contrast images derived from other images may also include for example maximum $1^{st}$ derivative−minimum $1^{st}$ derivative taken with different smoothing.
38. Normalized contrast images derived from other images may also include maximum $2^{nd}$ derivative−minimum $2^{nd}$ derivative taken with different smoothing.
40. Normalized contrast images derived from other images may also include maximum of contrast×maximum of $1^{st}$ derivative×maximum of $2^{nd}$ derivative taken with different smoothing.
41. Normalized contrast images derived from other images may also include maximum of $2^{nd}$ derivative×minimum of $2^{nd}$ derivative×maximum of $1^{st}$ derivative taken with different smoothing.
42. Maximum normalized contrast and maximum normalized contrast derivatives including maximum contrast, maximum contrast $1^{st}$ derivative, and maximum contrast $2^{nd}$ derivative.
43. Maximum normalized contrast frame number, mask image, and masked frame number image such as maximum contrast frame number, Binary (mask) image of maximum contrast at threshold=0.1, and these items multiplied to provide a masked maximum contrast frame number.
44. Normalized contrast frame number and normalized contrast derivatives including maximum contrast $1^{st}$ derivative frame number, minimum contrast $1^{st}$ derivative frame number and minimum contrast $2^{nd}$ derivative.
45. Extracted normalized contrast image derived from other images may include peak product time=to maximum contrast×maximum contrast frame number, maximum of contrast×maximum of $1^{st}$ derivative contrast and maximum contrast−minimum contrast.
46. Extracted normalized contrast image derived from other images may include maximum $1^{st}$ derivative contrast−minimum $1^{st}$ derivative contrast, maximum $2^{nd}$ derivative contrast−minimum $2^{nd}$ derivative contrast, and maximum of contrast×maximum of $1^{st}$ derivative×maximum of $2^{nd}$ derivative.
47. Extracted normalized contrast image derived from other images may include maximum of $2^{nd}$ derivative×minimum of $2^{nd}$ derivative×maximum of $1^{st}$ derivative.
48. Extracted normalized contrast images of maximum contrast, standard deviation, of maximum normalized contrast, maximum normalized contrast $1^{st}$ derivative, and maximum normalized contrast $1^{st}$ derivative frame number (TOF—Time of flight scan)

Figure 35:
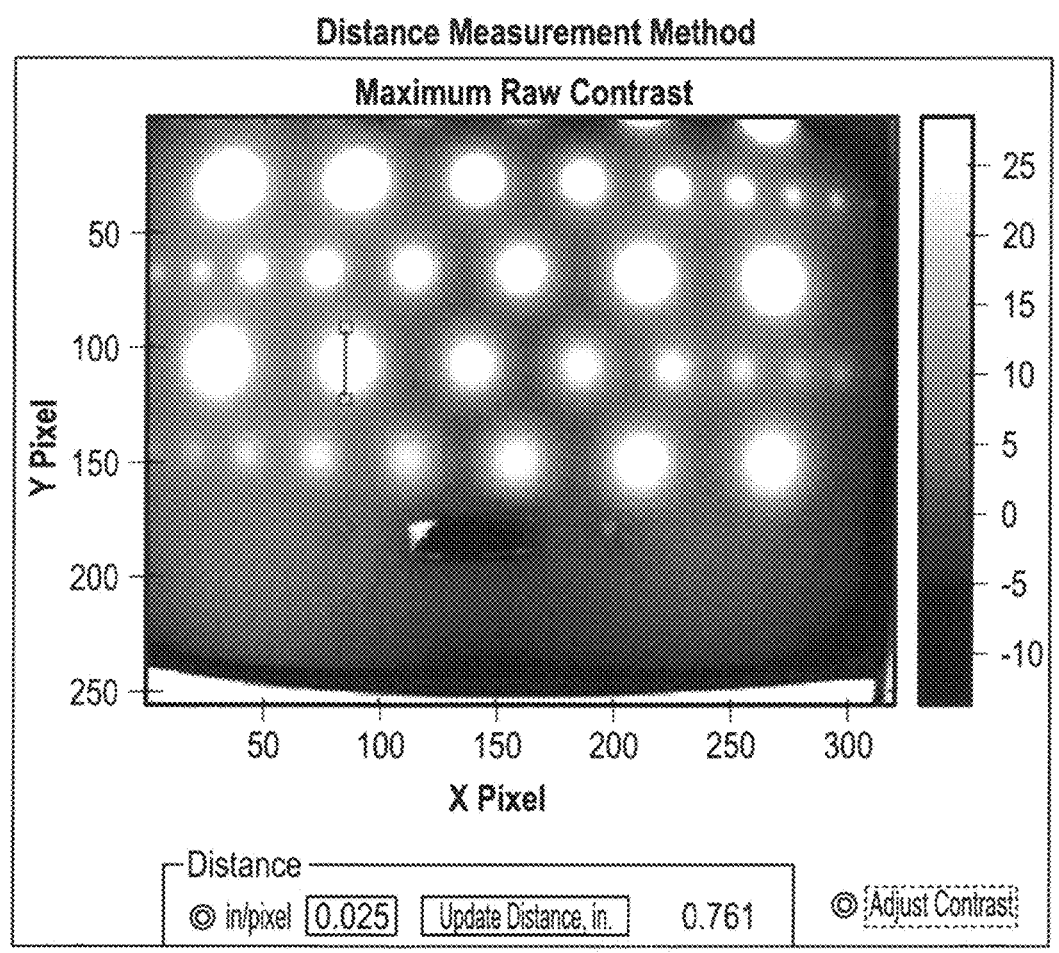
FIG. 35 shows a distance or flaw size measurement method in accord with one embodiment.

Distance or length measurement method using a line superimposition is applicable where 2D images are shown. See FIG. 35 where the line is indicated on an image and its length is indicated at the bottom right. The computer is operable to measure the length of the line. If desired, this line could be automatically produced. For example, automated edge detection as discussed herein could be utilized to locate the edges and the line could be generated and measured automatically in any desired direction.

8. Distance measurement is also available in Main panel, Frame images panel, Extracted images panel, and Analyze saved images panel. The distance measurement can be used to measure flaw size by dragging end points of the line to selected edge points of flaw indications.

Within the three data analysis methods there are other sub-methods including Edge detection for flaw size assessment, such as an automated edge detection using "Canny" method wherein an automated technique for detecting the edge of images for a hole is utilized. While the Canny method is know for detecting edges in prior art images, it is believed to be novel to not only detect edges but then determine a size of a flaw in IR images automatically. Using this method, a flaw might be selected by selecting a region around the flaw. While the Canny method is known for detecting edges, the use of the technique for measuring flaw size is novel. For example, in FIG. 35, the hole with the line or another hole may be selected by producing a box around the hole. The Canny method can then be used by the computer to automatically detect the edge of the flaw and the computer then determines the size of the flaw. It will be appreciated that a vertical line through the center of the hole or a horizontal line through the center of the hole can be graphed in terms of pixel brightness that ranges from dark near the edges to bright near the center and then dark again. It will be appreciated that for a hole in the drawing a bell shaped curve is produced for pixel intensity versus the x pixel line or y pixel line as the image moves from dark to light and to dark again. A desired value or percentage change or the like for the boundary value can be selected and whereupon a circumference can be plotted around the hole.

The computer can be programmed to measure the circumference for flaw sizing. The entire operation can be automated by letting the computer detect the desired amount of change that indicates the boundary. Various types of filters may be utilized for this purpose. For example if the range from dark to light in pixel value is from 10 to 40, then a pixel value of approximately 15 might be selected as the boundary or a desired percentage change necessary to indicate a boundary of a flaw. Once the desired amount of pixel change is known, then for other flaws or holes, the entire process of sizing the flaw is automated. Various types of filters such as Gaussian filters and the like may be utilized for detection of edges, as is known by those of skill in the art now having the benefit of this disclosure.

Image gray value profiling along vertical or horizontal lines or using peak of values.

A profile along chosen cross hair can be provided. For example, a vertical and horizontal line may be utilized to pick a particular pixel in an image. As a non-limiting, cross-hairs could be placed using the computer in a flaw or hole in a maximum raw contrast image. In this case, with the cross-hair might select x pixel=140 and y pixel=108. Then two graphs could be produced. For the vertical profile at x pixel=140 the graph may display the Value for maximum raw contrast versus the Y pixel value. For the horizontal profile at Y pixel=108, the graph may display the value for maximum raw contrast versus the x pixel. If a horizontal line goes through a series of holes the pixel values versus the pixel position would show a series of peaks and valleys.

Area Statistics. Standard deviation is measure of noise in the data and is used to compute signal-to-noise ratio. For example, an area could be selected such as in a processed normalized contrast frame or another frame. This area can be enlarged and the mean and standard deviation is calculated in the selected area.

Chosen pixel coordinates can be displayed to measure flaw size on any 2D image.

Analyze Saved images methods are integrated in Analyze Saved images computer screen panel. The Images method creates a mosaic or multiple images, e.g. four images, in each file. Image Comparison method compares images to reference images and may compare multiple images as desired. The process involves image registration to reference images and then subtraction from the reference images. The process may selectively utilize a mosaic of reference images and a separate mosaic of evaluation images. The embodiment is operable to show a mosaic of registered evaluation images and a separate mosaic of superimposed registered evaluation images with reference images. The embodiment is operable to show subtraction of registered images from reference images to assess gray value (e.g. peak of normalized contrast) difference in indications. Multiple image files may be opened with an image registration between a first set of image files and a second set of image files if desired. Storage may be provided for a mosaic of analysis images, a mosaic of reference images, a mosaic of registered analysis images, a mosaic of subtraction of registered analysis images from reference images, and/or a mosaic of superposition images of registered analysis images and reference images. Operations on these images may also include contrast adjustment, length measurement, and saving the images in file formats such as .mat, .fig. jpg and the like. Examples might include a mosaic of reference images such as maximum normalized contrast or a mosaic of evaluation images such as maximum normalized contrast. Other mosaics might include registered evaluation images or superimposed registered evaluation images with reference images.

Thus, differences in the thermal response (e.g. normalized contrast) can be quantified and used for monitoring the material condition for flaw growth.

Flash Thermography Response, Accept/Reject Threshold and POD Analysis

Use of Peak Contrast in Probability of Detection (POD) Analysis

Diameter-to-depth ratio (D/d) can be used to establish a correlation with peak contrast for POD analysis as peak contrast provides a monotonic change with the diameter-to-depth ratio. As discussed herein, an exponential fit equation may be used and provide a resulting 90% predication bounds and 95% confidence bounds. Depending upon the accept/reject detection threshold level used for peak contrast, a90/95 POD size of the diameter-to-depth ratio can be directly read from these plots. Such an approach gives a linear relationship between diameter and depth for 90% POD with 95% confidence. A more complex relationship can be obtained using peak contrast map method given below. For example, a first graph may display peak contrast v D/d ratio with 95% boundaries shown in the graph. A fit curve may be provided at roughly the centerline between the 95% boundary lines. Various points for peak contrast vs D/d ratio may be plotted onto the graph. Some of the points for peak contrast vs D/d ratio may fall just outside the 95% boundaries with other points being inside. In another example, the same graph may be provided with 90% boundaries shown on the graph where all of the points for the peak contrast vs D/d ratio all fall within the 90% boundary lines.

Using Calibration Data in Probability of Detection (POD) Analysis

Peak contrast parameter calibration data from FIG. 32 can be used to predict peak contrast $C_{peak}$. Here, it is assumed that the thermography response is modeled as a surface in the calibration data. In another embodiment, the method utilizes a polynomial function surface fit to the peak contrast data as discussed herein. Interpolated data from FIG. 32 can be used for prediction. The predicated peak contrast can be used as the transformed flaw size parameter denoted as 'a' in MIL-HDBK-1823. The diameter-depth pairs are transformed into peak contrast values using the fitted or interpolated calibration peak contrast data. The actual peak contrast (Cpeak) is used as the signal response denoted as 'â'. It should be noted that the noise is also measured in peak contrast units. If interpolated calibration data is used, it is recommended to use separate artificial flaw samples for POD analysis. If fitted data is used, the calibration sample can be used for POD analysis. The 'â' versus the calibration transformed 'a' POD analysis provides the a90/95 peak contrast value. The value needs to be converted to an a90/95 relationship between the diameter and depth.

Figure 36:
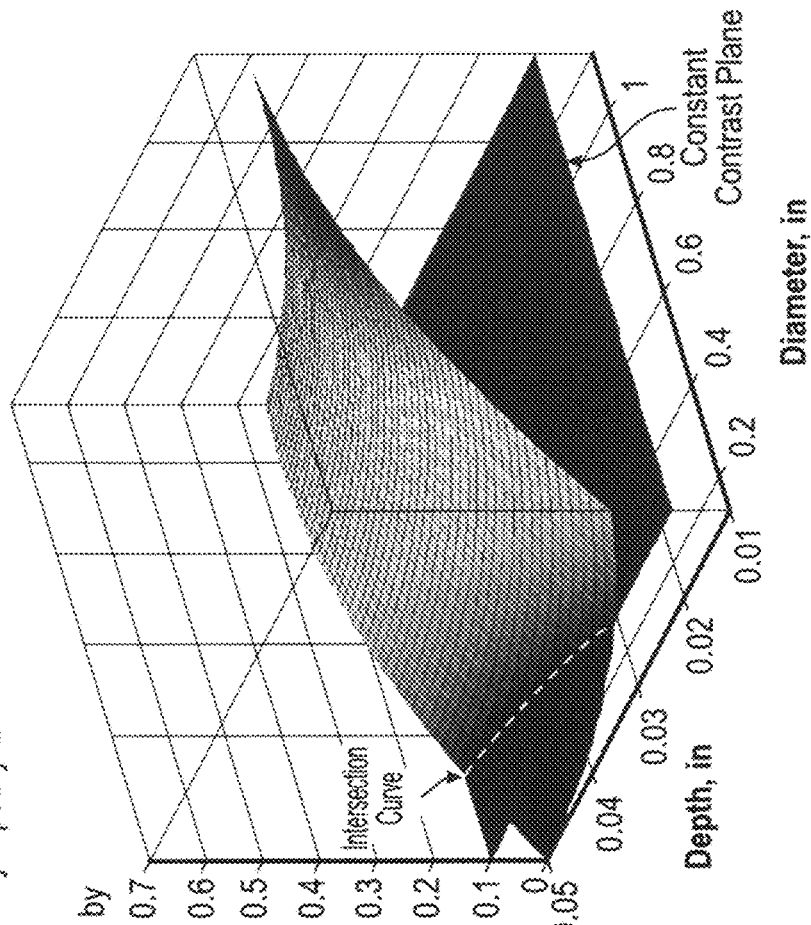
FIG. 36 shows surface fitted to peak Normalized Contrast data, chosen peak contrast plane, intersection curve defining relationship between flaw size and depth in accord with one embodiment.

Using FIG. 36, the 90/95 diameter-depth pair line can be predicated as an intersection of peak contrast fit map with a plane defined by a90/95 peak contrast value. Here, the surface was fitted as a second order polynomial or ellipsoid. The intersection line is given as an equation of an ellipse. In an example given in FIG. 36, substitute f(x, y)=0.1 which is the chosen value for peak contrast (normalized −1 to 1). This provides an equation defining the 90/95 diameter-to-depth relationship. The equation defines an elliptical arc which is probably a better description of a90/95 than the linear relationship obtained using diameter-to-depth ratio POD analysis. This POD approach is expected to significantly reduce number of flaws needed in the POD study. The approach can be referred to as the calibration transformed POD.

Figure 37:
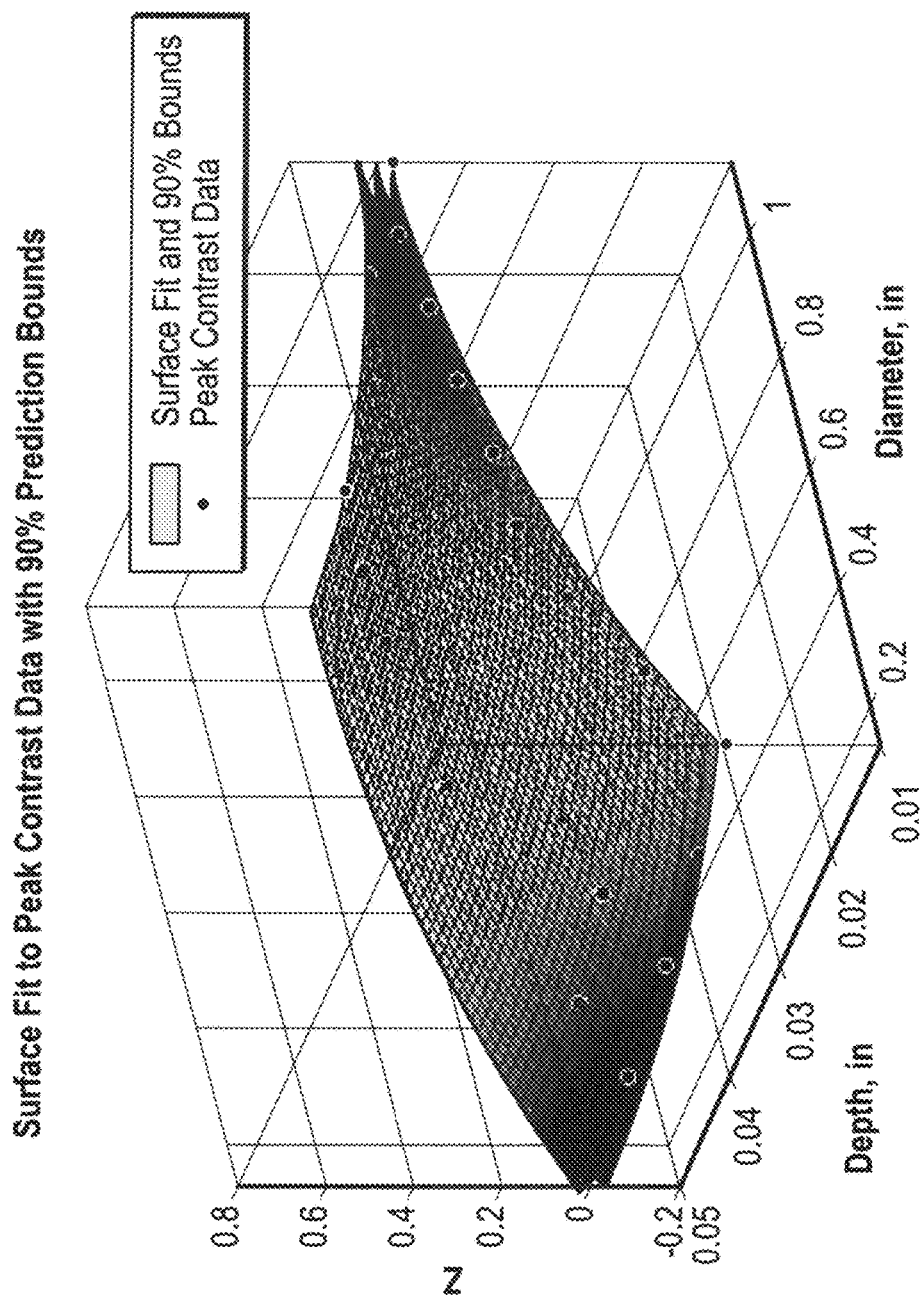
FIG. 37 shows a surface fit to peak contrast data with 90% prediction bounds in accord with one embodiment.

Finally, the calibration peak contrast maps can be directly used in the POD analysis. For the a90/95 estimate use FIG. 37 which provides 90% prediction bounds of peak contrast surface in Matlab surface fit tool. The 95% confidence bound at a desired diameter-depth pair can be calculated from the fit equation given in FIG. 19. Using FIG. 37, the a90/95 diameter-depth pair line can be determined as an intersection of the 90% upper bound peak contrast fit surface with a plane defining peak contrast detection threshold value similar to that shown in FIG. 36. This approach can be described as POD from predication bounds to the contrast map.

Flaw size parameter, a90/95 calculated using the normalized contrast is primarily affected by the detection threshold-to-noise ratio. Therefore, the a90/95 diameter-depth relationship is transferable between thermography set-ups, if detection threshold-to-noise ratio is comparable to that in the POD study.

Using Simple Contrast and Referenced Simple Contrast in Flaw Detection

A reference flaw specimen or a reference test specimen can be accommodated with the test object or used concurrently, both appearing in the camera field of view at the time of the data acquisition. A reference test specimen may not have a programmed flaw in it and is anomaly free with same material specification as the test object. A reference flaw specimen has at least one programmed flaw in otherwise anomaly free material with same material specification as the test object.

The reference flaw specimen, used concurrently, can be used to assist in simple contrast evaluations. Concurrent use of reference helps in all contrast methods where monitoring of contrast based parameters is desired.

The relative pixel intensity or the simple contrast is given by, $$R = W - W_{ref},\quad (43)$$

W=pixel intensity at the measurement ROI at post-flash time t,
$W_{ref}$=pixel intensity at the reference ROI at the post-flash time t, and Since simple contrast is dependent upon the flash intensity and camera type among other factors, simple contrast from a reference flaw can be used to normalize the simple contrast.

The simple contrast of a reference flaw is given by, $$R_f = W_f - W_{ref},\quad (44)$$

where,
$R_f$=simple contrast of a reference flaw and
$W_f$=pixel intensity of ROI at a reference flaw.

Peak contrast from a reference flaw can be used to calculate referenced simple contrast as, $$R_{ref} = R/R_{f,peak},\quad (45)$$

where,
$R_{ref}$=referenced simple contrast and
$R_{f,peak}$=simple contrast of a reference flaw.

The referenced simple contrast is less dependent on the flash thermography set-up. Similarly, the detection threshold can be referenced to peak contrast from the reference flaw. The percent detection (decision) threshold is given as, $$\%R_{thr} = 100(R_{thr}/R_{f,peak}),\quad (46)$$

$R_{thr}$=detection threshold for simple contrast and
$\%R_{thr}$=percent detection threshold.

In other words the referenced simple contrast process may comprise steps such as placing the reference flaw standard on or next to the test object to appear in the IR image concurrently with the test object. Subsequently, the flash IR data acquisition is performed. The reference ROI in on the reference standard good area. The relative pix intensityon the test object is calculated using equation 43. The simple contrast of the reference flaw is calculated using equation 44. The referenced simple contrast is calculated using equation 45. The threshold detection threshold is chosen using equation 46.

Using Simple Contrast and Referenced Simple Contrast in Pod Analysis

Since normalized peak contrast provides good correlation to flaw characteristics (diameter, depth etc.), it is expected that referenced simple contrast and simple contrast also provide correlation to flaw characteristics. The methods given here are equally applicable to analysis using the simple contrast. Therefore, the POD analysis can be done using the simple contrast (R or Rref) too. Data of the peak simple contrast (Rpeak) versus the diameter-to-depth ratio can be used in â versus a POD analysis. The referenced contrast calculation needs a calibration standard in an identical test set-up or the reference standard is used concurrently with the part. This may not be practical in some cases.

Alternatively, the simple peak contrast map with respect to diameter-depth data can be analyzed to obtain the POD estimates similar to that used for the normalized peak contrast e.g. POD using the calibration transform and POD using the prediction bound to the contrast map methods.

The simple contrast is influenced by flash intensity and type of the camera. Therefore, to maintain detection sensitivity, the detection threshold level should be established as a percentage of simple peak contrast (Rf) from a selected reference calibration flaw. Similarly peak contrast can be normalized to the reference flaw peak contrast by simply dividing by the reference flaw peak contrast. The resulting contrast is called the referenced simple contrast (Rref,peak). The influence of camera model and flash intensity are minimized if same value of the percent detection threshold is used between set-ups.

The a90/95 flaw size is primarily related to the detection threshold-to-noise ratio and percent threshold level. Therefore, the a90/95 diameter-depth relationship obtained using the simple contrast (Rpeak or Rref,peak) is transferable between thermography set-ups if the detection threshold-to-noise ratio and percent detection level are comparable to that used in the POD study. The simple contrast has less noise compared to the normalized contrast and may provide a smaller a90/95 flaw size for a given threshold-to-noise ratio.

A pass/fail POD per MIL-HDBK-1823 is also possible. Here, a thermography frame with most visible contrast is selected from appropriately processed data sequence. A consistent flaw detection procedure is applied in the POD study. The result is noted as "pass" if the flaw is detected and "fail" if the flaw is not detected. The flaw diameter-depth pairs are transformed to diameter-to-depth ratios (D/d). The resulting data is used in the POD analysis. Alternatively, the diameter-depth pairs are transformed to the calibrated normalized or calibrated referenced simple peak contrast. This data is then used in the pass/fail POD analysis. This approach is likely to provide even smaller a90/95 diameter-to-depth values compared to the â versus a approaches as the flaw detection is based on perception of the flaw by viewing images.

CONCLUSIONS

Normalized Contrast and Derivative (NCD) Method

The embodiments described herein are applicable to flash (pulsed) thermography nondestructive evaluation. They are an enhancement of the contrast and feature imaging methods previously described in U.S. Pat. Nos. 9,066,028 and 8,577,120. Two different methods of the derivatives have been provided. The first method involves derivative of the raw (method 1A) contrast evolution data or the smooth (method 1B) contrast evolution data using the smoothing during the calculation of derivatives. The second method involves derivative of the curve fit (method 2) contrast evolution which may be fitted to either the raw or smooth data. In method 2A, curve fit is also a simulation fit (e.g. polynomial fit) to the contrast simulation. A variation of the second method i.e. method 2B involves curve fit (non-simulation) to the raw or smooth contrast evolution and then the derivatives are computed from the curve fit equation.

Both methods convert acquired flash thermography IR data to contrast video sequence data with or without smoothing. Subsequently, both methods can be used to convert contrast video sequence data to first derivative video sequence data and the second derivative video sequence data.

Then, several non-derivative (e.g. contrast) and derivative (e.g. first and second derivative) features are extracted as well as features at selected frame numbers are extracted as images. Depending upon feature, the images may reveal anomaly information such as the anomaly depth (e.g. frame number related images), anomaly size (e.g. contrast and contrast derivatives), anomaly gap thickness (e.g. peak product time) and provide suppression of temporal and spatial noise. All images are described as the contrast A-scan, contrast B-scan, contrast value C-scan and contrast time C-scan similar to the traditional ultrasonic pulse/echo scans.

There are advantages as well as disadvantages of each method. The simulation fit method 2A and the non-simulation curve fit method 2B methods require that the curve fit is established first. If the fits cannot be established accurately due to non-ideal test conditions, low contrast value, choice of fit model etc., then the results would be in error. However, the derivatives are calculated from the fit equations and therefore the resolution is excellent compared to that from method 1. The smooth derivative values of method 1 depend upon the length of the smoothing span. Longer smoothing span provides better suppression of the pixel temporal noise but they also flatten the contrast evolution. The smoothing in derivatives also shifts the peak in the first derivative which may be used to your advantage in many situations. Detection of flat bottom holes in the provided images validates the method of contrast and feature imaging.

Converted Contrast and Derivative Method (CCD)

This method is also applicable to flash (pulsed) thermography nondestructive evaluation, for it is a variation of the contrast and feature imaging method previously described in U.S. Pat. Nos. 9,066,028 and 8,577,120. Here, a contrast method of implied reference (ROI) is introduced. The method allows extraction of the pixel intensity based converted evolutions that have similar shape characteristics to the shape of the corresponding normalized contrast evolution. For delamination like void, the shape of the normalized contrast evolution is similar to a backward skewed statistical distribution. Thus, the converted contrast evolutions can be analyzed by measuring the peak amplitude and peak time. In addition, the first and second derivatives can also be computed. Similar to the normalized contrast A-scan, B-scan and C-scans, the converted contrast also provides A-scan, B-scan and C-scans. The method uses a multiplier function that is empirically derived (or statistically fitted) to convert the relative pixel intensity to the converted contrast. A simple multiplier function uses fractional power of the frame time. More complex but better fitting functions can be derived based on the equation fitted to the relative pixel intensity of the reference region. A method is provided to compute the normalized contrast from the converted contrast.

Although, the converted contrast cannot be used for the simulation match, the converted contrast method provides an advantage over the normalized contrast by eliminating or reducing use of the reference ROI. For flaw detection, results from the converted contrast are as good as or better than the normalized contrast due to use of larger numbers which provide better graphical display in the software used. Depending upon the choice of the multiplier function, the converted contrast may show the afterglow/texture effect in the images. However, it may he advantageous to have the ability to evaluate data for texture effects. Filtering or gating the evolution can be used to reduce the afterglow/texture effect if desired as well as frame gating is used to exclude earlier images from analysis.

Normalized Temperature Contrast and Derivative (TCD) Method

This method computes surface temperature video sequence data. Normalized temperature contrast and smooth normalized temperature contrast video sequence data are computed. Temperature rise video sequence data and simple contrast video sequence data are computed in this method. First and second derivative video sequence data of smooth normalized temperature contrast data are also computed. Selected Frame Image Analysis (FIA) and Extracted Image Analysis (EIA) are also applicable to Normalized Temperature Contrast method. Similar to that for the normalized contrast video, A-scan, B-scan and C-scans are possible with the normalized temperature contrast and the imaging results are comparable or better than the normalized contrast A-scan, B-scan and C-scans due to correction for the varying reflection temperature.

The temperature contrast method reduces influence of diffused reflection from the part surface, enhancing the contrast. Also, surface temperature measurements are more quantitative than the pixel intensity measurements which contain both the emissive and reflective components of irradiance forming the image.

Contrast Evolution Calibration and Analysis (CECA) Method

This method provides an empirical method of calibrating the flash thermography response in nondestructive evaluation. The contrast calibration method (CECA) is applied to the normalized contrast data for a pixel with peak of relative contrast for the indication.

First a physical calibration standard with artificial flaws such as flat bottom holes with desired diameter and depth values in a desired material is fabricated. Long flat bottom slots can be used in calibration standard. For tight delaminations, use a standard that simulates the desired condition. U.S. Pat. No. 8,577,120 provides a comparison of normalized contrast response from slots and holes. It maps slot width to equivalent flat bottom hole width, which then can be used in evaluating depth of long indications.

Normalized contrast evolution data for each artificial flaw in the reference standard is preferably extracted from the raw video sequence data. The contrast evolution files are analyzed in the contrast evolution evaluation methods provided. Six contrast parameters are extracted for each flaw in the calibration standard. A calibration data set is prepared from the contrast parameter data. The calibration data is plotted by using an evolution evaluation and calibration method described here. In order to analyze a given contrast evolution for flaw depth, contrast evolution parameters are calculated, diameter or widths are measured in 2D images of the anomaly. Depth is preferably assessed in the method by using the anomaly diameter or width, the six contrast evolution parameters and calibration data. A single depth estimate can be interpolated from the multiple depth estimates, one each from the six evolution parameters.

Other Image and Data Analysis Methods

These methods provide Frame Images, Extracted Images, and Analyze saved images, which may be selectively chosen for activation from a computer screen. Video frame images are called Frame Images here. A frame number is associated with the frame image and may be referred to herein as a frame number wherein the frame number calls for a frame image. Images extracted by scanning for values from multiple frames are called Extracted Images. A single frame number is not associated with extracted image.

For each of the three video sequence data types (e.g. normalized contrast, converted contrast and normalized temperature contrast), there are other sub-methods including, flaw size measurement, edge detection, image gray value profiling along vertical or horizontal lines and image gray value profiling using peak values scanned along pixel lines in vertical and horizontal directions. In accord with the embodiments described herein, the methods to create these video sequence data types, which may also be referred to as video data herein, may be pulled up from one or more computer screens, some of which were discussed or shown herein. The computer screens provide the options for each of the steps during process.

Under analyze saved images a sub-method of image comparison (registration, subtraction and superimposition) to assess changes in thermography response (i.e. raw or processed pixel intensity data) and image tiling or mosaic is also used. They provide useful information depending upon user need. Accordingly, the embodiments described herein provide display of computer imagery that allow selection of image comparison methods.

Saved images are further analyzed by creating a mosaic. The images can be compared to reference images by a process called image registration and then subtracted from the reference images. Thus, differences in the thermal response (e.g. normalized contrast) between pairs of images can be quantified.

Thermography Response, Accept/Reject Threshold and Pod Analysis

The methods given here provide quantitative thermography response such as the peak normalized contrast, peak converted contrast and peak normalized temperature contrast, simple contrast and referenced simple contrast etc. that can be used for flaw detection based on establishing accept/reject threshold level for thermography response. These thermography responses can be used in probability of detection (POD) analysis based on thermography response correlation to diameter/depth ratio (Method 1A).

The diameter/depth ratio curve fit to thermography response can be used as transformation of diameter/depth ratio to predicted thermography response (e.g. peak contrast). Using linear correlation between actual thermography response and predicted thermography response along with decision threshold for actual thermography response, a90/95 for predicated thermography response can be calculated. The a90/95 predicated thermography response is then transformed back to a90/95 for diameter/depth ratio (Method 1B)

Similarly, correlation of thermography response to both diameter and depth given as fitted surfaces and thermography response threshold plane is used perform POD analysis (Method 2A).

Another approach uses the calibration data for thermography response map as a transformation matrix to convert the diameter-depth pairs to predicted thermography response which is used as the transformed flaw size parameter to correlate to actual thermography response. Using linear correlation between actual thermography response and predicted thermography response along with decision threshold for actual thermography response. a90/95 for predicated thermography response can be calculated. The a90/95 predicated thermography response is then transformed back to a90/95 for diameter/depth ratio (Method 2B). A couple of pass/fail POD approaches are also provided (Method 3).

The foregoing description of the exemplary embodiments has been presented for purposes of illustration and description only. It is not intended to be exhaustive, nor to limit the exemplary embodiments to the precise form disclosed; and many modifications and variations are possible in light of the above teachings. Such modifications and variations that may be apparent to a person skilled in the art are intended to be included within the scope of the inventive concepts as defined by the accompanying claims.

The invention claimed is:
1. A method to create video data for infrared flash thermography, comprising:
  selecting a frame of a video comprising a sequence of frames of surface temperature in terms of pixel intensity of a surface of a material under evaluation after application of a flash of heat;
  selecting a measurement region of interest (ROI) and a reference ROI in said frame; and
  computing video data corresponding with the following equations for a plurality of frames after said flash of heat:

$$C^C = \Delta Wf$$

where,
$C^C$=a converted contrast,
$\Delta W$=a change in a pixel intensity after said flash of heat, and $$f(t) = \frac{B}{\Delta W_{ref}} = \frac{Bt^{-s}}{M}$$

where,
B=a baseline value,
$\Delta W_{ref}$=change in said pixel intensity of said reference ROI after said flash of heat, and
M=a multiplier that depends on a highest pixel intensity value that occurs after said flash of heat.

2. The method of claim 1, further comprising utilizing raw video or smoothed video for said step of computing.

3. The method of claim 2, further comprising computing a slope and a multiplier consistent with the following equations:

$$s = \frac{d\ln(\Delta W_{ref})}{d\ln(t)} = \frac{d(\Delta W_{ref})}{dt} \frac{t}{\Delta W_{ref}}, \text{ and}$$

$$M = e^{(\ln(\Delta W_{ref}) - s\ln(t))} = \frac{\Delta W_{ref}}{t^s},$$

where,
s=a slope of a selected portion of a log-log reference relative pixel intensity plot,
M=a multiplier.

4. The method of claim 2, further comprising selectively computing said converted contrast $C^C$ from a normalized contrast $C^W$ or selectively computing said normalized contrast $C^W$ from said converted contrast $C^C$, where $$C^W = \frac{\Delta W - \Delta W_{ref}}{\Delta W + \Delta W_{ref}}.$$

$$\Delta W = W - W^0$$

$$\Delta W_{ref} = W_{ref} - W_{ref}^0$$

where,
$C^W$=said normalized contrast at a time t,
$\Delta W$=change in a pixel intensity of said measurement ROI after said flash of heat,
W=said pixel intensity at said measurement ROI at a post-flash time t,
$W^0$=said pixel intensity at said measurement ROI before said flash of heat,
$\Delta W_{ref}$=change in said pixel intensity of said reference ROI after said flash of heat,
$W_{ref}$=said pixel intensity at said reference ROI at said post-flash time t, and
$W_{ref}^0$=said pixel intensity at said reference ROI before said flash of heat.

5. The method of claim 4, wherein said converted contrast $C^C$ is related to normalized contrast $C^W$ consistent with the following equation:

$$C^W = \frac{C^c - C_{ref}^c}{C^c + C_{ref}^c} \cong \frac{C^c - B}{C^c + B},$$

$$C^c \cong B \frac{1 + C^W}{1 - C^W}.$$

6. The method of claim 5, further comprising creating for said plurality of frames additional video data consistent with the following time derivative:
a first derivative $C^{C\prime} = dC^C/dt$.

7. The method of claim 6, further comprising creating for said plurality of frames additional video data corresponding with the following time derivative:
a second derivative $C^{C\prime\prime} = dC^{C\prime}/dt$.

8. The method of claim 6, wherein said first derivative is taken when said $C^C$ is computed utilizing said raw video and then smoothing during said creating of said first derivative.

9. The method of claim 6, wherein said first derivative is taken when said $C^C$ is computed utilizing said smoothed video produced from said raw video.

10. The method of claim 6, wherein said first derivative is taken of a non-simulation curve fit to said $C^C$ for said plurality of frames and wherein said $C^C$ is computed utilizing either said raw video or said smoothed video, said first derivative being computed from one or more equations of said non-simulation curve fit.

11. The method of claim 6, wherein said first derivative is taken of a simulation curve fit to said $C^C$ for said plurality of frames and wherein said $C^C$ is computed utilizing either said raw video or said smoothed video, said first derivative being computed from one or more equations of said simulation curve fit.

12. The method of claim 7, further comprising combining image data from said plurality of frames of said video for at least one of said $C^C$ or said $C^{C\prime}$ or said $C^{C\prime\prime}$ to produce an extracted image.

13. The method of claim 7, further comprising utilizing image data from a selected frame number of said plurality of frames of said video for said $C^C$ or said $C^{C\prime}$ or said $C^{C\prime\prime}$ to produce a frame image.

14. The method of claim 7, further comprising combining image data from a frame number associated with at least one of peak or a minimum or an average or a selected frame feature value or a combination of feature images for at least one of said $C^C$ or said $C^{C\prime}$ or said $C^{C\prime\prime}$ to produce an extracted image.

15. The method of claim 7, further comprising combining image data from frame numbers associated with values above a threshold value for at least one of said $C^C$ or said $C^{C\prime}$ or said $C^{C\prime\prime}$ to produce an extracted image.

16. The method of claim 7, further comprising combining image data from frame numbers of at least one of said $C^C$ or said $C^{C\prime}$ or said $C^{C\prime\prime}$ that are associated with values from a selected vertical or horizontal pixel line to produce an extracted image.

17. The method of claim 7, further comprising combining image data from frame numbers for at least one of said $C^C$ or said $C^{C\prime}$ or said $C^{C\prime\prime}$ that are associated with values from a selected pixel to produce an extracted image.

18. The method of claim 1, further comprising measuring a size of a flaw on said frame of said video utilizing a superimposed line and providing a computerized distance measurement of said superimposed line.

19. The method of claim 1, further comprising measuring a size of a flaw on said frame of said video utilizing automated edge detection.

20. The method of claim 1, further comprising monitoring growth of a flaw by producing reference images and comparing said reference images to subsequently produced images.

21. The method of claim 20, wherein said step of comparing is made by at least one of image registration, superimposition, or subtraction.

22. The method claim 1, further comprising:
providing a calibration standard comprising at least one opening having a known diameter and a known depth;
wherein said step of computing video data further comprises utilizing said calibration standard and an anomaly indication as said material under evaluation.

23. The method of claim 22, wherein said reference ROI is selected on an anomaly free area of said calibration standard.

24. The method of claim 1, further comprising utilizing a value consistent with a diameter to depth ratio of a flaw as a flaw size input to calculate a probability of detection of a flaw.

25. The method of claim 1, further comprising determining a percent detection threshold for a probability of detection of a flaw consistent with the following equations $$R = W - W_{ref},$$

where,
R=a relative pixel intensity
W=a pixel intensity at said measurement ROI at a post-flash time t,
$W_{ref}$=a pixel intensity at said reference ROI at said post-flash time t, $$R_f = W_f - W_{ref},$$

where,
$R_f$=a contrast of a reference flaw and
$W_f$=a pixel intensity of ROI at a reference flaw;

$$R_{ref} = R/R_{f,peak},$$

where,
$R_{ref}$=a referenced contrast,
$R_{f,peak}$=a contrast of a reference flaw; and $$\%R_{thr} = 100(R_{thr}/R_{f,peak}),$$

where,
$R_{thr}$=a detection threshold for simple contrast and
$\%R_{thr}$=said percent detection threshold.

26. The method of claim 1, further comprising utilizing a thermography response to diameter and depth correlation to determine a probability of detection of a flaw.

27. A method for characterizing an unknown anomaly in a material, said method comprising:
recording flash thermography video data as a sequence of digital frames based on artificial anomalies of known diameter and depth values;
computing contrast evolution data for said artificial anomalies of known diameter and depth values to provide known computed contrast evolution data;
calculating contrast evolution parameters for said artificial anomalies of known diameter and depth values to provide known calculated contrast evolution parameters, said known calculated contrast evolution parameters comprising at least three of: a peak contrast, a peak time, time scale factor, offset time, begin time, and slope;
computing an unknown contrast evolution of said unknown anomaly; and
using at least one of said computed contrast evolution data or said known calculated contrast evolution parameters with said unknown contrast evolution of said unknown anomaly to characterize diameter and depth of said unknown anomaly.

28. The method of claim 27, wherein said step of calculating known contrast evolution data comprises a single point extraction for a round anomaly or multipoint extraction for a linear anomaly.

29. The method of claim 27, filtering said contrast evolution of said unknown anomaly.

30. The method of claim 27, wherein computing said unknown contrast evolution comprises:
calculating a normalized contrast, wherein said calculating of said normalized contrast comprises calculating a ratio of:
a change in pixel intensity at a measurement region of interest minus a change in pixel intensity at a reference region of interest compared to a sum of said change in pixel intensity at said measurement region of interest and said change in pixel intensity at said reference region of interest.

31. The method of claim 27, wherein computing said unknown contrast evolution comprises calculating a simple pixel intensity contrast, wherein said calculating of said simple pixel intensity contrast is determined by finding a difference between a pixel intensity at a measurement region of interest at post-flash time t and a pixel intensity at a reference region of interest at said post-flash time t.

32. An apparatus for characterizing an unknown anomaly in a material comprising:
a processor, and
a memory storing instructions that, when executed, cause said apparatus to:
calculate contrast evolution parameters for said unknown anomaly comprising at least three of: a peak contrast, a peak time, time scale factor, offset time, begin time, and slope; and
wherein a determination of a diameter and a depth of said unknown anomaly is performed by relating said calculated contrast parameters for said unknown anomaly to contrast parameters created from a calibration file empirically derived from a plurality of artificial anomalies of known diameter and depth.

33. The apparatus of claim 32 wherein said instructions cause said apparatus to produce a contrast evolution and to filter said contrast evolution.

34. A method for characterizing an unknown anomaly of unknown diameter and depth in a material, said method comprising:
recording flash thermography video data as a sequence of digital frames based on artificial anomalies of known diameter and depth values;
recording flash thermography video data as a sequence of digital frames based on said unknown anomaly of unknown diameter and depth;
calculating contrast evolution parameters in a calibration file comprising at least three of: a peak contrast, a peak time, time scale factor, offset time, begin time, and slope from said artificial anomalies of known diameter and depth values; and
determining said unknown diameter and depth of said unknown anomaly utilizing said calibration file.

35. The method of claim 34 comprising producing at least one of a normalized contrast, converted contrast or a normalized temperature contrast.

* * * * *